United States Patent
Kim et al.

(10) Patent No.: US 11,384,370 B2
(45) Date of Patent: Jul. 12, 2022

(54) MICROORGANISM FOR PRODUCING A MYCOSPORINE-LIKE AMINO ACID AND METHOD FOR PRODUCING A MYCOSPORINE-LIKE AMINO ACID USING THE SAME

(71) Applicant: CJ CheilJedang Corporation, Seoul (KR)

(72) Inventors: Sol Kim, Seoul (KR); Kyusung Lee, Seoul (KR); Joo Hee Lee, Seoul (KR); Jong-cheol Seok, Seoul (KR); Jae Woo Jang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/639,200

(22) PCT Filed: Aug. 13, 2018

(86) PCT No.: PCT/KR2018/009246
§ 371 (c)(1),
(2) Date: Apr. 22, 2020

(87) PCT Pub. No.: WO2019/035612
PCT Pub. Date: Feb. 21, 2019

(65) Prior Publication Data
US 2020/0283810 A1    Sep. 10, 2020

(30) Foreign Application Priority Data
Aug. 16, 2017  (KR) .................. 10-2017-0103795

(51) Int. Cl.
| | |
|---|---|
| *C12P 13/00* | (2006.01) |
| *C12N 15/70* | (2006.01) |
| *C12N 15/77* | (2006.01) |
| *C12N 15/81* | (2006.01) |
| *C12N 1/21* | (2006.01) |
| *C12N 9/88* | (2006.01) |
| *C12N 9/10* | (2006.01) |
| *C12N 9/00* | (2006.01) |

(52) U.S. Cl.
CPC .......... *C12P 13/005* (2013.01); *C12N 9/1007* (2013.01); *C12N 9/1022* (2013.01); *C12N 9/1085* (2013.01); *C12N 9/88* (2013.01); *C12N 15/70* (2013.01); *C12N 15/77* (2013.01); *C12N 15/81* (2013.01); *C12Y 603/04* (2013.01); *C12N 9/93* (2013.01); *C12Y 201/01* (2013.01); *C12Y 202/01001* (2013.01); *C12Y 205/01054* (2013.01); *C12Y 402/0101* (2013.01); *C12Y 402/03004* (2013.01)

(58) Field of Classification Search
None
See application file for complete search history.

(56) References Cited

FOREIGN PATENT DOCUMENTS

| | | |
|---|---|---|
| EP | 0663011 B1 | 2/2004 |
| EP | 3754024 A1 | 12/2020 |
| KR | 1020150065170 A | 6/2015 |
| KR | 1020150136961 B1 | 12/2015 |
| KR | 1020170002587 A | 1/2017 |
| WO | 2019017740 A1 | 1/2019 |

OTHER PUBLICATIONS

Jain et al., Cyanobacteria as efficient producers of mycosporine-like amino acids, J. Basic Microbiol. 57, May 2017, 715-27. (Year: 2017).*
Cha et al., Synthesis of Chlorogenic Acid and p-Coumaroyl Shikimates from Glucose Using Engineered *Escherichia coli*, J. Mircobiol. Biotechnol. 24, 2014, 1109-17. (Year: 2014).*
Pope et al., O-Methyltransferase Is Shared between the Pentose Phosphate and Shikimate Pathways and Is Essential for Mycosporine-Like Amino Acid Biosynthesis in Anabaena variabilis ATCC 29413, ChemBioChem 16, 2015, 320-27. (Year: 2015).*
Balskus et al., The genetic and molecular basis for sunscreen biosynthesis in cyanobacteria, Science 329, 2010, 1653-56 and supplemental materials. (Year: 2010).*
Balskus, Emily P. et al. "The Genetic and Molecular Basis for Suncreen Biosynthesis in Cyanobacteria" Science vol. Sep. 24, 2010, pp. 1653-1656.
Cardozo, Karina H.M. et al. "Metabolites from algae with economical impact" Science Direct Comparative Biochemistry and Physiology, Part C 146 (207) 60-78.
Cockell, Charles S. et al. "Ultraviolet radiation screening compounds" Biol. Rev. (1999), 74, pp. 311-345.
Dunlap, Walter C. et al. "Small-molecule antioxidants in marine organisms: antioxidant activity of mycosporine-glycine" Comp. Biochem. Physiol., vol. 112B, No. 1, pp. 105-114, 1995.
Gao, Qunjie et al. "Microbial ultraviolet sunscreens" Nature Reviews:Microbiology vol. Nov. 9, 2011 pp. 791-802.
Gao, Qunjie et al. "An ATP-Grasp Ligase Involved in the Last Biosynthetic Step of the Iminomycosporine Shinorine in Nostoc punctiforme ATCC 29133" Journal of Bacteriology, Nov. 2011 pp. 5923-5928.

(Continued)

*Primary Examiner* — Robert B Mondesi
*Assistant Examiner* — Todd M Epstein
(74) *Attorney, Agent, or Firm* — Edwin S. Flores; Daniel J. Chalker; Chalker Flores, LLP

(57) ABSTRACT

The present disclosure relates to a microorganism for producing a mycosporine-like amino acid, and a method for producing a mycosporine-like amino acid using the microorganism.

The microorganism of the present disclosure shows an improved ability for producing a mycosporine-like amino acid and thus can be effectively used in the production of a mycosporine-like amino acid.

14 Claims, No Drawings
Specification includes a Sequence Listing.

(56) References Cited

OTHER PUBLICATIONS

Gorbushina, Anna A. et al. "Black fungal colonies as units of survival: hyphal mycosporines sythesized by rock-dwelling microcolonial fungi" Can. J. Bot. 81:131-138 (2003).

Hartmann, Anja et al. "Inhibition of Collagease by Mycosporine-like Amino Acids form Marine Sources" Planta Med. Jul. 2015; 81(10): 813-820.

Karentz, D. et al. "Survey of mycosporine-like amino acid compounds in Antarctic marine organisms: potential protection from ultraviolet exposure" Marine Biology 108, 157-166 (1991).

Katocg, Meenu et al. "Heterologous Production of Cyanobacterial Mycosporine-Like Amino Acids Mycosporine-Ornithine and Mycosporine-Lysine in *Escherichia coli*" Applied and Environmental Microbiology Oct. 2016, vol. 82 No. 20 pp. 6167-6173.

Liu, Xianglei et al. "Site-specific integration and constitutive expression of key genes into *Escherichia coli* chromosome increases shikimic acid yields" Enzyme and Microbial Technology 82 (2016) 96-104.

Nazifi, Ehsan et al. "Characterization of the chemical diversity of glycosylated mycosporine-like amino acids in the terrestrial cyanobacterium Nostoc commune" Journal of Photochemistry and Photobiology B: Biology 142 (2015) 154-168.

Oren, Aharon et al. "Mycosporinews and mycosporine-like amino acids: UV protectants or multipurpose secondary metabolites?" FEMS Microbiol Lett 269 (2007) 1-10.

Oren, Aharon "Mycosporine-Like Amino Acids as Osmotic Solutes in a Community of Halophilic Cyanobacteria" Geomicrobiology Journal, 14:231-240, 1997.

Rodrigues Rui T.L. et al. "One-Step Isothermal Assembly of DNA Fragments" Synthetic Biology, Methods in Molecular Biology, vol. 1073 (2013) pp. 43-47.

Shicks, J. Malcom et al. "Mycosporine-Like Amino Acids and Related Gadusols: Biosynthesis, Accumulation, and UV-Protective Functions in Aquatic Organisms" Annu. Rev. Physiol. 2022. 64:223-62.

Singh, Shailendra P. et al. "Genome mining of mycosporine-like amino acid (MAA) synthesizing and non-synthesizing cyanobacteria: A bioinformatics study" Genomics 95 (2010) 120-128.

Sinha, Rajeshwar P. et al. "Database on mycosporines and mycosporine-like amino acids (MAAs) in fungi, cyanobacteria, macroalgae, phytoplankton and animals" Journal of Photochemistry and Photobiology B: Biology 89 (2007) 29-35.

Waller, Ross F. et al. "Lateral Gene Transfer of a Multigene Region from Cyanobacteria to Dinoflagellates Resulting in a Novel Plastid-Targeted Fusion Protein" Mol. Biol. Evol. 23(7):1437-1443. 2006.

Extended European Search Report, EP 18846387.1 dated Mar. 25, 2021.

* cited by examiner

SEQUENCE LISTING

<160> NUMBER OF SEQ ID NOS: 104

<210> SEQ ID NO 1
<211> LENGTH: 6461
<212> TYPE: DNA
<213> ORGANISM: Anabaena variabilis ATCC29413

<400> SEQUENCE: 1

```
atgagtatcg tccaagcaaa gtttgaagct aaggaaacat cttttcatgt agaaggttac      60
gaaaagattg agtatgattt ggtgtatgta gatggtattt ttgaaatcca gaattctgca     120
ctagcagatg tatatcaagg ttttggacga tgcttggcga ttgtagatgc taacgtcagt     180
cggttgtatg gtaatcaaat tcaggcatat ttccagtatt atggtataga actgaggcta     240
tttcctatta ccattactga accagataag actattcaaa ctttcgagag agttatagat     300 gtcttttgcag atttcaaatt agtccgcaaa gaaccagtat tagtcgtggg tggcggttta     360
attacagatg ttgtcggctt tgcttgttct acatatcgtc gcagcagcaa ttacatccgc     420
attcctacta cattgattgg attaattgat gccagtgtag caattaaggt agcagttaat     480
catcgcaaac tgaaaaaccg tttgggtgct tatcatgctt ctcgcaaagt atttttagat     540
ttctccttgt tgcgtactct ccctacagac caagtacgta acgggatggc ggaattggta     600
aaaatcgctg tagtagcgca tcaagaagtt tttgaattgt tggagaagta cggcgaagaa     660
ttactacgta ctcattttgg caatatagat gcaactccag agattaaaga aatagcccat     720
cgtttgactt acaaagctat ccataagatg ttggaattgg aagttcccaa cctgcatgag     780
ttagacctag atagggtgat tgcttacggt cacacttgga gtcccacctt ggaacttgcg     840
cctcgtctac ccatgttcca cggacacgcc gttaatgtag atatggcttt ctcggcaacg     900
atcgccgccc gtagaggata tattacaatt gcagaacgcg atcgtatttt aggattaatg     960
agtcgcgttg gtctatccct cgaccatccc atgttggata tagatatttt gtggcgtggt    1020
actgaatcta tcacattaac tcgtgatggt ttgttaagag ctgctatgcc aaaacccatt    1080
ggtgattgtg tcttcgtcaa tgacctgaca agagaagaat tagcagccgc attagctgac    1140
cacaaagaac tttgtaccag ttatccccgt ggtggtgaag gtgtggatgt gtatcccgtt    1200
tatcaaaaag aattaatcgg gagtgttaaa taatgacttt tttgaattca aaatgcaaaa    1260
tactccacgg atacactgcg cgagcgcggt agcatttctg ttcgcggagc gtcccgtagg    1320
gaaagagaag gctacgcaaa taatcggaca ctaattgtct ttaattttga attttgaatt    1380
ttgaattttg aattggagcg aagcgacttg acaaatgtga ttgtccaacc aacagctaga    1440
cctgttacac cattgggaat tttaaccaag cagttagaag ccatagtcca agaggttaag    1500
```

```
caacatccag atttacctgg ggaattgata gcaaacatcc atcaggcttg gcgtttagcc    1560
gcaggtatag acccttattt ggaagaatgc accactccag aatctcctga actcgctgca    1620
ttggcaaaaa ccacagccac cgaagcctgg ggagaacact tccacggagg tacaaccgtc    1680
cgtcctctag aacaagagat gctttctggt catatcgaag acaaaccttt aaagatgttt    1740
gttcacatga ccaaagctaa aaaagtctta gaaattggga tgtttaccgg ttattcggcg    1800
ctggcgatgc cggaagcatt accagaggat ggactgcttg tggcttgtga agttgaccct    1860
tacgcggcgg aaattggaca gaaagccttt caacaatctc cccacggtgg aaagattcgt    1920
gtggaattgg atgcagcctt agcaactctt gataagttag cagaagctgg ggagtctttt    1980
gacttggtat ttatcgacgc agataaaaaa gagtatgtag cctatttcta caagttgcta    2040
ggtagcagtt tgttagcacc agatggcttt atttgtgtag ataacacctt attacaaggg    2100
gaagtttatc taccagcaga ggaacgtagc gtcaatggtg aagcgatcgc gcaatttaat    2160
catacagtag ctatagaccc ccgtgtagaa caggttttgt tgccgttgcg agatggttta    2220
acaattatcc gcagaataca accttaattg tccaatcgac tatggcacaa tcccttcccc    2280
tttcttccgc acctgctaca ccgtctcttc cttcccagac gaaaatagcc gcaattatcc    2340
aaaatatctg cactttggct tgttattac tagcattgcc cattaatgcc accattgttt    2400
ttatatcctt gttagtcttc cgaccgcaaa aggtcaaagc agcaaccccc caaccattc    2460 ttatcagtgg cggtaagatg accaaagctt tacaactagc aaggtcattc cacgcggctg    2520
gacatagagt tgtcttggtg gaaacccata aatactggtt gactggtcat cgttttttccc    2580 aagcagtgga taagttttac acagtccccg cacccaggga caatcccaa gcttacattc    2640 aggctttggt agatatcgtc aaacaagaaa acatcgatgt ttatattccc gtcaccagtc    2700
cagtgggtag ctactacgac tcattagcca aaccagagtt atcccattat tgcgaagtgt    2760
ttcactttga cgcagatatt acccaaatgt tggatgataa atttgcgttg acacaaaaag    2820
cgcgatcgct tggtttatca gtacccaaat cctttaaaat tacctcacca gaacaagtca    2880
tcaacttcga tttttctgga gagacacgta atacatcct caaaagcatt ccctacgact    2940
cagtgcggcg gttggactta accaaactcc cctgtgctac tccagaggaa acagcagcat    3000
tcgtcagaag tttgccaatt actcccgaaa aaccgtggat tatgcaggaa tttatccccg    3060
gtaaggaatt ctgcacccat agcaccgttc ggaatgggga actcagactg cattgctgtt    3120
gcgaatcttc agccttccaa gttaattatg agaatgtaaa taccccgcaa attaccgaat    3180
gggtacagca ttttgtcaag gaactgaaac tgacaggaca gatttccttt gactttatcc    3240
aagccgaaga cggaacagtt tacgccatcg agtgtaaccc ccgcacacat tcagcaatta    3300
ccacatttta cgaccacccc caggtagcag aagcgtactt gagtcaagca ccgacgactg    3360
aaaccataca accactaacg acaagcaagc ctacctattg gacttatcac gaagtttggc    3420
gtttaactgg tatccgttct ttcacccagt tgcaaagatg gctggggaat atttggcgcg    3480
ggactgatgc gatttatcag ccagatgacc ccttaccgtt tttgatggta catcattggc    3540
aaattcccct actgttattg aataatttgc gtcgtcttaa aggttggacg cggatagatt    3600
tcaatattgg gaagttggtg gaattggggg gagattagtt tttaaacgca gagggacgct    3660
gaggttagcg cagcgaaaag ttctggagga gggtttccct ccgtaggaaa cttttcaaga    3720
gagagggacg cggagtgtgt tttctctgcg tctctgcgtg agaaattttt tattattgag    3780
caaagttaga agatatgcag actatagatt ttaatattcg taagttactt gtagagtgga    3840
```

-continued

```
acgcgaccca cagagattat gatctttccc agagtttaca tgaactaatt gtagctcaag    3900
tagaacgaac acctgaggcg atcgctgtca cctttgacaa gcaacaacta acttatcaag    3960
aactaaatca taaagcaaac cagctaggac attatttaca acattagga gtccagccag    4020
aaaccctggt aggcgtttgt ttagaacgtt ccttagaaat ggttatctgt cttttaggaa    4080
tcctcaaagc tggggtgct  tatgttccta ttgaccctga atatcctcaa gaacgcatag    4140
cttatatgct agaagattct caggtgaagg tactactaac tcaagaaaaa ttactcaatc    4200
aaattcccca ccatcaagca caaactatct gtgtagatag ggaatgggag aaaatttcca    4260
cacaagctaa taccaatccc aaaagtaata taaaaacgga taatcttgct tatgtaattt    4320
acacctctgg ttccactggt aaaccaaaag gtgcaatgaa cacccacaaa ggtatctgta    4380
atcgcttatt gtggatgcag gaagcttatc aaatcgattc cacagatagc attttacaaa    4440
aaaccccctt tagttttgat gtttccgttt gggagttctt ttggactttta ttaactggcg    4500
cacgtttggt aatagccaaa ccaggcggac ataaagatag tgcttacctc atcgatttaa    4560
ttactcaaga acaaatcact acgttgcatt ttgtcccctc aatgctgcaa gtgtttttac    4620
aaaatcgcca tgtaagcaaa tgcagctctc taaaaagagt tatttgtagc ggtgaagctt    4680
tatctataga tttacaaaat agattttttcc agcatttgca atgtgaatta cataacctct    4740
atggcccgac agaagcagca attgatgtca catttggca atgtagaaaa gatagtaatt    4800
taaagagtgt acctattggt cgtcccattg ctaatactca aatttatatt cttgatgccg    4860
atttacaacc agtaaatatt ggtgtcactg gtgaaattta tattggtggt gtaggggttg    4920
ctcgtggtta tttgaataaa gaagaattga ccaaagaaaa atttattatt aatccctttc    4980
ccaattctga gtttaagcga ctttataaaa caggtgattt agctcgttat ttacccgatg    5040
gaaatattga atatcttggt agaacagatt atcaagtaaa aattcggggt tatagaattg    5100
aaattggcga gattgaaaat gttttatctt cacacccaca agtcagagaa gctgtagtca    5160
tagcgcggga tgataacgct caagaaaaac aaatcatcgc ttatattacc tataactcca    5220
tcaaacctca gcttgataat ctgcgtgatt tcctaaaagc aaggctacct gattttatga    5280
ttccagccgc ttttgtgatg ctggagcatc ttccttttaac tcccagtggt aaagtagacc    5340
gtaaggcatt acctaagcct gatttattta attatagtga acataattcc tatgtagcgc    5400
ctcggaatga agttgaagaa aaattagtac aaatctggtc gaatattctg catttaccta    5460
aagtaggtgt gacagaaaac ttttttcgcta ttggtggtaa ttccctcaaa gctctacatt    5520
taatttctca aattgaagag ttatttgcta aagagatatc cttagcaaca cttttaacaa    5580
atccagtaat tgcagattta gccaaggtta ttcaagcaaa caaccaaatc cataattcac    5640
ccctagttcc aattcaacca caaggtaagc agcagccttt cttttgtata catcctgctg    5700
gtggtcatgt tttatgctat tttaaaactcg cacaatatat aggaactgac caaccatttt    5760
atggcttaca agctcaagga ttttatggag atgaagcacc cttgacgcga gttgaagata    5820
tggctagtct ctacgtcaaa actattagag aatttcaacc ccaagggcct tatcgtgtcg    5880
gggggtggtc atttggtgga gtcgtagctt atgaagtagc acagcagtta catagacaag    5940
gacaagaagt atctttacta gcaatattag attcttacgt accgattctg ctggataaac    6000
aaaaacccat tgatgacgtt tatttagttg gtgttctctc cagagttttt ggcggtatgt    6060
ttggtcaaga taatctagtc acacctgaag aaatagaaaa tttaactgta gaagaaaaaa    6120
ttaattacat cattgataaa gcacggagcg ctagaatatt cccgcctggt gtagaacgtc    6180
aaaataatcg ccgtattctt gatgttttgg tgggaacttt aaaagcaact tattcctata    6240
```

-continued
taagacaacc atatccagga aaagtcactg tatttcgagc cagggaaaaa catattatgg 6300
ctcctgaccc gaccttagtt tgggtagaat tattttctgt aatggcggct caagaaatta 6360
<br>

agattattga tgtccctgga aaccattatt cgtttgttct agaaccccat gtacaggttt 6420
tagcacagcg tttacaagat tgtctggaaa ataattcata a 6461

<210> SEQ ID NO 2
<211> LENGTH: 2035
<212> TYPE: PRT
<213> ORGANISM: Anabaena variabilis ATCC29413

<400> SEQUENCE: 2

Met Ser Ile Val Gln Ala Lys Phe Glu Ala Lys Glu Thr Ser Phe His
1               5                   10                  15

Val Glu Gly Tyr Glu Lys Ile Glu Tyr Asp Leu Val Tyr Val Asp Gly
            20                  25                  30

Ile Phe Glu Ile Gln Asn Ser Ala Leu Ala Asp Val Tyr Gln Gly Phe
        35                  40                  45

Gly Arg Cys Leu Ala Ile Val Asp Ala Asn Val Ser Arg Leu Tyr Gly
    50                  55                  60

Asn Gln Ile Gln Ala Tyr Phe Gln Tyr Tyr Gly Ile Glu Leu Arg Leu
65                  70                  75                  80

Phe Pro Ile Thr Ile Thr Glu Pro Asp Lys Thr Ile Gln Thr Phe Glu
                85                  90                  95

Arg Val Ile Asp Val Phe Ala Asp Phe Lys Leu Val Arg Lys Glu Pro
            100                 105                 110

Val Leu Val Val Gly Gly Gly Leu Ile Thr Asp Val Val Gly Phe Ala
        115                 120                 125

Cys Ser Thr Tyr Arg Arg Ser Ser Asn Tyr Ile Arg Ile Pro Thr Thr
    130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
            180                 185                 190

Arg Asn Gly Met Ala Glu Leu Val Lys Ile Ala Val Val Ala His Gln
        195                 200                 205

Glu Val Phe Glu Leu Leu Glu Lys Tyr Gly Glu Glu Leu Leu Arg Thr
    210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
            260                 265                 270

Trp Ser Pro Thr Leu Glu Leu Ala Pro Arg Leu Pro Met Phe His Gly
        275                 280                 285

His Ala Val Asn Val Asp Met Ala Phe Ser Ala Thr Ile Ala Ala Arg
    290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

```
Leu Trp Arg Gly Thr Glu Ser Ile Thr Leu Thr Arg Asp Gly Leu Leu
            340                 345                 350

Arg Ala Ala Met Pro Lys Pro Ile Gly Asp Cys Val Phe Val Asn Asp
            355                 360                 365

Leu Thr Arg Glu Glu Leu Ala Ala Leu Ala Asp His Lys Glu Leu
    370                 375                 380

Cys Thr Ser Tyr Pro Arg Gly Glu Gly Val Asp Val Tyr Pro Val
385                 390                 395                 400

Tyr Gln Lys Glu Leu Ile Gly Ser Val Lys Leu Thr Asn Val Ile Val
                405                 410                 415

Gln Pro Thr Ala Arg Pro Val Thr Pro Leu Gly Ile Leu Thr Lys Gln
            420                 425                 430

Leu Glu Ala Ile Val Gln Glu Val Lys Gln His Pro Asp Leu Pro Gly
            435                 440                 445

Glu Leu Ile Ala Asn Ile His Gln Ala Trp Arg Leu Ala Ala Gly Ile
            450                 455                 460

Asp Pro Tyr Leu Glu Glu Cys Thr Thr Pro Glu Ser Pro Glu Leu Ala
465                 470                 475                 480

Ala Leu Ala Lys Thr Thr Ala Thr Glu Ala Trp Gly Glu His Phe His
                485                 490                 495

Gly Gly Thr Thr Val Arg Pro Leu Glu Gln Glu Met Leu Ser Gly His
            500                 505                 510

Ile Glu Gly Gln Thr Leu Lys Met Phe Val His Met Thr Lys Ala Lys
            515                 520                 525

Lys Val Leu Glu Ile Gly Met Phe Thr Gly Tyr Ser Ala Leu Ala Met
530                 535                 540

Ala Glu Ala Leu Pro Glu Asp Gly Leu Leu Val Ala Cys Glu Val Asp
545                 550                 555                 560

Pro Tyr Ala Ala Glu Ile Gly Gln Lys Ala Phe Gln Gln Ser Pro His
                565                 570                 575

Gly Gly Lys Ile Arg Val Glu Leu Asp Ala Ala Leu Ala Thr Leu Asp
            580                 585                 590

Lys Leu Ala Glu Ala Gly Glu Ser Phe Asp Leu Val Phe Ile Asp Ala
            595                 600                 605

Asp Lys Lys Glu Tyr Val Ala Tyr Phe His Lys Leu Leu Gly Ser Ser
    610                 615                 620

Leu Leu Ala Pro Asp Gly Phe Ile Cys Val Asp Asn Thr Leu Leu Gln
625                 630                 635                 640

Gly Glu Val Tyr Leu Pro Ala Glu Glu Arg Ser Val Asn Gly Glu Ala
                645                 650                 655

Ile Ala Gln Phe Asn His Thr Val Ala Ile Asp Pro Arg Val Glu Gln
            660                 665                 670

Val Leu Leu Pro Leu Arg Asp Gly Leu Thr Ile Ile Arg Arg Ile Gln
            675                 680                 685

Pro Met Ala Gln Ser Leu Pro Leu Ser Ser Ala Pro Ala Thr Pro Ser
    690                 695                 700

Leu Pro Ser Gln Thr Lys Ile Ala Ala Ile Gln Asn Ile Cys Thr
705                 710                 715                 720

Leu Ala Leu Leu Leu Leu Ala Leu Pro Ile Asn Ala Thr Ile Val Phe
                725                 730                 735

Ile Ser Leu Leu Val Phe Arg Pro Gln Lys Val Lys Ala Ala Asn Pro
            740                 745                 750
```

```
Gln Thr Ile Leu Ile Ser Gly Gly Lys Met Thr Lys Ala Leu Gln Leu
            755                 760                 765

Ala Arg Ser Phe His Ala Gly His Arg Val Val Leu Val Glu Thr
770                 775                 780

His Lys Tyr Trp Leu Thr Gly His Arg Phe Ser Gln Ala Val Asp Lys
785                 790                 795                 800

Phe Tyr Thr Val Pro Ala Pro Gln Asp Asn Pro Gln Ala Tyr Ile Gln
                    805                 810                 815

Ala Leu Val Asp Ile Val Lys Gln Glu Asn Ile Asp Val Tyr Ile Pro
            820                 825                 830

Val Thr Ser Pro Val Gly Ser Tyr Tyr Asp Ser Leu Ala Lys Pro Glu
            835                 840                 845

Leu Ser His Tyr Cys Glu Val Phe His Phe Asp Ala Asp Ile Thr Gln
            850                 855                 860

Met Leu Asp Asp Lys Phe Ala Leu Thr Gln Lys Ala Arg Ser Leu Gly
865                 870                 875                 880

Leu Ser Val Pro Lys Ser Phe Lys Ile Thr Ser Pro Glu Gln Val Ile
                    885                 890                 895

Asn Phe Asp Phe Ser Gly Glu Thr Arg Lys Tyr Ile Leu Lys Ser Ile
                900                 905                 910

Pro Tyr Asp Ser Val Arg Arg Leu Asp Leu Thr Lys Leu Pro Cys Ala
            915                 920                 925

Thr Pro Glu Glu Thr Ala Ala Phe Val Arg Ser Leu Pro Ile Thr Pro
            930                 935                 940

Glu Lys Pro Trp Ile Met Gln Glu Phe Ile Pro Gly Lys Glu Phe Cys
945                 950                 955                 960

Thr His Ser Thr Val Arg Asn Gly Glu Leu Arg Leu His Cys Cys Cys
                    965                 970                 975

Glu Ser Ser Ala Phe Gln Val Asn Tyr Glu Asn Val Asn Asn Pro Gln
                980                 985                 990

Ile Thr Glu Trp Val Gln His Phe  Val Lys Glu Leu Lys  Leu Thr Gly
            995                 1000                1005

Gln Ile  Ser Phe Asp Phe Ile  Gln Ala Glu Asp Gly  Thr Val Tyr
     1010                 1015                1020

Ala Ile  Glu Cys Asn Pro Arg  Thr His Ser Ala Ile  Thr Thr Phe
     1025                1030                 1035

Tyr Asp His Pro Gln Val Ala  Glu Ala Tyr Leu Ser  Gln Ala Pro
     1040                1045                 1050

Thr Thr  Glu Thr Ile Gln Pro  Leu Thr Thr Ser Lys  Pro Thr Tyr
     1055                1060                 1065

Trp Thr Tyr His Glu Val Trp  Arg Leu Thr Gly Ile  Arg Ser Phe
     1070                1075                 1080

Thr Gln  Leu Gln Arg Trp Leu  Gly Asn Ile Trp Arg  Gly Thr Asp
     1085                1090                 1095

Ala Ile  Tyr Gln Pro Asp Asp  Pro Leu Pro Phe Leu  Met Val His
     1100                1105                 1110

His Trp  Gln Ile Pro Leu Leu  Leu Leu Asn Asn Leu  Arg Arg Leu
     1115                1120                 1125

Lys Gly  Trp Thr Arg Ile Asp  Phe Asn Ile Gly Lys  Leu Val Glu
     1130                1135                 1140

Leu Gly  Gly Asp Met Gln Thr  Ile Asp Phe Asn Ile  Arg Lys Leu
     1145                1150                 1155

Leu Val  Glu Trp Asn Ala Thr  His Arg Asp Tyr Asp  Leu Ser Gln
```

-continued

```
              1160                1165                1170

Ser  Leu  His  Glu  Leu  Ile  Val  Ala  Gln  Val  Arg  Thr  Pro  Glu
     1175                1180                1185

Ala  Ile  Ala  Val  Thr  Phe  Asp  Lys  Gln  Gln  Leu  Thr  Tyr  Gln  Glu
     1190                1195                1200

Leu  Asn  His  Lys  Ala  Asn  Gln  Leu  Gly  His  Tyr  Leu  Gln  Thr  Leu
     1205                1210                1215

Gly  Val  Gln  Pro  Glu  Thr  Leu  Val  Gly  Val  Cys  Leu  Glu  Arg  Ser
     1220                1225                1230

Leu  Glu  Met  Val  Ile  Cys  Leu  Leu  Gly  Ile  Leu  Lys  Ala  Gly  Gly
     1235                1240                1245

Ala  Tyr  Val  Pro  Ile  Asp  Pro  Glu  Tyr  Pro  Gln  Glu  Arg  Ile  Ala
     1250                1255                1260

Tyr  Met  Leu  Glu  Asp  Ser  Gln  Val  Lys  Val  Leu  Leu  Thr  Gln  Glu
     1265                1270                1275

Lys  Leu  Leu  Asn  Gln  Ile  Pro  His  His  Gln  Ala  Gln  Thr  Ile  Cys
     1280                1285                1290

Val  Asp  Arg  Glu  Trp  Glu  Lys  Ile  Ser  Thr  Gln  Ala  Asn  Thr  Asn
     1295                1300                1305

Pro  Lys  Ser  Asn  Ile  Lys  Thr  Asp  Asn  Leu  Ala  Tyr  Val  Ile  Tyr
     1310                1315                1320

Thr  Ser  Gly  Ser  Thr  Gly  Lys  Pro  Lys  Gly  Ala  Met  Asn  Thr  His
     1325                1330                1335

Lys  Gly  Ile  Cys  Asn  Arg  Leu  Leu  Trp  Met  Gln  Glu  Ala  Tyr  Gln
     1340                1345                1350

Ile  Asp  Ser  Thr  Asp  Ser  Ile  Leu  Gln  Lys  Thr  Pro  Phe  Ser  Phe
     1355                1360                1365

Asp  Val  Ser  Val  Trp  Glu  Phe  Phe  Trp  Thr  Leu  Leu  Thr  Gly  Ala
     1370                1375                1380

Arg  Leu  Val  Ile  Ala  Lys  Pro  Gly  Gly  His  Lys  Asp  Ser  Ala  Tyr
     1385                1390                1395

Leu  Ile  Asp  Leu  Ile  Thr  Gln  Glu  Gln  Ile  Thr  Thr  Leu  His  Phe
     1400                1405                1410

Val  Pro  Ser  Met  Leu  Gln  Val  Phe  Leu  Gln  Asn  Arg  His  Val  Ser
     1415                1420                1425

Lys  Cys  Ser  Ser  Leu  Lys  Arg  Val  Ile  Cys  Ser  Gly  Glu  Ala  Leu
     1430                1435                1440

Ser  Ile  Asp  Leu  Gln  Asn  Arg  Phe  Phe  Gln  His  Leu  Gln  Cys  Glu
     1445                1450                1455

Leu  His  Asn  Leu  Tyr  Gly  Pro  Thr  Glu  Ala  Ala  Ile  Asp  Val  Thr
     1460                1465                1470

Phe  Trp  Gln  Cys  Arg  Lys  Asp  Ser  Asn  Leu  Lys  Ser  Val  Pro  Ile
     1475                1480                1485

Gly  Arg  Pro  Ile  Ala  Asn  Thr  Gln  Ile  Tyr  Ile  Leu  Asp  Ala  Asp
     1490                1495                1500

Leu  Gln  Pro  Val  Asn  Ile  Gly  Val  Thr  Gly  Glu  Ile  Tyr  Ile  Gly
     1505                1510                1515

Gly  Val  Gly  Val  Ala  Arg  Gly  Tyr  Leu  Asn  Lys  Glu  Glu  Leu  Thr
     1520                1525                1530

Lys  Glu  Lys  Phe  Ile  Ile  Asn  Pro  Phe  Pro  Asn  Ser  Glu  Phe  Lys
     1535                1540                1545

Arg  Leu  Tyr  Lys  Thr  Gly  Asp  Leu  Ala  Arg  Tyr  Leu  Pro  Asp  Gly
     1550                1555                1560
```

```
Asn Ile Glu Tyr Leu Gly Arg Thr Asp Tyr Gln Val Lys Ile Arg
    1565                1570                1575

Gly Tyr Arg Ile Glu Ile Gly Glu Ile Glu Asn Val Leu Ser Ser
    1580                1585                1590

His Pro Gln Val Arg Glu Ala Val Val Ile Ala Arg Asp Asp Asn
    1595                1600                1605

Ala Gln Glu Lys Gln Ile Ile Ala Tyr Ile Thr Tyr Asn Ser Ile
    1610                1615                1620

Lys Pro Gln Leu Asp Asn Leu Arg Asp Phe Leu Lys Ala Arg Leu
    1625                1630                1635

Pro Asp Phe Met Ile Pro Ala Ala Phe Val Met Leu Glu His Leu
    1640                1645                1650

Pro Leu Thr Pro Ser Gly Lys Val Asp Arg Lys Ala Leu Pro Lys
    1655                1660                1665

Pro Asp Leu Phe Asn Tyr Ser Glu His Asn Ser Tyr Val Ala Pro
    1670                1675                1680

Arg Asn Glu Val Glu Glu Lys Leu Val Gln Ile Trp Ser Asn Ile
    1685                1690                1695

Leu His Leu Pro Lys Val Gly Val Thr Glu Asn Phe Phe Ala Ile
    1700                1705                1710

Gly Gly Asn Ser Leu Lys Ala Leu His Leu Ile Ser Gln Ile Glu
    1715                1720                1725

Glu Leu Phe Ala Lys Glu Ile Ser Leu Ala Thr Leu Leu Thr Asn
    1730                1735                1740

Pro Val Ile Ala Asp Leu Ala Lys Val Ile Gln Ala Asn Asn Gln
    1745                1750                1755

Ile His Asn Ser Pro Leu Val Pro Ile Gln Pro Gln Gly Lys Gln
    1760                1765                1770

Gln Pro Phe Phe Cys Ile His Pro Ala Gly Gly His Val Leu Cys
    1775                1780                1785

Tyr Phe Lys Leu Ala Gln Tyr Ile Gly Thr Asp Gln Pro Phe Tyr
    1790                1795                1800

Gly Leu Gln Ala Gln Gly Phe Tyr Gly Asp Glu Ala Pro Leu Thr
    1805                1810                1815

Arg Val Glu Asp Met Ala Ser Leu Tyr Val Lys Thr Ile Arg Glu
    1820                1825                1830

Phe Gln Pro Gln Gly Pro Tyr Arg Val Gly Gly Trp Ser Phe Gly
    1835                1840                1845

Gly Val Val Ala Tyr Glu Val Ala Gln Gln Leu His Arg Gln Gly
    1850                1855                1860

Gln Glu Val Ser Leu Leu Ala Ile Leu Asp Ser Tyr Val Pro Ile
    1865                1870                1875

Leu Leu Asp Lys Gln Lys Pro Ile Asp Asp Val Tyr Leu Val Gly
    1880                1885                1890

Val Leu Ser Arg Val Phe Gly Gly Met Phe Gly Gln Asp Asn Leu
    1895                1900                1905

Val Thr Pro Glu Glu Ile Glu Asn Leu Thr Val Glu Glu Lys Ile
    1910                1915                1920

Asn Tyr Ile Ile Asp Lys Ala Arg Ser Ala Arg Ile Phe Pro Pro
    1925                1930                1935

Gly Val Glu Arg Gln Asn Asn Arg Arg Ile Leu Asp Val Leu Val
    1940                1945                1950
```

```
Gly Thr Leu Lys Ala Thr Tyr Ser Tyr Ile Arg Gln Pro Tyr Pro
1955                1960                1965

Gly Lys Val Thr Val Phe Arg Ala Arg Glu Lys His Ile Met Ala
1970                1975                1980

Pro Asp Pro Thr Leu Val Trp Val Glu Leu Phe Ser Val Met Ala
1985                1990                1995

Ala Gln Glu Ile Lys Ile Ile Asp Val Pro Gly Asn His Tyr Ser
2000                2005                2010

Phe Val Leu Glu Pro His Val Gln Val Leu Ala Gln Arg Leu Gln
2015                2020                2025

Asp Cys Leu Glu Asn Asn Ser
2030                2035

<210> SEQ ID NO 3
<211> LENGTH: 4528
<212> TYPE: DNA
<213> ORGANISM: Nostoc punctiforme ATCC29133

<400> SEQUENCE: 3
atgagtaatg ttcaagcatc gtttgaagca acggaagctg aattccgcgt ggaaggttac      60
gaaaaaattg agtttagtct tgtctatgta aatggtgcat ttgatatcag taacagagaa     120
attgcagaca gctatgagaa gtttggccgt tgtctgactg tgattgatgc taatgtcaac     180
agattatatg caagcaaat caagtcatat tttagacact atggtattga tctgaccgta     240
gttcccattg tgattactga gcctactaaa acccttgcaa cctttgagaa aattgttgat     300 gcttttctg actttggttt aatccgcaag gaaccagtat tagtagtggg tggtggttta     360
accactgatg tagctgggtt tgcgtgtgct gcttaccgtc gtaagagtaa ctatattcgg     420
gttccgacaa cgctgattgg tctgattgat gcagtgtag cgattaaggt tgcagtcaac     480
catcgcaagt taaaaaatcg cttgggtgca tatcatgctc ctttgaaagt catcctcgat     540
ttctccttct tgcaaacatt accaacggct caagttcgta atgggatggc agagttggtc     600
aaaattgctg ttgtggcgaa ctctgaagtc tttgaattgt tgtatgaata tggcgaagag     660
ttgctttcca ctcactttgg atatgtgaat ggtacaaagg aactgaaagc gatcgcacat     720
aaactcaatt acgaggcaat aaaaactatg ctggagttgg aaactccaaa cttgcatgag     780
ttagacctcg atcgcgtcat tgcctacggt cacacttgga gtccgacctt agaattagct     840
ccgatgatac cgttgtttca cggtcatgcc gtcaatatag acatggcttt gtctgcaact     900
attgcggcaa gacgtggcta cattacatca ggagaacgcg atcgcatttt gagcttgatg     960
agtcgtatag gtttatcaat cgatcatcct ctactagatg gcgatttgct ctggtatgct    1020
acccaatcta ttagcttgac gcgagacggg aaacaacgcg cagctatgcc taaacccatt    1080
ggtgagtgct tctttgtcaa cgatttcacc cgtgaagaac tagatgcagc tttagctgaa    1140
cacaaacgtc tgtgtgctac atacctcgt ggtggagatg gcattgacgc ttacatagaa    1200
actcaagaag aatccaaact attgggagtg tgaaaacatg accagtattt taggacgaga    1260
taccgcaaga ccaataacgc cacatagcat tctggtagca cagctacaaa aaaccctcag    1320
aatggcagag gaaagtaata ttccttcaga gatactgact tctctgcgcc aagggttgca    1380
attagcagca ggtttagatc cctatctgga tgattgcact accctgaat cgaccgcatt    1440 gacagcacta gcgcagaaga caagcattga agactggagt aaacgcttca gtgatggtga    1500
aacagtgcgt caattagagc aagaaatgct ctcaggacat cttgaaggac aaacactaaa    1560
gatgtttgtg catatcacta aggctaaaag catcctagaa gtgggaatgt tcacaggata    1620
```

```
ttcagctttg gcaatggcag aggcgttacc agatgatggg cgactgattg cttgtgaagt    1680
agactcctat gtggccgagt ttgctcaaac ttgctttcaa gagtctcccc acggccgcaa    1740
gattgttgta gaagtggcac ctgcactaga gacgctgcac aagctggtgg ctaaaaaga    1800 atcctttgat ctgatcttca ttgatgcgga taaaaaggag tatatagaat acttccaaat    1860
tatcttggat agccatttac tagctcccga cggattaatc tgtgtagata atactttgtt    1920
gcaaggacaa gtttacctgc catcagaaca gcgtacagcc aatggtgaag cgatcgctca    1980
attcaaccgc attgtcgccg cagatcctcg tgtagagcaa gttctgttac ccatacgaga    2040
tggtataacc ctgattagac gcttggtata agcggccgcg agctcctcga gatggcacaa    2100
tcaatctctt tatctcttcc tcaatccaca acgccatcaa agggtgtgag ctaaaaata    2160 gcagctctac tgaagactat cgggactcta atactactgc tgatagcctt gccgcttaat    2220
gctttgatag tattgatatc tctgatgtgt aggccgttta caaaaaaacc tgccgtagcc    2280
actcatcccc agaatatctt ggtcagtggc ggcaaaatga ccaaagcatt gcaacttgcc    2340
cgctccttcc atgcagccgg acacagagtt attctgattg aaggtcataa atactggtta    2400
tcagggcata gattctcaaa ttctgtgagt cgttttttata cagttcctgc accacaagac    2460
gacccagaag gctataccca agcgctattg gaaattgtca acgagagaa gattgacgtt    2520 tatgtacccg tatgcagccc tgtagctagt tattacgact cttggcaaa gtctgcacta    2580 tcagaatatt gtgaggtttt tcactttgat gctgatataa ccaagatgct ggatgataaa    2640
tttgccttta ccgatcgggc gcgatcgctt ggtttatcag ccccgaaatc ttttaaaatt    2700
accgatcctg aacaagttat caacttcgat tttagtaaag agacgcgcaa atatattctt    2760
aagagtattt cttacgactc agttcgccgc ttaaatttaa ccaaacttcc ttgtgatacc    2820
ccagaagaga cagcagcgtt tgtcaagagt ttacccatca gcccagaaaa accttggatt    2880
atgcaagaat ttattcctgg gaagaatta tgcacccata gcacagtccg agacggcgaa    2940
ttaaggttgc attgctgttc aaattcttca gcgtttcaga ttaactatga aaatgtcgaa    3000
aatccccaaa ttcaagaatg ggtacaacat ttcgtcaaaa gtttacggct gactggacaa    3060
atatctcttg actttatcca agctgaagat ggtacagctt atgccattga atgtaatcct    3120
cgcacccatt cggcgatcac aatgttctac aatcacccag gtgttgcaga agcctatctt    3180
ggtaaaactc ctctagctgc acctttggaa cctcttgcag atagcaagcc cacttactgg    3240
atatatcacg aaatctggcg attgactggg attcgctctg acaacaatt acaaacttgg    3300 tttgggagat tagtcagagg tacagatgcc atttatcgcc tggacgatcc gataccattt    3360
ttaactttgc accattggca gattacttta cttttgctac aaaatttgca acgactcaaa    3420
ggttgggtaa agatcgattt taatatcggt aaactcgtgg aattaggggg cgactaaaaa    3480
catgccagta cttaatatcc ttcatttagt tgggtctgca cacgataagt tttactgtga    3540
tttatcacgt ctttatgccc aagactgttt agctgcaaca gcagatccat cgctttataa    3600
ctttcaaatt gcatatatca cacccgatcg gcagtggcga tttcctgact ctctcagtcg    3660
agaagatatt gctcttacca aaccgattcc tgtgtttgat gccatacaat ttctaacagg    3720
ccaaaacatt gacatgatgt taccacaaat gttttgtatt cctggaatga ctcagtaccg    3780
tgccctattc gatctgctca agatccctta tataggaaat accccagata ttatggcgat    3840
cgcggcccac aaagccagag ccaaagcaat tgtcgaagca gcaggggtaa aagtgcctcg    3900
tggagaattg cttcgccaag gagatattcc aacaattaca cctccagcag tcgtcaaacc    3960
```

-continued

```
tgtaagttct gacaactctt taggagtagt cttagttaaa gatgtgactg aatatgatgc    4020
tgccttaaag aaagcatttg aatatgcttc ggaggtcatc gtagaagcat tcatcgaact    4080
tggtcgagaa gtcagatgcg gcatcattgt aaaagacggt gagctaatag gtttacccct    4140
tgaagagtat ctggtagacc cacacgataa acctatccgt aactatgctg ataaactcca    4200
acaaactgac gatggcgact tgcatttgac tgctaaagat aatatcaagg cttggatttt    4260
agaccctaac gacccaatca cccaaaaggt tcagcaagtg gctaaaaggt gtcatcaggc    4320
tttgggttgt cgccactaca gtttatttga cttccgaatc gatccaaagg gacaaccttg    4380
gttcttagaa gctggattat attgttcttt tgcccccaaa agtgtgattt cttctatggc    4440
gaaagcagcc ggaatccctc taatgattt attaataacc gctattaatg aaacattggg    4500
tagtaataaa aaggtgttac aaaattga                                        4528
```

<210> SEQ ID NO 4
<211> LENGTH: 1496
<212> TYPE: PRT
<213> ORGANISM: Nostoc punctiforme ATCC29133

<400> SEQUENCE: 4

```
Met Ser Asn Val Gln Ala Ser Phe Glu Ala Thr Glu Ala Glu Phe Arg
1               5                   10                  15

Val Glu Gly Tyr Glu Lys Ile Glu Phe Ser Leu Val Tyr Val Asn Gly
            20                  25                  30

Ala Phe Asp Ile Ser Asn Arg Glu Ile Ala Asp Ser Tyr Glu Lys Phe
        35                  40                  45

Gly Arg Cys Leu Thr Val Ile Asp Ala Asn Val Asn Arg Leu Tyr Gly
    50                  55                  60

Lys Gln Ile Lys Ser Tyr Phe Arg His Tyr Gly Ile Asp Leu Thr Val
65                  70                  75                  80

Val Pro Ile Val Ile Thr Glu Pro Thr Lys Thr Leu Ala Thr Phe Glu
                85                  90                  95

Lys Ile Val Asp Ala Phe Ser Asp Phe Gly Leu Ile Arg Lys Glu Pro
            100                 105                 110

Val Leu Val Val Gly Gly Gly Leu Thr Thr Asp Val Ala Gly Phe Ala
        115                 120                 125

Cys Ala Ala Tyr Arg Arg Lys Ser Asn Tyr Ile Arg Val Pro Thr Thr
    130                 135                 140

Leu Ile Gly Leu Ile Asp Ala Gly Val Ala Ile Lys Val Ala Val Asn
145                 150                 155                 160

His Arg Lys Leu Lys Asn Arg Leu Gly Ala Tyr His Ala Pro Leu Lys
                165                 170                 175

Val Ile Leu Asp Phe Ser Phe Leu Gln Thr Leu Pro Thr Ala Gln Val
            180                 185                 190

Arg Asn Gly Met Ala Glu Leu Val Lys Ile Ala Val Ala Asn Ser
        195                 200                 205

Glu Val Phe Glu Leu Leu Tyr Glu Tyr Gly Glu Leu Leu Ser Thr
    210                 215                 220

His Phe Gly Tyr Val Asn Gly Thr Lys Glu Leu Lys Ala Ile Ala His
225                 230                 235                 240

Lys Leu Asn Tyr Glu Ala Ile Lys Thr Met Leu Glu Leu Glu Thr Pro
                245                 250                 255

Asn Leu His Glu Leu Asp Leu Asp Arg Val Ile Ala Tyr Gly His Thr
            260                 265                 270
```

-continued

```
Trp Ser Pro Thr Leu Glu Leu Ala Pro Met Ile Pro Leu Phe His Gly
            275                 280                 285
His Ala Val Asn Ile Asp Met Ala Leu Ser Ala Thr Ile Ala Ala Arg
        290                 295                 300
Arg Gly Tyr Ile Thr Ser Gly Glu Arg Asp Arg Ile Leu Ser Leu Met
305                 310                 315                 320
Ser Arg Ile Gly Leu Ser Ile Asp His Pro Leu Leu Asp Gly Asp Leu
                325                 330                 335
Leu Trp Tyr Ala Thr Gln Ser Ile Ser Leu Thr Arg Asp Gly Lys Gln
            340                 345                 350
Arg Ala Ala Met Pro Lys Pro Ile Gly Glu Cys Phe Phe Val Asn Asp
        355                 360                 365
Phe Thr Arg Glu Glu Leu Asp Ala Ala Leu Ala Glu His Lys Arg Leu
370                 375                 380
Cys Ala Thr Tyr Pro Arg Gly Gly Asp Gly Ile Asp Ala Tyr Ile Glu
385                 390                 395                 400
Thr Gln Glu Glu Ser Lys Leu Leu Gly Val Met Thr Ser Ile Leu Gly
                405                 410                 415
Arg Asp Thr Ala Arg Pro Ile Thr Pro His Ser Ile Leu Val Ala Gln
            420                 425                 430
Leu Gln Lys Thr Leu Arg Met Ala Glu Glu Ser Asn Ile Pro Ser Glu
        435                 440                 445
Ile Leu Thr Ser Leu Arg Gln Gly Leu Gln Leu Ala Ala Gly Leu Asp
        450                 455                 460
Pro Tyr Leu Asp Asp Cys Thr Thr Pro Glu Ser Thr Ala Leu Thr Ala
465                 470                 475                 480
Leu Ala Gln Lys Thr Ser Ile Glu Asp Trp Ser Lys Arg Phe Ser Asp
                485                 490                 495
Gly Glu Thr Val Arg Gln Leu Glu Gln Glu Met Leu Ser Gly His Leu
            500                 505                 510
Glu Gly Gln Thr Leu Lys Met Phe Val His Ile Thr Lys Ala Lys Ser
        515                 520                 525
Ile Leu Glu Val Gly Met Phe Thr Gly Tyr Ser Ala Leu Ala Met Ala
        530                 535                 540
Glu Ala Leu Pro Asp Asp Gly Arg Leu Ile Ala Cys Glu Val Asp Ser
545                 550                 555                 560
Tyr Val Ala Glu Phe Ala Gln Thr Cys Phe Gln Glu Ser Pro His Gly
                565                 570                 575
Arg Lys Ile Val Val Glu Val Ala Pro Ala Leu Glu Thr Leu His Lys
            580                 585                 590
Leu Val Ala Lys Lys Glu Ser Phe Asp Leu Ile Phe Ile Asp Ala Asp
        595                 600                 605
Lys Lys Glu Tyr Ile Glu Tyr Phe Gln Ile Ile Leu Asp Ser His Leu
610                 615                 620
Leu Ala Pro Asp Gly Leu Ile Cys Val Asp Asn Thr Leu Leu Gln Gly
625                 630                 635                 640
Gln Val Tyr Leu Pro Ser Glu Gln Arg Thr Ala Asn Gly Glu Ala Ile
                645                 650                 655
Ala Gln Phe Asn Arg Ile Val Ala Ala Asp Pro Arg Val Glu Gln Val
            660                 665                 670
Leu Leu Pro Ile Arg Asp Gly Ile Thr Leu Ile Arg Arg Leu Val Met
        675                 680                 685
Ala Gln Ser Ile Ser Leu Ser Leu Pro Gln Ser Thr Thr Pro Ser Lys
```

-continued

```
            690                 695                 700
Gly Val Arg Leu Lys Ile Ala Ala Leu Leu Lys Thr Ile Gly Thr Leu
705                 710                 715                 720

Ile Leu Leu Leu Ile Ala Leu Pro Leu Asn Ala Leu Ile Val Leu Ile
                725                 730                 735

Ser Leu Met Cys Arg Pro Phe Thr Lys Lys Pro Ala Val Ala Thr His
                740                 745                 750

Pro Gln Asn Ile Leu Val Ser Gly Gly Lys Met Thr Lys Ala Leu Gln
                755                 760                 765

Leu Ala Arg Ser Phe His Ala Ala Gly His Arg Val Ile Leu Ile Glu
                770                 775                 780

Gly His Lys Tyr Trp Leu Ser Gly His Arg Phe Ser Asn Ser Val Ser
785                 790                 795                 800

Arg Phe Tyr Thr Val Pro Ala Pro Gln Asp Asp Pro Glu Gly Tyr Thr
                805                 810                 815

Gln Ala Leu Leu Glu Ile Val Lys Arg Glu Lys Ile Asp Val Tyr Val
                820                 825                 830

Pro Val Cys Ser Pro Val Ala Ser Tyr Tyr Asp Ser Leu Ala Lys Ser
                835                 840                 845

Ala Leu Ser Glu Tyr Cys Glu Val Phe His Phe Asp Ala Asp Ile Thr
                850                 855                 860

Lys Met Leu Asp Asp Lys Phe Ala Phe Thr Asp Arg Ala Arg Ser Leu
865                 870                 875                 880

Gly Leu Ser Ala Pro Lys Ser Phe Lys Ile Thr Asp Pro Glu Gln Val
                885                 890                 895

Ile Asn Phe Asp Phe Ser Lys Glu Thr Arg Lys Tyr Ile Leu Lys Ser
                900                 905                 910

Ile Ser Tyr Asp Ser Val Arg Arg Leu Asn Leu Thr Lys Leu Pro Cys
                915                 920                 925

Asp Thr Pro Glu Glu Thr Ala Ala Phe Val Lys Ser Leu Pro Ile Ser
930                 935                 940

Pro Glu Lys Pro Trp Ile Met Gln Glu Phe Ile Pro Gly Lys Glu Leu
945                 950                 955                 960

Cys Thr His Ser Thr Val Arg Asp Gly Glu Leu Arg Leu His Cys Cys
                965                 970                 975

Ser Asn Ser Ser Ala Phe Gln Ile Asn Tyr Glu Asn Val Glu Asn Pro
                980                 985                 990

Gln Ile Gln Glu Trp Val Gln His Phe Val Lys Ser Leu Arg Leu Thr
                995                 1000                1005

Gly Gln Ile Ser Leu Asp Phe Ile Gln Ala Glu Asp Gly Thr Ala
1010                1015                1020

Tyr Ala Ile Glu Cys Asn Pro Arg Thr His Ser Ala Ile Thr Met
1025                1030                1035

Phe Tyr Asn His Pro Gly Val Ala Glu Ala Tyr Leu Gly Lys Thr
1040                1045                1050

Pro Leu Ala Ala Pro Leu Glu Pro Leu Ala Asp Ser Lys Pro Thr
1055                1060                1065

Tyr Trp Ile Tyr His Glu Ile Trp Arg Leu Thr Gly Ile Arg Ser
1070                1075                1080

Gly Gln Gln Leu Gln Thr Trp Phe Gly Arg Leu Val Arg Gly Thr
1085                1090                1095

Asp Ala Ile Tyr Arg Leu Asp Asp Pro Ile Pro Phe Leu Thr Leu
1100                1105                1110
```

-continued

His His Trp Gln Ile Thr Leu Leu Leu Leu Gln Asn Leu Gln Arg
1115                1120                1125

Leu Lys Gly Trp Val Lys Ile Asp Phe Asn Ile Gly Lys Leu Val
1130                1135                1140

Glu Leu Gly Gly Asp Met Pro Val Leu Asn Ile Leu His Leu Val
1145                1150                1155

Gly Ser Ala His Asp Lys Phe Tyr Cys Asp Leu Ser Arg Leu Tyr
1160                1165                1170

Ala Gln Asp Cys Leu Ala Ala Thr Ala Asp Pro Ser Leu Tyr Asn
1175                1180                1185

Phe Gln Ile Ala Tyr Ile Thr Pro Asp Arg Gln Trp Arg Phe Pro
1190                1195                1200

Asp Ser Leu Ser Arg Glu Asp Ile Ala Leu Thr Lys Pro Ile Pro
1205                1210                1215

Val Phe Asp Ala Ile Gln Phe Leu Thr Gly Gln Asn Ile Asp Met
1220                1225                1230

Met Leu Pro Gln Met Phe Cys Ile Pro Gly Met Thr Gln Tyr Arg
1235                1240                1245

Ala Leu Phe Asp Leu Leu Lys Ile Pro Tyr Ile Gly Asn Thr Pro
1250                1255                1260

Asp Ile Met Ala Ile Ala Ala His Lys Ala Arg Ala Lys Ala Ile
1265                1270                1275

Val Glu Ala Ala Gly Val Lys Val Pro Arg Gly Glu Leu Leu Arg
1280                1285                1290

Gln Gly Asp Ile Pro Thr Ile Thr Pro Pro Ala Val Val Lys Pro
1295                1300                1305

Val Ser Ser Asp Asn Ser Leu Gly Val Val Leu Val Lys Asp Val
1310                1315                1320

Thr Glu Tyr Asp Ala Ala Leu Lys Lys Ala Phe Glu Tyr Ala Ser
1325                1330                1335

Glu Val Ile Val Glu Ala Phe Ile Glu Leu Gly Arg Glu Val Arg
1340                1345                1350

Cys Gly Ile Ile Val Lys Asp Gly Glu Leu Ile Gly Leu Pro Leu
1355                1360                1365

Glu Glu Tyr Leu Val Asp Pro His Asp Lys Pro Ile Arg Asn Tyr
1370                1375                1380

Ala Asp Lys Leu Gln Gln Thr Asp Asp Gly Asp Leu His Leu Thr
1385                1390                1395

Ala Lys Asp Asn Ile Lys Ala Trp Ile Leu Asp Pro Asn Asp Pro
1400                1405                1410

Ile Thr Gln Lys Val Gln Gln Val Ala Lys Arg Cys His Gln Ala
1415                1420                1425

Leu Gly Cys Arg His Tyr Ser Leu Phe Asp Phe Arg Ile Asp Pro
1430                1435                1440

Lys Gly Gln Pro Trp Phe Leu Glu Ala Gly Leu Tyr Cys Ser Phe
1445                1450                1455

Ala Pro Lys Ser Val Ile Ser Ser Met Ala Lys Ala Ala Gly Ile
1460                1465                1470

Pro Leu Asn Asp Leu Leu Ile Thr Ala Ile Asn Glu Thr Leu Gly
1475                1480                1485

Ser Asn Lys Lys Val Leu Gln Asn
1490                1495

<210> SEQ ID NO 5
<211> LENGTH: 45
<212> TYPE: DNA
<213> ORGANISM: Artificial Sequence
<220> FEATURE:
<223> OTHER INFORMATION: Forward primerfor Ava_ABCD

<400> SEQUENCE: 5
acaatttcac acaggaaaga tatcatgagt atcgtccaag caaag            45

<210> SEQ ID NO 6
<211> LENGTH: 45
<212> TYPE: DNA
<213> ORGANISM: Artificial Sequence
<220> FEATURE:
<223> OTHER INFORMATION: Reverse primer for Ava_ABCD

<400> SEQUENCE: 6
ctcatccgcc aaaacagctc tagattatga attattttcc agaca            45

<210> SEQ ID NO 7
<211> LENGTH: 31
<212> TYPE: DNA
<213> ORGANISM: Artificial Sequence
<220> FEATURE:
<223> OTHER INFORMATION: Forward primer for Npr_ABCD

<400> SEQUENCE: 7
gatcgatatc atgagtaatg ttcaagcatc g                           31

<210> SEQ ID NO 8
<211> LENGTH: 36
<212> TYPE: DNA
<213> ORGANISM: Artificial Sequence
<220> FEATURE:
<223> OTHER INFORMATION: Reverse primer for Npr_ABCD

<400> SEQUENCE: 8
gatctctaga tcaattttgt aacacctttt tattac                      36

<210> SEQ ID NO 9
<211> LENGTH: 71
<212> TYPE: DNA
<213> ORGANISM: Artificial Sequence
<220> FEATURE:
<223> OTHER INFORMATION: Forward primer for aroD deletion cassette

<400> SEQUENCE: 9
tcatggggtt cggtgcctga caggctgacc gcgtgcagaa agggtaaaaa gctggagctg    60
cttcgaagtt c                                                         71

<210> SEQ ID NO 10
<211> LENGTH: 79
<212> TYPE: DNA
<213> ORGANISM: Artificial Sequence
<220> FEATURE:
<223> OTHER INFORMATION: Reverse primer for aroD deletion cassette

<400> SEQUENCE: 10
atatattttt tagttcggcg gggagggtgt tcccgccgaa atattattgc gccatggtcc    60
atatgaatat cctccttag                                                 79

<210> SEQ ID NO 11
<211> LENGTH: 23

-continued

```
<212> TYPE: DNA
<213> ORGANISM: Artificial Sequence
<220> FEATURE:
<223> OTHER INFORMATION: Forward primer for aroD deletion

<400> SEQUENCE: 11
caaagatttc cctctggaat atg                                            23

<210> SEQ ID NO 12
<211> LENGTH: 21
<212> TYPE: DNA
<213> ORGANISM: Artificial Sequence
<220> FEATURE:
<223> OTHER INFORMATION: Reverse primer for aroD deletion

<400> SEQUENCE: 12
cagatgtgat tttccctacg c                                              21

<210> SEQ ID NO 13
<211> LENGTH: 40
<212> TYPE: DNA
<213> ORGANISM: Artificial Sequence
<220> FEATURE:
<223> OTHER INFORMATION: Forward primer for aroG

<400> SEQUENCE: 13
aaggagctca ctagtggtac ggatgctcct gttatggtcg                          40

<210> SEQ ID NO 14
<211> LENGTH: 41
<212> TYPE: DNA
<213> ORGANISM: Artificial Sequence
<220> FEATURE:
<223> OTHER INFORMATION: Reverse primer for aroG

<400> SEQUENCE: 14
ctctcttcga caatttccac ttacccgcga cgcgctttta c                        41

<210> SEQ ID NO 15
<211> LENGTH: 41
<212> TYPE: DNA
<213> ORGANISM: Artificial Sequence
<220> FEATURE:
<223> OTHER INFORMATION: Forward primer for ppsA

<400> SEQUENCE: 15
gtaaaagcgc gtcgcgggta agtggaaatt gtcgaagaga g                        41

<210> SEQ ID NO 16
<211> LENGTH: 42
<212> TYPE: DNA
<213> ORGANISM: Artificial Sequence
<220> FEATURE:
<223> OTHER INFORMATION: Reverse primer for ppsA

<400> SEQUENCE: 16
gccctagtgg atctgatggg ttatttcttc agttcagcca gg                       42

<210> SEQ ID NO 17
<211> LENGTH: 42
<212> TYPE: DNA
<213> ORGANISM: Artificial Sequence
<220> FEATURE:
<223> OTHER INFORMATION: Forward primer for tktA

<400> SEQUENCE: 17
```
cctggctgaa ctgaagaaat aacccatcag atccactagg gc           42

<210> SEQ ID NO 18
<211> LENGTH: 42
<212> TYPE: DNA
<213> ORGANISM: Artificial Sequence
<220> FEATURE:
<223> OTHER INFORMATION: Reverse primer for tktA

<400> SEQUENCE: 18
cgacaccggt cagcagggtg ttacagcagt tcttttgctt tc           42

<210> SEQ ID NO 19
<211> LENGTH: 20
<212> TYPE: DNA
<213> ORGANISM: Artificial Sequence
<220> FEATURE:
<223> OTHER INFORMATION: Forward primer for confirmtion of
    pSKH130-deltafhuA-Pn-aroG-Pn-ppsA-Pn-tktA plasmid

<400> SEQUENCE: 19
gaaaatgccg atgggtaccg                                    20

<210> SEQ ID NO 20
<211> LENGTH: 26
<212> TYPE: DNA
<213> ORGANISM: Artificial Sequence
<220> FEATURE:
<223> OTHER INFORMATION: Reverse primer for confirmtion of
    pSKH130-deltafhuA-Pn-aroG-Pn-ppsA-Pn-tktA plasmid

<400> SEQUENCE: 20
cgttagaacg cggctacaat taatac                             26

<210> SEQ ID NO 21
<211> LENGTH: 49
<212> TYPE: DNA
<213> ORGANISM: Artificial Sequence
<220> FEATURE:
<223> OTHER INFORMATION: Forward primer for Ava_ABCD

<400> SEQUENCE: 21
catctcacac cgagattatt ttagtactat gagtatcgtc caagcaaag    49

<210> SEQ ID NO 22
<211> LENGTH: 46
<212> TYPE: DNA
<213> ORGANISM: Artificial Sequence
<220> FEATURE:
<223> OTHER INFORMATION: Reverse primer for Ava_ABCD

<400> SEQUENCE: 22
caatttcgta tagagtctca ctagtaccgc aaaaaggcca tccgtc       46

<210> SEQ ID NO 23
<211> LENGTH: 43
<212> TYPE: DNA
<213> ORGANISM: Artificial Sequence
<220> FEATURE:
<223> OTHER INFORMATION: Forward primer for Ptrc prompter fragment

<400> SEQUENCE: 23
tctcacaccg agattatttt agtcgactgc acggtgcacc aat          43

<210> SEQ ID NO 24
<211> LENGTH: 50

```
<212> TYPE: DNA
<213> ORGANISM: Artificial Sequence
<220> FEATURE:
<223> OTHER INFORMATION: Reverse primer for Ptrc prompter fragment

<400> SEQUENCE: 24
tttgcttgga cgatactcat agtctgtttc ctgtgtgaaa ttgttatccg         50

<210> SEQ ID NO 25
<211> LENGTH: 43
<212> TYPE: DNA
<213> ORGANISM: Artificial Sequence
<220> FEATURE:
<223> OTHER INFORMATION: Forward primer for PCJ1 or PCJ2.2 prompter
      fragment

<400> SEQUENCE: 25
tctcacaccg agattatttt agtcaccgcg ggcttattcc att                43

<210> SEQ ID NO 26
<211> LENGTH: 49
<212> TYPE: DNA
<213> ORGANISM: Artificial Sequence
<220> FEATURE:
<223> OTHER INFORMATION: Reverse primer for PCJ1 or PCJ2.2 prompter
      fragment

<400> SEQUENCE: 26
ttgcttggac gatactcata gtatcttaat ctcctagatt gggtttcac          49

<210> SEQ ID NO 27
<211> LENGTH: 50
<212> TYPE: DNA
<213> ORGANISM: Artificial Sequence
<220> FEATURE:
<223> OTHER INFORMATION: Reverse primer for PCJ2.2 prompter fragment

<400> SEQUENCE: 27
tttgcttgga cgatactcat agtatcttaa tctcctagat ttggtttcac         50

<210> SEQ ID NO 28
<211> LENGTH: 22
<212> TYPE: DNA
<213> ORGANISM: Artificial Sequence
<220> FEATURE:
<223> OTHER INFORMATION: Forward primer for confirmation of Ava-ABCD
      integration

<400> SEQUENCE: 28
cagaatgagt gaacaaccac gg                                       22

<210> SEQ ID NO 29
<211> LENGTH: 25
<212> TYPE: DNA
<213> ORGANISM: Artificial Sequence
<220> FEATURE:
<223> OTHER INFORMATION: Reverse primer for confirmation of Ava-ABCD
      integration

<400> SEQUENCE: 29
catatccaat aacccagaca aaacc                                    25

<210> SEQ ID NO 30
<211> LENGTH: 31
<212> TYPE: DNA
<213> ORGANISM: Artificial Sequence
<220> FEATURE:
```

```
<223> OTHER INFORMATION: Forward primer for Ptrc/PCJ1-Ava_AB or
      Ptrc/PCJ1-Ava_ABC

<400> SEQUENCE: 30
gatcggatcc atgagtatcg tccaagcaaa g                              31

<210> SEQ ID NO 31
<211> LENGTH: 29
<212> TYPE: DNA
<213> ORGANISM: Artificial Sequence
<220> FEATURE:
<223> OTHER INFORMATION: Reverse primer for Ptrc/PCJ1-Ava_AB

<400> SEQUENCE: 31
gatcactagt ttaaggttgt attctgcgg                                 29

<210> SEQ ID NO 32
<211> LENGTH: 29
<212> TYPE: DNA
<213> ORGANISM: Artificial Sequence
<220> FEATURE:
<223> OTHER INFORMATION: Reverse primer for Ptrc/PCJ1-Ava_ABC

<400> SEQUENCE: 32
gatcactagt ctaatctccc cccaattcc                                 29

<210> SEQ ID NO 33
<211> LENGTH: 60
<212> TYPE: DNA
<213> ORGANISM: Artificial Sequence
<220> FEATURE:
<223> OTHER INFORMATION: Forward primer for Ava_ABCD

<400> SEQUENCE: 33
ccaaacacca acaaaaggct ctacccatat gatgagtatc gtccaagcaa agtttgaagc   60

<210> SEQ ID NO 34
<211> LENGTH: 60
<212> TYPE: DNA
<213> ORGANISM: Artificial Sequence
<220> FEATURE:
<223> OTHER INFORMATION: Reverse primer for Ava_ABCD

<400> SEQUENCE: 34
agagggtgac gctagtcaga actagtttat gaattatttt ccagacaatc ttgtaaacgc   60

<210> SEQ ID NO 35
<211> LENGTH: 58
<212> TYPE: DNA
<213> ORGANISM: Artificial Sequence
<220> FEATURE:
<223> OTHER INFORMATION: Forward primer for CJ7 promoter fragment

<400> SEQUENCE: 35
ccaaacacca acaaaaggct ctacccatat gagaaacatc ccagcgctac taataggg     58

<210> SEQ ID NO 36
<211> LENGTH: 48
<212> TYPE: DNA
<213> ORGANISM: Artificial Sequence
<220> FEATURE:
<223> OTHER INFORMATION: Reverse primer for CJ7 promoter fragment

<400> SEQUENCE: 36
caaactttgc ttggacgata ctcatagtgt ttcctttcgt tgggtacg               48
```

<210> SEQ ID NO 37
<211> LENGTH: 47
<212> TYPE: DNA
<213> ORGANISM: Artificial Sequence
<220> FEATURE:
<223> OTHER INFORMATION: Forward primer for lysc8 promoter fragment

<400> SEQUENCE: 37
caccaacaaa aggctctacc catatgaaca ctcctctggc taggtag       47

<210> SEQ ID NO 38
<211> LENGTH: 48
<212> TYPE: DNA
<213> ORGANISM: Artificial Sequence
<220> FEATURE:
<223> OTHER INFORMATION: Reverse primer for lysc8 promoter fragment

<400> SEQUENCE: 38
caaactttgc ttggacgata ctcatctttg tgcacctttc gatctacg       48

<210> SEQ ID NO 39
<211> LENGTH: 54
<212> TYPE: DNA
<213> ORGANISM: Artificial Sequence
<220> FEATURE:
<223> OTHER INFORMATION: Forward primer for O2 promoter fragment

<400> SEQUENCE: 39
ccaaacacca acaaaaggct tacccatat gcaataatcg tgaattttgg cagc       54

<210> SEQ ID NO 40
<211> LENGTH: 53
<212> TYPE: DNA
<213> ORGANISM: Artificial Sequence
<220> FEATURE:
<223> OTHER INFORMATION: Reverse primer for O2 promoter fragment

<400> SEQUENCE: 40
caaactttgc ttggacgata ctcattgttt tgatctcctc caataatcta tgc       53

<210> SEQ ID NO 41
<211> LENGTH: 32
<212> TYPE: DNA
<213> ORGANISM: Artificial Sequence
<220> FEATURE:
<223> OTHER INFORMATION: Forward primer for aroD genes to construct pDC
     delta aroD

<400> SEQUENCE: 41
gatcggatcc cactggacgt ttgggtgaga cc       32

<210> SEQ ID NO 42
<211> LENGTH: 37
<212> TYPE: DNA
<213> ORGANISM: Artificial Sequence
<220> FEATURE:
<223> OTHER INFORMATION: Reverse primer for aroD genes to construct pDC
     delta aroD

<400> SEQUENCE: 42
gatcggatcc actagtttta ggttccattt ctaattg       37

<210> SEQ ID NO 43
<211> LENGTH: 29
<212> TYPE: DNA
<213> ORGANISM: Artificial Sequence -continued

```
<220> FEATURE:
<223> OTHER INFORMATION: Forward primer for aroD genes to construct pDC
      delta aroD

<400> SEQUENCE: 43
gatcactagt atgaacgaca gtattctcc                                        29

<210> SEQ ID NO 44
<211> LENGTH: 30
<212> TYPE: DNA
<213> ORGANISM: Artificial Sequence
<220> FEATURE:
<223> OTHER INFORMATION: Reverse primer for aroD genes to construct pDC
      delta aroD

<400> SEQUENCE: 44
gatcaagctt gttacatcct gacgttgtgg                                       30

<210> SEQ ID NO 45
<211> LENGTH: 30
<212> TYPE: DNA
<213> ORGANISM: Artificial Sequence
<220> FEATURE:
<223> OTHER INFORMATION: Forward primer for Ava_A

<400> SEQUENCE: 45
cgcggatcca tgagtatcgt ccaagcaaag                                       30

<210> SEQ ID NO 46
<211> LENGTH: 33
<212> TYPE: DNA
<213> ORGANISM: Artificial Sequence
<220> FEATURE:
<223> OTHER INFORMATION: Reverse primer for Ava_A

<400> SEQUENCE: 46
cgcctcgagt tatttaacac tcccgattaa ttc                                   33

<210> SEQ ID NO 47
<211> LENGTH: 31
<212> TYPE: DNA
<213> ORGANISM: Artificial Sequence
<220> FEATURE:
<223> OTHER INFORMATION: Forward primer for Ava_B

<400> SEQUENCE: 47
cgcggatcca tgacaaatgt gattgtccaa c                                     31

<210> SEQ ID NO 48
<211> LENGTH: 35
<212> TYPE: DNA
<213> ORGANISM: Artificial Sequence
<220> FEATURE:
<223> OTHER INFORMATION: Reverse primer for Ava_B

<400> SEQUENCE: 48
cgcctcgagt taaggttgta ttctgcggat aattg                                 35

<210> SEQ ID NO 49
<211> LENGTH: 32
<212> TYPE: DNA
<213> ORGANISM: Artificial Sequence
<220> FEATURE:
<223> OTHER INFORMATION: Forward primer for Ava_C

<400> SEQUENCE: 49
```
cgcggatcca tggcacaatc ccttcccctt tc                                      32

<210> SEQ ID NO 50
<211> LENGTH: 31
<212> TYPE: DNA
<213> ORGANISM: Artificial Sequence
<220> FEATURE:
<223> OTHER INFORMATION: Reverse primer for Ava_C

<400> SEQUENCE: 50
cgcctcgagc taatctcccc ccaattccac c                                       31

<210> SEQ ID NO 51
<211> LENGTH: 34
<212> TYPE: DNA
<213> ORGANISM: Artificial Sequence
<220> FEATURE:
<223> OTHER INFORMATION: Forward primer for Ava_D

<400> SEQUENCE: 51
cgcggatcca tgcagactat agattttaat attc                                    34

<210> SEQ ID NO 52
<211> LENGTH: 33
<212> TYPE: DNA
<213> ORGANISM: Artificial Sequence
<220> FEATURE:
<223> OTHER INFORMATION: Reverse primer for Ava_D

<400> SEQUENCE: 52
cgcctcgagt tatgaattat tttccagaca atc                                     33

<210> SEQ ID NO 53
<211> LENGTH: 30
<212> TYPE: DNA
<213> ORGANISM: Artificial Sequence
<220> FEATURE:
<223> OTHER INFORMATION: Forward primer for Npr_A

<400> SEQUENCE: 53
cgcggatcca tgagtaatgt tcaagcatcg                                         30

<210> SEQ ID NO 54
<211> LENGTH: 29
<212> TYPE: DNA
<213> ORGANISM: Artificial Sequence
<220> FEATURE:
<223> OTHER INFORMATION: Reverse primer for Npr_A

<400> SEQUENCE: 54
cgcctcgagt cacactccca atagtttgg                                          29

<210> SEQ ID NO 55
<211> LENGTH: 31
<212> TYPE: DNA
<213> ORGANISM: Artificial Sequence
<220> FEATURE:
<223> OTHER INFORMATION: Forward primer for Npr_B

<400> SEQUENCE: 55
cgcggatcca tgaccagtat tttaggacga g                                       31

<210> SEQ ID NO 56
<211> LENGTH: 28
<212> TYPE: DNA
<213> ORGANISM: Artificial Sequence

```
<220> FEATURE:
<223> OTHER INFORMATION: Reverse primer for Npr_B

<400> SEQUENCE: 56
cgcctcgagt tataccaagc gtctaatc                                          28

<210> SEQ ID NO 57
<211> LENGTH: 32
<212> TYPE: DNA
<213> ORGANISM: Artificial Sequence
<220> FEATURE:
<223> OTHER INFORMATION: Forward primer for Npr_C

<400> SEQUENCE: 57
cgcggatcca tggcacaatc aatctcttta tc                                     32

<210> SEQ ID NO 58
<211> LENGTH: 31
<212> TYPE: DNA
<213> ORGANISM: Artificial Sequence
<220> FEATURE:
<223> OTHER INFORMATION: Reverse primer for Npr_C

<400> SEQUENCE: 58
cgcctcgagt tagtcgcccc ctaattccac g                                      31

<210> SEQ ID NO 59
<211> LENGTH: 31
<212> TYPE: DNA
<213> ORGANISM: Artificial Sequence
<220> FEATURE:
<223> OTHER INFORMATION: Forward primer for Npr_D

<400> SEQUENCE: 59
cgcggatcca tgccagtact aaatatcctt c                                      31

<210> SEQ ID NO 60
<211> LENGTH: 35
<212> TYPE: DNA
<213> ORGANISM: Artificial Sequence
<220> FEATURE:
<223> OTHER INFORMATION: Reverse primer for Npr_D

<400> SEQUENCE: 60
cgcctcgagt caattttgta cacctttttt attac                                  35

<210> SEQ ID NO 61
<211> LENGTH: 48
<212> TYPE: DNA
<213> ORGANISM: Artificial Sequence
<220> FEATURE:
<223> OTHER INFORMATION: Forward primer for pGPD

<400> SEQUENCE: 61
acgtaagata attgtatatt acgcagttta tcattatcaa tactcgcc                    48

<210> SEQ ID NO 62
<211> LENGTH: 40
<212> TYPE: DNA
<213> ORGANISM: Artificial Sequence
<220> FEATURE:
<223> OTHER INFORMATION: Reverse primer for pGPD

<400> SEQUENCE: 62
gtaacgacaa tcctctccat gtggtcttga atcaaagctg                             40
```

<210> SEQ ID NO 63
<211> LENGTH: 39
<212> TYPE: DNA
<213> ORGANISM: Artificial Sequence
<220> FEATURE:
<223> OTHER INFORMATION: Forward primer for LoxP(Ura)

<400> SEQUENCE: 63
ccgattgtca atcagcgtaa cagctgaagc ttcgtacgc                    39

<210> SEQ ID NO 64
<211> LENGTH: 44
<212> TYPE: DNA
<213> ORGANISM: Artificial Sequence
<220> FEATURE:
<223> OTHER INFORMATION: Reverse primer for LoxP(Ura)

<400> SEQUENCE: 64
ttgttttggc cagtcggcaa gggcataggc cactagtgga tctg              44

<210> SEQ ID NO 65
<211> LENGTH: 40
<212> TYPE: DNA
<213> ORGANISM: Artificial Sequence
<220> FEATURE:
<223> OTHER INFORMATION: Forward primer for aroB

<400> SEQUENCE: 65
cagctttgat tcaagaccac atggagagga ttgtcgttac                   40

<210> SEQ ID NO 66
<211> LENGTH: 39
<212> TYPE: DNA
<213> ORGANISM: Artificial Sequence
<220> FEATURE:
<223> OTHER INFORMATION: Reverse primer for aroB

<400> SEQUENCE: 66
gcgtacgaag cttcagctgt tacgctgatt gacaatcgg                    39

<210> SEQ ID NO 67
<211> LENGTH: 32
<212> TYPE: DNA
<213> ORGANISM: Artificial Sequence
<220> FEATURE:
<223> OTHER INFORMATION: Forward primer for ARO1 fragment 1

<400> SEQUENCE: 67
accattcaag agtatatgag agaaggaaaa ct                           32

<210> SEQ ID NO 68
<211> LENGTH: 47
<212> TYPE: DNA
<213> ORGANISM: Artificial Sequence
<220> FEATURE:
<223> OTHER INFORMATION: Reverse primer for ARO1 fragment 1

<400> SEQUENCE: 68
ggcgagtatt gataatgata aactgcgtaa tatacaatta tcttacg           47

<210> SEQ ID NO 69
<211> LENGTH: 44
<212> TYPE: DNA
<213> ORGANISM: Artificial Sequence
<220> FEATURE:
<223> OTHER INFORMATION: Forward primer for ARO1 fragment 2

<400> SEQUENCE: 69
cagatccact agtggcctat gcccttgccg actggccaaa acaa         44

<210> SEQ ID NO 70
<211> LENGTH: 20
<212> TYPE: DNA
<213> ORGANISM: Artificial Sequence
<220> FEATURE:
<223> OTHER INFORMATION: Reverse primer for ARO1 fragment 2

<400> SEQUENCE: 70
caaatatcaa tggcacgttg         20

<210> SEQ ID NO 71
<211> LENGTH: 759
<212> TYPE: DNA
<213> ORGANISM: Escherichia coli W3110

<400> SEQUENCE: 71
atgaaaaccg taactgtaaa agatctcgtc attggtacgg gcgcacctaa atcatcgtc     60 tcgctgatgg cgaaagatat cgccagcgtg aaatccgaag ctctcgccta tcgtgaagcg    120
gactttgata ttctggaatg gcgtgtggac cactatgccg acctctccaa tgtggagtct    180
gtcatggcgg cagcaaaaat tctccgtgag accatgccag aaaaaccgct gctgtttacc    240
ttccgcagtg ccaaagaagg cggcgagcag gcgatttcca ccgaggctta tattgcactc    300
aatcgtgcag ccatcgacag cggcctggtt gatatgatcg atctggagtt atttaccggt    360
gatgatcagg ttaaagaaac cgtcgcctac gcccacgcgc atgatgtgaa agtagtcatg    420
tccaaccatg acttccataa aacgccggaa gccgaagaaa tcattgcccg tctgcgcaaa    480
atgcaatcct tcgacgccga tattcctaag attgcgctga tgccgcaaag taccagcgat    540
gtgctgacgt tgcttgccgc gaccctggag atgcaggagc agtatgccga tcgtccaatt    600
atcacgatgt cgatggcaaa aactggcgta atttctcgtc tggctggtga agtatttggc    660
tcggcggcaa ctttggtgc ggtaaaaaaa gcgtctgcgc agggcaaat ctcggtaaat    720 gatttgcgca cggtattaac tattttacac caggcataa                 759

<210> SEQ ID NO 72
<211> LENGTH: 252
<212> TYPE: PRT
<213> ORGANISM: Escherichia coli W3110

<400> SEQUENCE: 72

Met Lys Thr Val Thr Val Lys Asp Leu Val Ile Gly Thr Gly Ala Pro
1               5                   10                  15

Lys Ile Ile Val Ser Leu Met Ala Lys Asp Ile Ala Ser Val Lys Ser
            20                  25                  30

Glu Ala Leu Ala Tyr Arg Glu Ala Asp Phe Asp Ile Leu Glu Trp Arg
        35                  40                  45

Val Asp His Tyr Ala Asp Leu Ser Asn Val Glu Ser Val Met Ala Ala
    50                  55                  60

Ala Lys Ile Leu Arg Glu Thr Met Pro Glu Lys Pro Leu Leu Phe Thr
65                  70                  75                  80

Phe Arg Ser Ala Lys Glu Gly Gly Glu Gln Ala Ile Ser Thr Glu Ala
                85                  90                  95

Tyr Ile Ala Leu Asn Arg Ala Ala Ile Asp Ser Gly Leu Val Asp Met
            100                 105                 110

Ile Asp Leu Glu Leu Phe Thr Gly Asp Asp Gln Val Lys Glu Thr Val
    115                 120                 125

Ala Tyr Ala His Ala His Asp Val Lys Val Val Met Ser Asn His Asp
130                 135                 140

Phe His Lys Thr Pro Glu Ala Glu Glu Ile Ile Ala Arg Leu Arg Lys
145                 150                 155                 160

Met Gln Ser Phe Asp Ala Asp Ile Pro Lys Ile Ala Leu Met Pro Gln
                165                 170                 175

Ser Thr Ser Asp Val Leu Thr Leu Leu Ala Ala Thr Leu Glu Met Gln
            180                 185                 190

Glu Gln Tyr Ala Asp Arg Pro Ile Ile Thr Met Ser Met Ala Lys Thr
        195                 200                 205

Gly Val Ile Ser Arg Leu Ala Gly Glu Val Phe Gly Ser Ala Ala Thr
    210                 215                 220

Phe Gly Ala Val Lys Lys Ala Ser Ala Pro Gly Gln Ile Ser Val Asn
225                 230                 235                 240

Asp Leu Arg Thr Val Leu Thr Ile Leu His Gln Ala
                245                 250

<210> SEQ ID NO 73
<211> LENGTH: 1053
<212> TYPE: DNA
<213> ORGANISM: Escherichia coli W3110

<400> SEQUENCE: 73

```
atgaattatc agaacgacga tttacgcatc aaagaaatca agagttact tcctcctgtc      60
gcattgctgg aaaaattccc cgctactgaa atgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420
gcaggtgagt ttctcgatat gatcaccca caatatctcg ctgacctgat gagctgggc     480
gcaattggcg cacgtaccac cgaatcgcag gtgcaccgcg aactggcatc agggctttct     540
tgtccggtcg gcttcaaaaa tggcaccgac ggtacgatta agtggctat cgatgccatt     600
aatgccgccg gtgcgccgca ctgcttcctg tccgtaacga aatgggggca ttcggcgatt     660
gtgaatacca gcggtaacgg cgattgccat atcattctgc gcggcggtaa agagcctaac     720
tacagcgcga agcacgttgc tgaagtgaaa gaagggctga caaagcagg cctgccagca     780
caggtgatga tcgatttcag ccatgctaac tcgtccaaac aattcaaaaa gcagatggat     840
gtttgtgctg acgtttgcca gcagattgcc ggtggcgaaa aggccattat tggcgtgatg     900
gtggaaagcc atctggtgga aggcaatcag agcctcgaga gcgggagcc gctggcctac     960
ggtaagagca tcaccgatgc ctgcatcggc tgggaagata ccgatgctct gttacgtcaa    1020
ctggcgaatg cagtaaaagc gcgtcgcggg taa                                 1053
```

<210> SEQ ID NO 74
<211> LENGTH: 350
<212> TYPE: PRT
<213> ORGANISM: Escherichia coli W3110

<400> SEQUENCE: 74

```
Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
                100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
        130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 75
<211> LENGTH: 2379
<212> TYPE: DNA
<213> ORGANISM: Escherichia coli W3110

<400> SEQUENCE: 75
atgtccaaca atggctcgtc accgctggtg ctttggtata accaactcgg catgaatgat      60
gtagacaggg ttgggggcaa aaatgcctcc ctgggtgaaa tgattactaa tctttccgga     120
```

-continued

| | |
|---|---|
| atgggtgttt ccgttccgaa tggtttcgcc acaaccgccg acgcgtttaa ccagtttctg | 180 |
| gaccaaagcg gcgtaaacca gcgcatttat gaactgctgg ataaaacgga tattgacgat | 240 |
| gttactcagc ttgcgaaagc gggcgcgcaa atccgccagt ggattatcga cactcccttc | 300 |
| cagcctgagc tggaaaacgc catccgcgaa gcctatgcac agctttccgc cgatgacgaa | 360 |
| aacgcctctt ttgcggtgcg ctcctccgcc accgcagaag atatgccgga cgcttctttt | 420 |
| gccggtcagc aggaaaacctt cctcaacgtt cagggttttg acgccgttct cgtggcagtg | 480 |
| aaacatgtat ttgcttctct gtttaacgat cgcgccatct cttatcgtgt gcaccagggt | 540 |
| tacgatcacc gtggtgtggc gctctccgcc ggtgttcaac ggatggtgcg ctctgacctc | 600 |
| gcatcatctg gcgtgatgtt ctccattgat accgaatccg gctttgacca ggtggtgttt | 660 |
| atcacttccg catggggcct tggtgagatg gtcgtgcagg gtgcggttaa cccggatgag | 720 |
| ttttacgtgc ataaaccgac actggcggcg aatcgcccgg ctatcgtgcg ccgcaccatg | 780 |
| gggtcgaaaa aaatccgcat ggtttacgcg ccgacccagg agcacggcaa gcaggttaaa | 840 |
| atcgaagacg taccgcagga acagcgtgac atcttctcgc tgaccaacga agaagtgcag | 900 |
| gaactggcaa acaggccgt acaaattgag aaacactacg gtcgcccgat ggatattgag | 960 |
| tgggcgaaag atggccacac cggtaaactg ttcattgtgc aggcgcgtcc ggaaaccgtg | 1020 |
| cgctcacgcg gtcaggtcat ggagcgttat acgctgcatt cacagggtaa gattatcgcc | 1080 |
| gaaggccgtg ctatcggtca tcgcatcggt gcgggtccgg tgaaagtcat ccatgacatc | 1140 |
| agcgaaatga accgcatcga acctggcgac gtgctggtta ctgacatgac cgacccggac | 1200 |
| tgggaaccga tcatgaagaa agcatctgcc atcgtcacca accgtggcgg tcgtacctgt | 1260 |
| cacgcggcga tcatcgctcg tgaactgggc attccggcgg tagtgggctg tggagatgca | 1320 |
| acagaacgga tgaaagacgg tgagaacgtc actgtttctt gtgccgaagg tgataccggt | 1380 |
| tacgtctatg cggagttgct ggaatttagc gtgaaaagct ccagcgtaga acgatgccg | 1440 |
| gatctgccgt tgaaagtgat gatgaacgtc ggtaacccgg accgtgcttt cgacttcgcc | 1500 |
| tgcctaccga acgaaggcgt gggccttgcg cgtctggaat ttatcatcaa ccgtatgatt | 1560 |
| ggcgtccacc cacgcgcact gcttgagttt gacgatcagg aaccgcagtt gcaaaacgaa | 1620 |
| atccgcgaga tgatgaaagg ttttgattct ccgcgtgaat tttacgttgg tcgtctgact | 1680 |
| gaagggatcg cgacgctggg tgccgcgttt tatccgaagc gcgtcattgt ccgtctctct | 1740 |
| gattttaaat cgaacgaata tgccaacctg gtcggtggtg agcgttacga gccagatgaa | 1800 |
| gagaacccga tgctcggctt ccgtggcgcg ggccgctatg tttccgacag cttccgcgac | 1860 |
| tgtttcgcgc tggagtgtga agcagtgaaa cgtgtgcgca acgacatggg actgaccaac | 1920 |
| gttgagatca tgatcccgtt cgtgcgtacc gtagatcagg cgaaagcggt ggttgaagaa | 1980 |
| ctggcgcgtc aggggctgaa acgtggcgag aacgggctga aaatcatcat gatgtgtgaa | 2040 |
| atcccgtcca acgccttgct ggccgagcag ttcctcgaat atttcgacgg cttctcaatt | 2100 |
| ggctcaaacg atatgacgca gctggcgctc ggtctggacc gtgactccgg cgtggtgtct | 2160 |
| gaattgttcg atgagcgcaa cgatgcggtg aaagcactgc tgtcgatggc tatccgtgcc | 2220 |
| gcgaagaaac agggcaaata tgtcgggatt tgccgtcagg gtccgtccga ccacgaagac | 2280 |
| tttgccgcat ggttgatgga agagggatc gatagcctgt ctctgaaccc ggacaccgtg | 2340 |
| gtgcaaacct ggttaagcct ggctgaactg aagaaataa | 2379 |

<210> SEQ ID NO 76
<211> LENGTH: 792

<212> TYPE: PRT
<213> ORGANISM: Escherichia coli W3110

<400> SEQUENCE: 76

Met Ser Asn Asn Gly Ser Ser Pro Leu Val Leu Trp Tyr Asn Gln Leu
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80

Val Thr Gln Leu Ala Lys Ala Gly Ala Gln Ile Arg Gln Trp Ile Ile
                85                  90                  95

Asp Thr Pro Phe Gln Pro Glu Leu Glu Asn Ala Ile Arg Glu Ala Tyr
            100                 105                 110

Ala Gln Leu Ser Ala Asp Asp Glu Asn Ala Ser Phe Ala Val Arg Ser
        115                 120                 125

Ser Ala Thr Ala Glu Asp Met Pro Asp Ala Ser Phe Ala Gly Gln Gln
    130                 135                 140

Glu Thr Phe Leu Asn Val Gln Gly Phe Asp Ala Val Leu Val Ala Val
145                 150                 155                 160

Lys His Val Phe Ala Ser Leu Phe Asn Asp Arg Ala Ile Ser Tyr Arg
                165                 170                 175

Val His Gln Gly Tyr Asp His Arg Gly Val Ala Leu Ser Ala Gly Val
            180                 185                 190

Gln Arg Met Val Arg Ser Asp Leu Ala Ser Ser Gly Val Met Phe Ser
        195                 200                 205

Ile Asp Thr Glu Ser Gly Phe Asp Gln Val Val Phe Ile Thr Ser Ala
    210                 215                 220

Trp Gly Leu Gly Glu Met Val Val Gln Gly Ala Val Asn Pro Asp Glu
225                 230                 235                 240

Phe Tyr Val His Lys Pro Thr Leu Ala Ala Asn Arg Pro Ala Ile Val
                245                 250                 255

Arg Arg Thr Met Gly Ser Lys Lys Ile Arg Met Val Tyr Ala Pro Thr
            260                 265                 270

Gln Glu His Gly Lys Gln Val Lys Ile Glu Asp Val Pro Gln Glu Gln
        275                 280                 285

Arg Asp Ile Phe Ser Leu Thr Asn Glu Glu Val Gln Glu Leu Ala Lys
    290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                325                 330                 335

Pro Glu Thr Val Arg Ser Arg Gly Gln Val Met Glu Arg Tyr Thr Leu
            340                 345                 350

His Ser Gln Gly Lys Ile Ile Ala Glu Gly Arg Ala Ile Gly His Arg
        355                 360                 365

Ile Gly Ala Gly Pro Val Lys Val Ile His Asp Ile Ser Glu Met Asn
    370                 375                 380

Arg Ile Glu Pro Gly Asp Val Leu Val Thr Asp Met Thr Asp Pro Asp
385                 390                 395                 400

```
Trp Glu Pro Ile Met Lys Lys Ala Ser Ala Ile Val Thr Asn Arg Gly
                405                 410                 415

Gly Arg Thr Cys His Ala Ala Ile Ile Ala Arg Glu Leu Gly Ile Pro
            420                 425                 430

Ala Val Val Gly Cys Gly Asp Ala Thr Glu Arg Met Lys Asp Gly Glu
            435                 440                 445

Asn Val Thr Val Ser Cys Ala Glu Gly Asp Thr Gly Tyr Val Tyr Ala
        450                 455                 460

Glu Leu Leu Glu Phe Ser Val Lys Ser Ser Val Glu Thr Met Pro
465                 470                 475                 480

Asp Leu Pro Leu Lys Val Met Met Asn Val Gly Asn Pro Asp Arg Ala
                485                 490                 495

Phe Asp Phe Ala Cys Leu Pro Asn Glu Gly Val Gly Leu Ala Arg Leu
            500                 505                 510

Glu Phe Ile Ile Asn Arg Met Ile Gly Val His Pro Arg Ala Leu Leu
            515                 520                 525

Glu Phe Asp Asp Gln Glu Pro Gln Leu Gln Asn Glu Ile Arg Glu Met
        530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Tyr Pro Lys Arg Val Ile
                565                 570                 575

Val Arg Leu Ser Asp Phe Lys Ser Asn Glu Tyr Ala Asn Leu Val Gly
            580                 585                 590

Gly Glu Arg Tyr Glu Pro Asp Glu Asn Pro Met Leu Gly Phe Arg
            595                 600                 605

Gly Ala Gly Arg Tyr Val Ser Asp Ser Phe Arg Asp Cys Phe Ala Leu
        610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
            675                 680                 685

Glu Gln Phe Leu Glu Tyr Phe Asp Gly Phe Ser Ile Gly Ser Asn Asp
        690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
            755                 760                 765

Gly Ile Asp Ser Leu Ser Leu Asn Pro Asp Thr Val Val Gln Thr Trp
        770                 775                 780

Leu Ser Leu Ala Glu Leu Lys Lys
785                 790

<210> SEQ ID NO 77
<211> LENGTH: 1992
```

<212> TYPE: DNA
<213> ORGANISM: Escherichia coli W3110

<400> SEQUENCE: 77

```
atgtcctcac gtaaagagct tgccaatgct attcgtgcgc tgagcatgga cgcagtacag      60
aaagccaaat ccggtcaccc gggtgcccct atgggtatgg ctgacattgc cgaagtcctg     120
tggcgtgatt tcctgaaaca caacccgcag aatccgtcct gggctgaccg tgaccgcttc     180
gtgctgtcca acggccacgg ctccatgctg atctacagcc tgctgcacct caccggttac     240
gatctgccga tggaagaact gaaaaacttc cgtcagctgc actctaaaac tccgggtcac     300
ccggaagtgg gttacaccgc tggtgtggaa accaccaccg gtccgctggg tcagggtatt     360
gccaacgcag tcggtatggc gattgcagaa aaaacgctgg cggcgcagtt taaccgtccg     420
ggccacgaca ttgtcgacca ctacacctac gccttcatgg gcgacggctg catgatggaa     480
ggcatctccc acgaagtttg ctctctggcg gtacgctgaa gctgggtaa actgattgca     540
ttctacgatg acaacggtat ttctatcgat ggtcacgttg aaggctggtt caccgacgac     600
accgcaatgc gtttcgaagc ttacggctgg cacgttattc gcgacatcga cggtcatgac     660
gcggcatcta tcaaacgcgc agtagaagaa gcgcgcgcag tgactgacaa accttccctg     720
ctgatgtgca aaaccatcat cggtttcggt tccccgaaca aagccggtac ccacgactcc     780
cacggtgcgc cgctgggcga cgctgaaatt gccctgaccc gcaacaact gggctggaaa     840
tatgcgccgt cgaaatccc gtctgaaatc tatgctcagt gggatgcgaa agaagcaggc     900
caggcgaaag aatccgcatg gaacgagaaa ttcgctgctt acgcgaaagc ttatccgcag     960
gaagccgctg aatttacccg ccgtatgaaa ggcgaaatgc cgtctgactt cgacgctaaa    1020
gcgaaagagt tcatcgctaa actgcaggct aatccggcga aaatcgccag ccgtaaagcg    1080
tctcagaatg ctatcgaagc gttcggtccg ctgttgccgg aattcctcgg cggttctgct    1140
gacctggcgc gtctaacct gaccctgtgg tctggttcta aagcaatcaa cgaagatgct    1200
gcgggtaact acatccacta cggtgttcgc gagttcggta tgaccgcgat tgctaacggt    1260
atctccctgc acggtggctt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga aatacggtgt tgagcgtcag gacggcccga ccgcactgat cctctcccgt    1560
cagaacctgg cgcagcagga acgaactgaa gagcaactgg caaacatcgc gcgcggtggt    1620
tatgtgctga agactgcgc cggtcagccg gaactgattt tcatcgctac cggttcagaa    1680
gttgaactgc tgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980
gaactgctgt aa                                                       1992
```

<210> SEQ ID NO 78
<211> LENGTH: 663
<212> TYPE: PRT
<213> ORGANISM: Escherichia coli W3110

<400> SEQUENCE: 78

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
            85                  90                  95

Thr Pro Gly His Pro Glu Val Gly Tyr Thr Ala Gly Val Glu Thr Thr
        100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415
```

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
            485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
        530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
            565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
        610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Glu Leu Leu
            660

<210> SEQ ID NO 79
<211> LENGTH: 438
<212> TYPE: DNA
<213> ORGANISM: Corynebacterium glutamicum ATCC 13032

<400> SEQUENCE: 79
atgcctggaa aaattctcct cctcaacggc ccaaacctga acatgctggg caaacgcgag    60
cctgacattt acggacacga caccttggaa gacgtcgtcg cgctggcaac cgctgaggct   120
gcgaagcacg gccttgaggt tgaggcgctg cagagcaatc acgaaggtga gctaatcgat   180
gcgctgcaca cgctcgcgg cacccacatc ggttgcgtga ttaaccccgg cggcctgact   240
cacacttcgg tggcgctttt ggatgctgtg aaggcgtctg agcttcctac cgttgaggtg   300
cacatttcca atccgcatgc ccgtgaagag ttccgccacc attcttacat ttccctcgcc   360
gcggtctccg ttatcgctgg cgctggcatc cagggttacc gtttcgcggt cgatatcctg   420
gcaaatctca aaagtag                                                   438

<210> SEQ ID NO 80
<211> LENGTH: 144
<212> TYPE: PRT
<213> ORGANISM: Corynebacterium glutamicum ATCC 13032

<400> SEQUENCE: 80

```
Met Pro Gly Lys Ile Leu Leu Asn Gly Pro Asn Leu Asn Met Leu
1               5                   10                  15
Gly Lys Arg Glu Pro Asp Ile Tyr Gly His Asp Thr Leu Glu Asp Val
            20                  25                  30
Val Ala Leu Ala Thr Ala Glu Ala Lys His Gly Leu Glu Val Glu
        35                  40                  45
Ala Leu Gln Ser Asn His Glu Gly Glu Leu Ile Asp Ala Leu His Asn
    50                  55                  60
Ala Arg Gly Thr His Ile Gly Cys Val Ile Asn Pro Gly Gly Leu Thr
65                  70                  75                  80
His Thr Ser Val Ala Leu Leu Asp Ala Val Lys Ala Ser Glu Leu Pro
                85                  90                  95
Thr Val Glu Val His Ile Ser Asn Pro His Ala Arg Glu Glu Phe Arg
            100                 105                 110
His His Ser Tyr Ile Ser Leu Ala Ala Val Ser Val Ile Ala Gly Ala
        115                 120                 125
Gly Ile Gln Gly Tyr Arg Phe Ala Val Asp Ile Leu Ala Asn Leu Lys
    130                 135                 140
```

<210> SEQ ID NO 81
<211> LENGTH: 4767
<212> TYPE: DNA
<213> ORGANISM: Saccharomyces cerevisiae

<400> SEQUENCE: 81

```
atggtgcagt tagccaaagt cccaattcta ggaaatgata ttatccacgt tgggtataac      60
attcatgacc atttggttga aaccataatt aaacattgtc cttcttcgac atacgttatt     120
tgcaatgata cgaacttgag taaagttcca tactaccagc aattagtcct ggaattcaag     180
gcttctttgc cagaaggctc tcgtttactt acttatgttg ttaaaccagg tgagacaagt     240
aaaagtagag aaaccaaagc gcagctagaa gattatcttt tagtggaagg atgtactcgt     300
gatacggtta tggtagcgat cggtggtggt gttattggtg acatgattgg gttcgttgca     360
tctacattta tgagaggtgt tcgtgttgtc caagtaccaa catccttatt ggcaatggtc     420
gattcctcca ttggtggtaa aactgctatt gacactcctc taggtaaaaa ctttattggt     480
gcattttggc aaccaaaatt tgtccttgta gatattaaat ggctagaaac gttagccaag     540
agagagttta tcaatgggat ggcagaagtt atcaagactg cttgtatttg aacgctgac      600
gaatttacta gattagaatc aaacgcttcg ttgttcttaa atgttgttaa tggggcaaaa     660
aatgtcaagg ttaccaatca attgacaaac gagattgacg agatatcgaa tacagatatt     720
gaagctatgt tggatcatac atataagtta gttcttgaga gtattaaggt caaagcggaa     780
gttgtctctt cggatgaacg tgaatccagt ctaagaaacc ttttgaactt cggacattct     840
attggtcatg cttatgaagc tatactaacc ccacaagcat acatggtga atgtgtgtcc     900
attggtatgg ttaaagaggc ggaattatcc cgttatttcg gtattctctc ccctacccaa     960
gttgcacgtc tatccaagat tttggttgcc tacgggttgc ctgtttcgcc tgatgagaaa    1020
tggtttaaag agctaacctt acataagaaa acaccattgg atatcttatt gaagaaaatg    1080
agtattgaca gaaaaacga gggttccaaa agaaggtgg tcatttaga agtattggt        1140
aagtgctatg gtgactccgc tcaatttgtt agcgatgaag acctgagatt tattctaaca    1200
gatgaaaccc tcgtttaccc cttcaaggac atccctgctg atcaacagaa agttgttatc    1260
```

```
ccccctggtt ctaagtccat ctccaatcgt gctttaattc ttgctgccct cggtgaaggt    1320
caatgtaaaa tcaagaactt attacattct gatgatacta acatatgtt aaccgctgtt    1380 catgaattga aggtgctac gatatcatgg gaagataatg gtgagacggt agtggtggaa    1440
ggacatggtg gttccacatt gtcagcttgt gctgacccct tatatctagg taatgcaggt    1500
actgcatcta gattttgac ttccttggct gccttggtca attctacttc aagccaaaag    1560
tatatcgttt taactggtaa cgcaagaatg caacaaagac caattgctcc tttggtcgat    1620
tctttgcgtg ctaatggtac taaaattgag tacttgaata atgaaggttc cctgccaatc    1680
aaagtttata ctgattcggt attcaaaggt ggtagaattg aattagctgc tacagtttct    1740
tctcagtacg tatcctctat cttgatgtgt gccccatacg ctgaagaacc tgtaactttg    1800
gctcttgttg gtggtaagcc aatctctaaa ttgtacgtcg atatgacaat aaaaatgatg    1860
gaaaaattcg gtatcaatgt tgaaacttct actacagaac cttacactta ttatattcca    1920
aagggacatt atattaaccc atcagaatac gtcattgaaa gtgatgcctc aagtgctaca    1980
tacccattgg ccttcgccgc aatgactggt actaccgtaa cggttccaaa cattggtttt    2040
gagtcgttac aaggtgatgc cagatttgca agagatgtct tgaaacctat gggttgtaaa    2100
ataactcaaa cggcaacttc aactactgtt tcgggtcctc ctgtaggtac tttaaagcca    2160
ttaaaacatg ttgatatgga gccaatgact gatgcgttct taactgcatg tgttgttgcc    2220
gctatttcgc acgacagtga tccaaattct gcaaatacaa ccaccattga aggtattgca    2280
aaccagcgtg tcaaagagtg taacagaatt ttggccatgg ctacagagct cgccaaattt    2340
ggcgtcaaaa ctacagaatt accagatggt attcaagtcc atggtttaaa ctcgataaaa    2400
gatttgaagg ttccttccga ctcttctgga cctgtcggtg tatgcacata tgatgatcat    2460
cgtgtggcca tgagtttctc gcttcttgca ggaatggtaa attctcaaaa tgaacgtgac    2520
gaagttgcta atcctgtaag aatacttgaa agacattgta ctggtaaaac ctggcctggc    2580
tggtgggatg tgttacattc cgaactaggt gccaaattag atggtgcaga acctttagag    2640
tgcacatcca aaagaactc aaagaaaagc gttgtcatta ttggcatgag agcagctggc    2700
aaaactacta taagtaaatg gtgcgcatcc gctctgggtt acaaattagt tgacctagac    2760
gagctgtttg agcaacagca taacaatcaa agtgttaaac aatttgttgt ggagaacggt    2820
tgggagaagt tccgtgagga agaaacaaga attttcaagg aagttattca aaattacggc    2880
gatgatggat atgttttctc aacaggtggc ggtattgttg aaagcgctga gtctagaaaa    2940
gccttaaaag attttgcctc atcaggtgga tacgttttac acttacatag ggatattgag    3000
gagacaattg tctttttaca aagtgatcct tcaagacctg cctatgtgga agaaattcgt    3060
gaagtttgga acagaaggga gggtggtat aaagaatgct caaatttctc tttcttgct    3120 cctcattgct ccgcagaagc tgagttccaa gctctaagaa gatcgtttag taagtacatt    3180
gcaaccatta caggtgtcag agaaatagaa attccaagcg gaagatctgc ctttgtgtgt    3240
ttaacctttg atgacttaac tgaacaaact gagaatttga ctccaatctg ttatggttgt    3300
gaggctgtag aggtcagagt agaccatttg gctaattact ctgctgattt cgtgagtaaa    3360
cagttatcta tattgcgtaa agccactgac agtattccta tcattttac tgtgcgaacc    3420 atgaagcaag gtggcaactt tcctgatgaa gagttcaaaa ccttgagaga gctatacgat    3480
attgccttga agaatggtgt tgaattcctt gacttagaac taactttacc tactgatatc    3540
caatatgagg ttattaacaa aaggggcaac accaagatca ttggttccca tcatgacttc    3600
caaggattat actcctggga cgacgctgaa tgggaaaaca gattcaatca agcgttaact    3660
```

```
cttgatgtgg atgttgtaaa atttgtgggt acggctgtta atttcgaaga taatttgaga    3720
ctggaacact ttagggatac acacaagaat aagcctttaa ttgcagttaa tatgacttct    3780
aaaggtagca tttctcgtgt tttgaataat gttttaacac ctgtgacatc agatttattg    3840
cctaactccg ctgcccctgg ccaattgaca gtagcacaaa ttaacaagat gtatacatct    3900
atgggaggta tcgagcctaa ggaactgttt gttgttggaa agccaattgg ccactctaga    3960
tcgccaattt tacataacac tggctatgaa atttaggtt tacctcacaa gttcgataaa     4020
tttgaaactg aatccgcaca attggtgaaa gaaaaacttt tggacggaaa caagaacttt    4080
ggcggtgctg cagtcacaat tcctctgaaa ttagatataa tgcagtacat ggatgaattg    4140
actgatgctg ctaaagttat tggtgctgta aacacagtta taccattggg taacaagaag    4200
tttaagggtg ataataccga ctggttaggt atccgtaatg ccttaattaa caatggcgtt    4260
cccgaatatg ttggtcatac cgctggtttg gttatcggtg caggtggcac ttctagagcc    4320 gcccctttacg ccttgcacag tttaggttgc aaaaagatct tcataatcaa caggacaact    4380
tcgaaattga agccattaat agagtcactt ccatctgaat tcaacattat tggaatagag    4440
tccactaaat ctatagaaga gattaaggaa cacgttggcg ttgctgtcag ctgtgtacca    4500
gccgacaaac cattagatga cgaacttta agtaagctgg agagattcct tgtgaaaggt     4560
gcccatgctg cttttgtacc aaccttattg gaagccgcat acaaaccaag cgttactccc    4620
gttatgacaa tttcacaaga caaatatcaa tggcacgttg tccctggatc acaaatgtta    4680
gtacaccaag gtgtagctca gtttgaaaag tggacaggat tcaagggccc tttcaaggcc    4740 attttttgatg ccgttacgaa agagtag                                       4767
```

<210> SEQ ID NO 82
<211> LENGTH: 1588
<212> TYPE: PRT
<213> ORGANISM: Saccharomyces cerevisiae

<400> SEQUENCE: 82

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
                20                  25                  30

Cys Pro Ser Ser Thr Tyr Val Ile Cys Asn Asp Thr Asn Leu Ser Lys
            35                  40                  45

Val Pro Tyr Tyr Gln Gln Leu Val Leu Glu Phe Lys Ala Ser Leu Pro
        50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
                100                 105                 110

Gly Asp Met Ile Gly Phe Val Ala Ser Thr Phe Met Arg Gly Val Arg
            115                 120                 125

Val Val Gln Val Pro Thr Ser Leu Leu Ala Met Val Asp Ser Ser Ile
        130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175
```

```
Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590
```

```
Tyr Ala Glu Glu Pro Val Thr Leu Ala Leu Val Gly Lys Pro Ile
            595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Ile Pro
625                 630                 635                 640

Lys Gly His Tyr Ile Asn Pro Ser Glu Tyr Val Ile Glu Ser Asp Ala
            645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
    675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
            725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
    755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
            805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
    835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
            885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
            915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
            965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe Leu Gln Ser
            995                 1000                1005

Asp Pro  Ser Arg Pro Ala Tyr  Val Glu Glu Ile Arg  Glu Val Trp
```

```
                1010                1015                1020
Asn Arg Arg Glu Gly Trp Tyr Lys Glu Cys Ser Asn Phe Ser Phe
        1025                1030                1035

Phe Ala Pro His Cys Ser Ala Glu Ala Glu Phe Gln Ala Leu Arg
        1040                1045                1050

Arg Ser Phe Ser Lys Tyr Ile Ala Thr Ile Thr Gly Val Arg Glu
        1055                1060                1065

Ile Glu Ile Pro Ser Gly Arg Ser Ala Phe Val Cys Leu Thr Phe
        1070                1075                1080

Asp Asp Leu Thr Glu Gln Thr Glu Asn Leu Thr Pro Ile Cys Tyr
        1085                1090                1095

Gly Cys Glu Ala Val Glu Val Arg Val Asp His Leu Ala Asn Tyr
        1100                1105                1110

Ser Ala Asp Phe Val Ser Lys Gln Leu Ser Ile Leu Arg Lys Ala
        1115                1120                1125

Thr Asp Ser Ile Pro Ile Ile Phe Thr Val Arg Thr Met Lys Gln
        1130                1135                1140

Gly Gly Asn Phe Pro Asp Glu Glu Phe Lys Thr Leu Arg Glu Leu
        1145                1150                1155

Tyr Asp Ile Ala Leu Lys Asn Gly Val Glu Phe Leu Asp Leu Glu
        1160                1165                1170

Leu Thr Leu Pro Thr Asp Ile Gln Tyr Glu Val Ile Asn Lys Arg
        1175                1180                1185

Gly Asn Thr Lys Ile Ile Gly Ser His His Asp Phe Gln Gly Leu
        1190                1195                1200

Tyr Ser Trp Asp Asp Ala Glu Trp Glu Asn Arg Phe Asn Gln Ala
        1205                1210                1215

Leu Thr Leu Asp Val Asp Val Val Lys Phe Val Gly Thr Ala Val
        1220                1225                1230

Asn Phe Glu Asp Asn Leu Arg Leu Glu His Phe Arg Asp Thr His
        1235                1240                1245

Lys Asn Lys Pro Leu Ile Ala Val Asn Met Thr Ser Lys Gly Ser
        1250                1255                1260

Ile Ser Arg Val Leu Asn Asn Val Leu Thr Pro Val Thr Ser Asp
        1265                1270                1275

Leu Leu Pro Asn Ser Ala Ala Pro Gly Gln Leu Thr Val Ala Gln
        1280                1285                1290

Ile Asn Lys Met Tyr Thr Ser Met Gly Gly Ile Glu Pro Lys Glu
        1295                1300                1305

Leu Phe Val Val Gly Lys Pro Ile Gly His Ser Arg Ser Pro Ile
        1310                1315                1320

Leu His Asn Thr Gly Tyr Glu Ile Leu Gly Leu Pro His Lys Phe
        1325                1330                1335

Asp Lys Phe Glu Thr Glu Ser Ala Gln Leu Val Lys Glu Lys Leu
        1340                1345                1350

Leu Asp Gly Asn Lys Asn Phe Gly Gly Ala Ala Val Thr Ile Pro
        1355                1360                1365

Leu Lys Leu Asp Ile Met Gln Tyr Met Asp Glu Leu Thr Asp Ala
        1370                1375                1380

Ala Lys Val Ile Gly Ala Val Asn Thr Val Ile Pro Leu Gly Asn
        1385                1390                1395

Lys Lys Phe Lys Gly Asp Asn Thr Asp Trp Leu Gly Ile Arg Asn
        1400                1405                1410
```

```
Ala Leu Ile Asn Asn Gly Val Pro Glu Tyr Val Gly His Thr Ala
    1415                1420                1425

Gly Leu Val Ile Gly Ala Gly Gly Thr Ser Arg Ala Ala Leu Tyr
    1430                1435                1440

Ala Leu His Ser Leu Gly Cys Lys Lys Ile Phe Ile Ile Asn Arg
    1445                1450                1455

Thr Thr Ser Lys Leu Lys Pro Leu Ile Glu Ser Leu Pro Ser Glu
    1460                1465                1470

Phe Asn Ile Ile Gly Ile Glu Ser Thr Lys Ser Ile Glu Glu Ile
    1475                1480                1485

Lys Glu His Val Gly Val Ala Val Ser Cys Val Pro Ala Asp Lys
    1490                1495                1500

Pro Leu Asp Asp Glu Leu Leu Ser Lys Leu Glu Arg Phe Leu Val
    1505                1510                1515

Lys Gly Ala His Ala Ala Phe Val Pro Thr Leu Leu Glu Ala Ala
    1520                1525                1530

Tyr Lys Pro Ser Val Thr Pro Val Met Thr Ile Ser Gln Asp Lys
    1535                1540                1545

Tyr Gln Trp His Val Val Pro Gly Ser Gln Met Leu Val His Gln
    1550                1555                1560

Gly Val Ala Gln Phe Glu Lys Trp Thr Gly Phe Lys Gly Pro Phe
    1565                1570                1575

Lys Ala Ile Phe Asp Ala Val Thr Lys Glu
    1580                1585
```

<210> SEQ ID NO 83
<211> LENGTH: 1080
<212> TYPE: DNA
<213> ORGANISM: Escherichia coli W3110

<400> SEQUENCE: 83

```
atggagagga ttgtcgttac tctcggggaa cgtagttacc caattaccat cgcatctggt    60
ttgtttaatg aaccagcttc attcttaccg ctgaaatcgg gcgagcaggt catgttggtc   120
accaacgaaa ccctggctcc tctgtatctc gataaggtcc gcggcgtact tgaacaggcg   180
ggtgttaacg tcgatagcgt tatcctccct gacggcgagc agtataaaag cctggctgta   240
ctcgataccg tctttacggc gttgttacaa aaaccgcatg gtcgcgatac tacgctggtg   300
gcgcttggcg gcggcgtagt gggcgatctg accggcttcg cggcggcgag ttatcagcgc   360
ggtgtccgtt tcattcaagt cccgacgacg ttactgtcgc aggtcgattc ctccgttggc   420
ggcaaaactg cggtcaacca tccgctcggt aaaaacatga ttggcgcgtt ctaccaacct   480
gcttcagtgg tggtggatct cgactgtctg aaaacgcttc cccgcgtgaa gttagcgtcg   540
gggctggcag aagtcatcaa atacggcatt attcttgacg gtgcgttttt taactggctg   600
gaagagaatc tggatgcgtt gttgcgtctg acggtccgg caatggcgta ctgtattcgc   660
cgttgttgtg aactgaaggc agaagttgtc gccgccgacg agcgcgaaac cgggttacgt   720
gctttactga atctgggaca cacctttggt catgccattg aagctgaaat ggggtatggc   780
aattggttac atggtgaagc ggtcgctgcg ggtatggtga tggcggcgcg acgtcggaa    840 cgtctcgggc agtttagttc tgccgaaacg cagcgtatta accctgct caagcgggct   900 gggttaccgg tcaatgggcc gcgcgaaatg tccgcgcagg cgtatttacc gcatatgctg   960
cgtgacaaga aagtccttgc gggagagatg cgcttaattc ttccgttggc aattggtaag  1020
```
agtgaagttc gcagcggcgt tcgcacgag cttgttctta acgccattgc cgattgtcaa    1080

<210> SEQ ID NO 84
<211> LENGTH: 362
<212> TYPE: PRT
<213> ORGANISM: Escherichia coli W3110

<400> SEQUENCE: 84

```
Met Glu Arg Ile Val Val Thr Leu Gly Glu Arg Ser Tyr Pro Ile Thr
 1               5                  10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
    50                  55                  60

Asp Ser Val Ile Leu Pro Asp Gly Glu Gln Tyr Lys Ser Leu Ala Val
65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ala Ser Tyr Gln Arg Gly Val Arg Phe Ile Gln Val Pro
        115                 120                 125

Thr Thr Leu Leu Ser Gln Val Asp Ser Ser Val Gly Gly Lys Thr Ala
    130                 135                 140

Val Asn His Pro Leu Gly Lys Asn Met Ile Gly Ala Phe Tyr Gln Pro
145                 150                 155                 160

Ala Ser Val Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
            180                 185                 190

Asp Gly Ala Phe Phe Asn Trp Leu Glu Glu Asn Leu Asp Ala Leu Leu
        195                 200                 205

Arg Leu Asp Gly Pro Ala Met Ala Tyr Cys Ile Arg Arg Cys Cys Glu
    210                 215                 220

Leu Lys Ala Glu Val Val Ala Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255

Met Gly Tyr Gly Asn Trp Leu His Gly Glu Ala Val Ala Ala Gly Met
            260                 265                 270

Val Met Ala Ala Arg Thr Ser Glu Arg Leu Gly Gln Phe Ser Ser Ala
        275                 280                 285

Glu Thr Gln Arg Ile Ile Thr Leu Leu Lys Arg Ala Gly Leu Pro Val
    290                 295                 300

Asn Gly Pro Arg Glu Met Ser Ala Gln Ala Tyr Leu Pro His Met Leu
305                 310                 315                 320

Arg Asp Lys Lys Val Leu Ala Gly Glu Met Arg Leu Ile Leu Pro Leu
                325                 330                 335

Ala Ile Gly Lys Ser Glu Val Arg Ser Gly Val Ser His Glu Leu Val
            340                 345                 350

Leu Asn Ala Ile Ala Asp Cys Gln Ser Ala
        355                 360
```

<210> SEQ ID NO 85
<211> LENGTH: 2247
<212> TYPE: DNA
<213> ORGANISM: Anabaena variabilis ATCC29413

<400> SEQUENCE: 85

| | | | | | |
|---|---|---|---|---|---|
| atgagtatcg | tccaagcaaa | gtttgaagct | aaggaaacat | cttttcatgt | agaaggttac | 60 |
| gaaaagattg | agtatgattt | ggtgtatgta | gatggtattt | ttgaaatcca | gaattctgca | 120 |
| ctagcagatg | tatatcaagg | ttttggacga | tgcttggcga | ttgtagatgc | taacgtcagt | 180 |
| cggttgtatg | gtaatcaaat | tcaggcatat | ttccagtatt | atggtataga | actgaggcta | 240 |
| tttcctatta | ccattactga | accagataag | actattcaaa | ctttcgagag | agttatagat | 300 |
| gtctttgcag | atttcaaatt | agtccgcaaa | gaaccagtat | tagtcgtggg | tggcggttta | 360 |
| attacagatg | ttgtcggctt | tgcttgttct | acatatcgtc | gcagcagcaa | ttacatccgc | 420 |
| attcctacta | cattgattgg | attaattgat | gccagtgtag | caattaaggt | agcagttaat | 480 |
| catcgcaaac | tgaaaaaccg | tttgggtgct | tatcatgctt | ctcgcaaagt | attttttagat | 540 |
| ttctccttgt | tgcgtactct | ccctacagac | caagtacgta | acgggatggc | ggaattggta | 600 |
| aaaatcgctg | tagtagcgca | tcaagaagtt | tttgaattgt | tggagaagta | cggcgaagaa | 660 |
| ttactacgta | ctcattttgg | caatatagat | gcaactccag | agattaaaga | aatagcccat | 720 |
| cgtttgactt | acaaagctat | ccataagatg | ttggaattgg | aagttcccaa | cctgcatgag | 780 |
| ttagacctag | atagggtgat | tgcttacggt | cacacttgga | gtcccacctt | ggaacttgcg | 840 |
| cctcgtctac | ccatgttcca | cggacacgcc | gttaatgtag | atatggcttt | ctcggcaacg | 900 |
| atcgccgccc | gtagaggata | tattacaatt | gcagaacgcg | atcgtatttt | aggattaatg | 960 |
| agtcgcgttg | gtctatccct | cgaccatccc | atgttggata | tagatatttt | gtggcgtggt | 1020 |
| actgaatcta | tcacattaac | tcgtgatggt | ttgttaagag | ctgctatgcc | aaaacccatt | 1080 |
| ggtgattgtg | tcttcgtcaa | tgacctgaca | agagaagaat | tagcagccgc | attagctgac | 1140 |
| cacaaagaac | tttgtaccag | ttatccccgt | ggtggtaagg | tgtggatgt | gtatcccgtt | 1200 |
| tatcaaaaag | aattaatcgg | gagtgttaaa | taatgacttt | tttgaattca | aaatgcaaaa | 1260 |
| tactccacgg | atacactgcg | cgagcgcggt | agcatttctg | ttcgcggagc | gtcccgtagg | 1320 |
| gaaagagaag | gctacgcaaa | taatcggaca | ctaattgtct | ttaattttga | attttgaatt | 1380 |
| ttgaattttg | aattggagcg | aagcgacttg | acaaatgtga | ttgtccaacc | aacagctaga | 1440 |
| cctgttacac | cattgggaat | tttaaccaag | cagttagaag | ccatagtcca | agaggttaag | 1500 |
| caacatccag | atttacctgg | ggaattgata | gcaaacatcc | atcaggcttg | gcgtttagcc | 1560 |
| gcaggtatag | acccttattt | ggaagaatgc | accactccag | aatctcctga | actcgctgca | 1620 |
| ttggcaaaaa | ccacagccac | cgaagcctgg | ggagaacact | tccacggagg | tacaaccgtc | 1680 |
| cgtcctctag | aacaagagat | gctttctggt | catatcgaag | acaaaccctt | aaagatgttt | 1740 |
| gttcacatga | ccaaagctaa | aaaagtctta | gaaattggga | tgtttaccgg | ttattcggcg | 1800 |
| ctggcgatgg | cggaagcatt | accagaggat | ggactgcttg | tggcttgtga | agttgaccct | 1860 |
| tacgcggcgg | aaattggaca | gaaagccttt | caacaatctc | cccacggtgg | aaagattcgt | 1920 |
| gtggaattgg | atgcagcctt | agcaactctt | gataagttag | cagaagctgg | ggagtctttt | 1980 |
| gacttggtat | ttatcgacgc | agataaaaaa | gagtatgtag | cctattttca | caagttgcta | 2040 |
| ggtagcagtt | tgttagcacc | agatggcttt | atttgtgtag | ataacacctt | attacaaggg | 2100 |
| gaagtttatc | taccagcaga | ggaacgtagc | gtcaatggtg | aagcgatcgc | gcaatttaat | 2160 |

```
catacagtag ctatagaccc ccgtgtagaa caggttttgt tgccgttgcg agatggttta    2220
acaattatcc gcagaataca accttaa                                       2247
```

<210> SEQ ID NO 86
<211> LENGTH: 820
<212> TYPE: PRT
<213> ORGANISM: Anabaena variabilis ATCC29413

<400> SEQUENCE: 86

```
Met Ser Ile Val Gln Ala Lys Phe Glu Ala Lys Glu Thr Ser Phe His
1               5                  10                  15

Val Glu Gly Tyr Glu Lys Ile Glu Tyr Asp Leu Val Tyr Val Asp Gly
            20                  25                  30

Ile Phe Glu Ile Gln Asn Ser Ala Leu Ala Asp Val Tyr Gln Gly Phe
        35                  40                  45

Gly Arg Cys Leu Ala Ile Val Asp Ala Asn Val Ser Arg Leu Tyr Gly
    50                  55                  60

Asn Gln Ile Gln Ala Tyr Phe Gln Tyr Tyr Gly Ile Glu Leu Arg Leu
65                  70                  75                  80

Phe Pro Ile Thr Ile Thr Glu Pro Asp Lys Thr Ile Gln Thr Phe Glu
                85                  90                  95

Arg Val Ile Asp Val Phe Ala Asp Phe Lys Leu Val Arg Lys Glu Pro
            100                 105                 110

Val Leu Val Val Gly Gly Leu Ile Thr Asp Val Val Gly Phe Ala
        115                 120                 125

Cys Ser Thr Tyr Arg Arg Ser Ser Asn Tyr Ile Arg Ile Pro Thr Thr
    130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
            180                 185                 190

Arg Asn Gly Met Ala Glu Leu Val Lys Ile Ala Val Ala His Gln
        195                 200                 205

Glu Val Phe Glu Leu Leu Glu Lys Tyr Gly Glu Glu Leu Leu Arg Thr
    210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
            260                 265                 270

Trp Ser Pro Thr Leu Glu Leu Ala Pro Arg Leu Pro Met Phe His Gly
        275                 280                 285

His Ala Val Asn Val Asp Met Ala Phe Ser Ala Thr Ile Ala Ala Arg
    290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

Leu Trp Arg Gly Thr Glu Ser Ile Thr Leu Thr Arg Asp Gly Leu Leu
            340                 345                 350
```

```
Arg Ala Ala Met Pro Lys Pro Ile Gly Asp Cys Val Phe Val Asn Asp
            355                 360                 365
Leu Thr Arg Glu Glu Leu Ala Ala Leu Ala Asp His Lys Glu Leu
    370                 375                 380
Cys Thr Ser Tyr Pro Arg Gly Gly Gly Val Asp Val Tyr Pro Val
385                 390                 395                 400
Tyr Gln Lys Glu Leu Ile Gly Ser Val Lys Met Ser Ile Val Gln Ala
                405                 410                 415
Lys Phe Glu Ala Lys Glu Thr Ser Phe His Val Glu Gly Tyr Glu Lys
            420                 425                 430
Ile Glu Tyr Asp Leu Val Tyr Val Asp Gly Ile Phe Glu Ile Gln Asn
            435                 440                 445
Ser Ala Leu Ala Asp Val Tyr Gln Gly Phe Gly Arg Cys Leu Ala Ile
            450                 455                 460
Val Asp Ala Asn Val Ser Arg Leu Tyr Gly Asn Gln Ile Gln Ala Tyr
465                 470                 475                 480
Phe Gln Tyr Tyr Gly Ile Glu Leu Arg Leu Phe Pro Ile Thr Ile Thr
                485                 490                 495
Glu Pro Asp Lys Thr Ile Gln Thr Phe Glu Arg Val Ile Asp Val Phe
            500                 505                 510
Ala Asp Phe Lys Leu Val Arg Lys Glu Pro Val Leu Val Val Gly Gly
            515                 520                 525
Gly Leu Ile Thr Asp Val Val Gly Phe Ala Cys Ser Thr Tyr Arg Arg
            530                 535                 540
Ser Ser Asn Tyr Ile Arg Ile Pro Thr Thr Leu Ile Gly Leu Ile Asp
545                 550                 555                 560
Ala Ser Val Ala Ile Lys Val Ala Val Asn His Arg Lys Leu Lys Asn
                565                 570                 575
Arg Leu Gly Ala Tyr His Ala Ser Arg Lys Val Phe Leu Asp Phe Ser
            580                 585                 590
Leu Leu Arg Thr Leu Pro Thr Asp Gln Val Arg Asn Gly Met Ala Glu
            595                 600                 605
Leu Val Lys Ile Ala Val Ala His Gln Glu Val Phe Glu Leu Leu
610                 615                 620
Glu Lys Tyr Gly Glu Glu Leu Leu Arg Thr His Phe Gly Asn Ile Asp
625                 630                 635                 640
Ala Thr Pro Glu Ile Lys Glu Ile Ala His Arg Leu Thr Tyr Lys Ala
                645                 650                 655
Ile His Lys Met Leu Glu Leu Glu Val Pro Asn Leu His Glu Leu Asp
            660                 665                 670
Leu Asp Arg Val Ile Ala Tyr Gly His Thr Trp Ser Pro Thr Leu Glu
            675                 680                 685
Leu Ala Pro Arg Leu Pro Met Phe His Gly His Ala Val Asn Val Asp
            690                 695                 700
Met Ala Phe Ser Ala Thr Ile Ala Ala Arg Gly Tyr Ile Thr Ile
705                 710                 715                 720
Ala Glu Arg Asp Arg Ile Leu Gly Leu Met Ser Arg Val Gly Leu Ser
                725                 730                 735
Leu Asp His Pro Met Leu Asp Ile Asp Ile Leu Trp Arg Gly Thr Glu
            740                 745                 750
Ser Ile Thr Leu Thr Arg Asp Gly Leu Leu Arg Ala Ala Met Pro Lys
            755                 760                 765
Pro Ile Gly Asp Cys Val Phe Val Asn Asp Leu Thr Arg Glu Glu Leu
```

```
             770              775              780
Ala Ala Ala Leu Ala Asp His Lys Glu Leu Cys Thr Ser Tyr Pro Arg
785                 790                 795                 800

Gly Gly Glu Gly Val Asp Val Tyr Pro Val Tyr Gln Lys Glu Leu Ile
                805                 810                 815

Gly Ser Val Lys
        820

<210> SEQ ID NO 87
<211> LENGTH: 3638
<212> TYPE: DNA
<213> ORGANISM: Anabaena variabilis ATCC29413

<400> SEQUENCE: 87
atgagtatcg tccaagcaaa gtttgaagct aaggaaacat cttttcatgt agaaggttac      60
gaaaagattg agtatgattt ggtgtatgta gatggtattt ttgaaatcca gaattctgca     120
ctagcagatg tatatcaagg ttttggacga tgcttggcga ttgtagatgc taacgtcagt     180
cggttgtatg gtaatcaaat tcaggcatat ttccagtatt atggtataga actgaggcta     240
tttcctatta ccattactga accagataag actattcaaa ctttcgagag agttatagat     300
gtctttgcag atttcaaatt agtccgcaaa gaaccagtat tagtcgtggg tggcggttta     360
attacagatg ttgtcggctt tgcttgttct acatatcgtc gcagcagcaa ttacatccgc     420
attcctacta cattgattgg attaattgat gccagtgtag caattaaggt agcagttaat     480
catcgcaaac tgaaaaaccg tttgggtgct tatcatgctt ctcgcaaagt attttttagat    540 ttctccttgt tgcgtactct ccctacagac caagtacgta acgggatggc ggaattggta     600
aaaatcgctg tagtagcgca tcaagaagtt tttgaattgt tggagaagta cggcgaagaa     660
ttactacgta ctcattttgg caatatagat gcaactccag agattaaaga aatagcccat     720
cgtttgactt acaaagctat ccataagatg ttggaattgg aagttcccaa cctgcatgag     780
ttagacctag ataggggtgat tgcttacggt cacacttgga gtcccacctt ggaacttgcg    840
cctcgtctac ccatgttcca cggacacgcc gttaatgtag atatggcttt ctcggcaacg     900
atcgccgccc gtagaggata tattacaatt gcagaacgcg atcgtatttt aggattaatg     960
agtcgcgttg gtctatccct cgaccatccc atgttggata tagatatttt gtggcgtggt    1020
actgaatcta tcacattaac tcgtgatggt ttgttaagag ctgctatgcc aaaacccatt    1080
ggtgattgtg tcttcgtcaa tgacctgaca agagaagaat tagcagccgc attagctgac    1140
cacaaagaac tttgtaccag ttatccccgt ggtggtgaag tgtgtgatgt gtatcccgtt    1200
tatcaaaaag aattaatcgg gagtgttaaa taatgacttt tttgaattca aaatgcaaaa    1260
tactccacgg atacactgcg cgagcgcggt agcatttctg ttcgcggagc gtcccgtagg    1320
gaaagagaag gctacgcaaa taatcggaca ctaattgtct ttaattttga attttgaatt    1380
ttgaattttg aattggagcg aagcgacttg acaaatgtga ttgtccaacc aacagctaga    1440
cctgttacac cattgggaat tttaaccaag cagttagaag ccatagtcca agaggttaag    1500
caacatccag atttacctgg ggaattgata gcaaacatcc atcaggcttg gcgtttagcc    1560
gcaggtatag acccttattt ggaagaatgc accactccag aatctcctga actcgctgca    1620
ttggcaaaaa ccacagccac cgaagcctgg ggagaacact tccacggagg tacaaccgtc    1680
cgtcctctag aacaagagat gctttctggt catatcgaag acaaaccctt aaagatgttt    1740
gttcacatga ccaaagctaa aaaagtctta gaaattggga tgtttaccgg ttattcggcg    1800
```

```
ctggcgatgg cggaagcatt accagaggat ggactgcttg tggcttgtga agttgaccct   1860
tacgcggcgg aaattggaca gaaagccttt caacaatctc cccacggtgg aaagattcgt   1920
gtggaattgg atgcagcctt agcaactctt gataagttag cagaagctgg ggagtctttt   1980
gacttggtat ttatcgacgc agataaaaaa gagtatgtag cctatttca caagttgcta    2040
ggtagcagtt tgttagcacc agatggcttt atttgtgtag ataacacctt attacaaggg   2100
gaagtttatc taccagcaga ggaacgtagc gtcaatggtg aagcgatcgc gcaatttaat   2160
catacagtag ctatagaccc ccgtgtagaa caggttttgt tgccgttgcg agatggttta   2220
acaattatcc gcagaataca accttaattg tccaatcgac tatggcacaa tcccttcccc   2280
tttcttccgc acctgctaca ccgtctcttc cttcccagac gaaaatagcc gcaattatcc   2340
aaaatatctg cactttggct ttgttattac tagcattgcc cattaatgcc accattgttt   2400
ttatatcctt gttagtcttc cgaccgcaaa aggtcaaagc agcaaacccc caaccattc    2460
ttatcagtgg cggtaagatg accaaagctt acaactagc aaggtcattc cacgcggctg    2520
gacatagagt tgtcttggtg gaaacccata atactggtt gactggtcat cgttttccc    2580
aagcagtgga taagttttac acagtccccg caccccagga caatcccaa gcttacattc    2640
aggctttggt agatatcgtc aaacaagaaa acatcgatgt ttatattccc gtcaccagtc   2700
cagtgggtag ctactacgac tcattagcca accagagtt atcccattat tgcgaagtgt   2760
ttcactttga cgcagatatt acccaaatgt tggatgataa atttgcgttg acacaaaaag   2820
cgcgatcgct tggtttatca gtacccaaat cctttaaaat tacctcacca gaacaagtca   2880
tcaacttcga tttttctgga gagacacgta atacatcct caaaagcatt ccctacgact    2940
cagtgcggcg gttggactta accaaactcc cctgtgctac tccagaggaa acagcagcat   3000
tcgtcagaag tttgccaatt actcccgaaa accgtggat tatgcaggaa tttatccccg    3060
gtaaggaatt ctgcacccat agcaccgttc ggaatgggga actcagactg cattgctgtt   3120
gcgaatcttc agccttccaa gttaattatg agaatgtaaa taacccgcaa attaccgaat   3180
gggtacagca ttttgtcaag gaactgaaac tgacaggaca gatttccttt gactttatcc   3240
aagccgaaga cggaacagtt tacgccatcg agtgtaaccc ccgcacacat tcagcaatta   3300
ccacatttta cgaccacccc caggtagcag aagcgtactt gagtcaagca ccgacgactg   3360
aaaccataca accactaacg acaagcaagc ctaccattg gacttatcac gaagtttggc    3420
gtttaactgg tatccgttct ttcacccagt tgcaaagatg gctggggaat atttggcgcg   3480
ggactgatgc gatttatcag ccagatgacc ccttaccgtt tttgatggta catcattggc   3540
aaattccccc tactgttattg aataaatttgc gtcgtcttaa aggttggacg cggatagatt   3600
tcaatattgg gaagttggtg gaattggggg gagattag                           3638
```

<210> SEQ ID NO 88
<211> LENGTH: 1099
<212> TYPE: PRT
<213> ORGANISM: Anabaena variabilis ATCC29413

<400> SEQUENCE: 88

Met Ser Ile Val Gln Ala Lys Phe Glu Ala Lys Glu Thr Ser Phe His
1               5                   10                  15

Val Glu Gly Tyr Glu Lys Ile Glu Tyr Asp Leu Val Tyr Val Asp Gly
            20                  25                  30

Ile Phe Glu Ile Gln Asn Ser Ala Leu Ala Asp Val Tyr Gln Gly Phe
        35                  40                  45

```
Gly Arg Cys Leu Ala Ile Val Asp Ala Asn Val Ser Arg Leu Tyr Gly
     50                  55                  60

Asn Gln Ile Gln Ala Tyr Phe Gln Tyr Tyr Gly Ile Glu Leu Arg Leu
 65                  70                  75                  80

Phe Pro Ile Thr Ile Thr Glu Pro Asp Lys Thr Ile Gln Thr Phe Glu
                 85                  90                  95

Arg Val Ile Asp Val Phe Ala Asp Phe Lys Leu Val Arg Lys Glu Pro
            100                 105                 110

Val Leu Val Val Gly Gly Leu Ile Thr Asp Val Gly Phe Ala
            115                 120                 125

Cys Ser Thr Tyr Arg Arg Ser Ser Asn Tyr Ile Arg Ile Pro Thr Thr
130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
            180                 185                 190

Arg Asn Gly Met Ala Glu Leu Val Lys Ile Ala Val Val Ala His Gln
            195                 200                 205

Glu Val Phe Glu Leu Leu Glu Lys Tyr Gly Glu Glu Leu Leu Arg Thr
            210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
            260                 265                 270

Trp Ser Pro Thr Leu Glu Leu Ala Pro Arg Leu Pro Met Phe His Gly
            275                 280                 285

His Ala Val Asn Val Asp Met Ala Phe Ser Ala Thr Ile Ala Ala Arg
            290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

Leu Trp Arg Gly Thr Glu Ser Ile Thr Leu Thr Arg Asp Gly Leu Leu
                340                 345                 350

Arg Ala Ala Met Pro Lys Pro Ile Gly Asp Cys Val Phe Val Asn Asp
            355                 360                 365

Leu Thr Arg Glu Glu Leu Ala Ala Ala Leu Ala Asp His Lys Glu Leu
            370                 375                 380

Cys Thr Ser Tyr Pro Arg Gly Gly Glu Gly Val Asp Val Tyr Pro Val
385                 390                 395                 400

Tyr Gln Lys Glu Leu Ile Gly Ser Val Lys Met Ser Ile Val Gln Ala
                405                 410                 415

Lys Phe Glu Ala Lys Glu Thr Ser Phe His Val Glu Gly Tyr Glu Lys
            420                 425                 430

Ile Glu Tyr Asp Leu Val Tyr Val Asp Gly Ile Phe Glu Ile Gln Asn
            435                 440                 445

Ser Ala Leu Ala Asp Val Tyr Gln Gly Phe Gly Arg Cys Leu Ala Ile
450                 455                 460

Val Asp Ala Asn Val Ser Arg Leu Tyr Gly Asn Gln Ile Gln Ala Tyr
```

```
                465                 470                 475                 480
        Phe Gln Tyr Tyr Gly Ile Glu Leu Arg Leu Phe Pro Ile Thr Ile Thr
                        485                 490                 495

Glu Pro Asp Lys Thr Ile Gln Thr Phe Glu Arg Val Ile Asp Val Phe
                        500                 505                 510

Ala Asp Phe Lys Leu Val Arg Lys Glu Pro Val Leu Val Val Gly Gly
                        515                 520                 525

Gly Leu Ile Thr Asp Val Val Gly Phe Ala Cys Ser Thr Tyr Arg Arg
                        530                 535                 540

Ser Ser Asn Tyr Ile Arg Ile Pro Thr Thr Leu Ile Gly Leu Ile Asp
        545                 550                 555                 560

Ala Ser Val Ala Ile Lys Val Ala Val Asn His Arg Lys Leu Lys Asn
                        565                 570                 575

Arg Leu Gly Ala Tyr His Ala Ser Arg Lys Val Phe Leu Asp Phe Ser
                        580                 585                 590

Leu Leu Arg Thr Leu Pro Thr Asp Gln Val Arg Asn Gly Met Ala Glu
                        595                 600                 605

Leu Val Lys Ile Ala Val Val Ala His Gln Glu Val Phe Glu Leu Leu
                        610                 615                 620

Glu Lys Tyr Gly Glu Glu Leu Leu Arg Thr His Phe Gly Asn Ile Asp
        625                 630                 635                 640

Ala Thr Pro Glu Ile Lys Glu Ile Ala His Arg Leu Thr Tyr Lys Ala
                        645                 650                 655

Ile His Lys Met Leu Glu Leu Glu Val Pro Asn Leu His Glu Leu Asp
                        660                 665                 670

Leu Asp Arg Val Ile Ala Tyr Gly His Thr Trp Ser Pro Thr Leu Glu
                        675                 680                 685

Leu Ala Pro Arg Leu Pro Met Phe His Gly His Ala Val Asn Val Asp
                        690                 695                 700

Met Ala Phe Ser Ala Thr Ile Ala Ala Arg Arg Gly Tyr Ile Thr Ile
        705                 710                 715                 720

Ala Glu Arg Asp Arg Ile Leu Gly Leu Met Ser Arg Val Gly Leu Ser
                        725                 730                 735

Leu Asp His Pro Met Leu Asp Ile Asp Ile Leu Trp Arg Gly Thr Glu
                        740                 745                 750

Ser Ile Thr Leu Thr Arg Asp Gly Leu Leu Arg Ala Ala Met Pro Lys
                        755                 760                 765

Pro Ile Gly Asp Cys Val Phe Val Asn Asp Leu Thr Arg Glu Glu Leu
                        770                 775                 780

Ala Ala Ala Leu Ala Asp His Lys Glu Leu Cys Thr Ser Tyr Pro Arg
        785                 790                 795                 800

Gly Gly Glu Gly Val Asp Val Tyr Pro Val Tyr Gln Lys Glu Leu Ile
                        805                 810                 815

Gly Ser Val Lys Met Thr Asn Val Ile Val Gln Pro Thr Ala Arg Pro
                        820                 825                 830

Val Thr Pro Leu Gly Ile Leu Thr Lys Gln Leu Glu Ala Ile Val Gln
                        835                 840                 845

Glu Val Lys Gln His Pro Asp Leu Pro Gly Glu Leu Ile Ala Asn Ile
                        850                 855                 860

His Gln Ala Trp Arg Leu Ala Ala Gly Ile Asp Pro Tyr Leu Glu Glu
        865                 870                 875                 880

Cys Thr Thr Pro Glu Ser Pro Glu Leu Ala Ala Leu Ala Lys Thr Thr
                        885                 890                 895
```

```
Ala Thr Glu Ala Trp Gly Glu His Phe His Gly Gly Thr Thr Val Arg
            900                 905                 910
Pro Leu Glu Gln Glu Met Leu Ser Gly His Ile Glu Gly Gln Thr Leu
        915                 920                 925
Lys Met Phe Val His Met Thr Lys Ala Lys Val Leu Glu Ile Gly
    930                 935                 940
Met Phe Thr Gly Tyr Ser Ala Leu Ala Met Ala Glu Ala Leu Pro Glu
945                 950                 955                 960
Asp Gly Leu Leu Val Ala Cys Glu Val Asp Pro Tyr Ala Ala Glu Ile
                965                 970                 975
Gly Gln Lys Ala Phe Gln Gln Ser Pro His Gly Lys Ile Arg Val
            980                 985                 990
Glu Leu Asp Ala Ala Leu Ala Thr Leu Asp Lys Leu Ala Glu Ala Gly
        995                 1000                1005
Glu Ser Phe Asp Leu Val Phe Ile Asp Ala Asp Lys Lys Glu Tyr
    1010                1015                1020
Val Ala Tyr Phe His Lys Leu Leu Gly Ser Ser Leu Leu Ala Pro
    1025                1030                1035
Asp Gly Phe Ile Cys Val Asp Asn Thr Leu Leu Gln Gly Glu Val
    1040                1045                1050
Tyr Leu Pro Ala Glu Glu Arg Ser Val Asn Gly Glu Ala Ile Ala
    1055                1060                1065
Gln Phe Asn His Thr Val Ala Ile Asp Pro Arg Val Glu Gln Val
    1070                1075                1080
Leu Leu Pro Leu Arg Asp Gly Leu Thr Ile Ile Arg Arg Ile Gln
    1085                1090                1095
Pro
```

<210> SEQ ID NO 89
<211> LENGTH: 1233
<212> TYPE: DNA
<213> ORGANISM: Anabaena variabilis ATCC29413

<400> SEQUENCE: 89

```
atgagtatcg tccaagcaaa gttttgaagct aaggaaacat cttttcatgt agaaggttac    60
gaaaagattg agtatgattt ggtgtatgta gatggtattt ttgaaatcca gaattctgca   120
ctagcagatg tatatcaagg ttttggacga tgcttggcga ttgtagatgc taacgtcagt   180
cggttgtatg gtaatcaaat tcaggcatat ttccagtatt atggtataga actgaggcta   240
tttcctatta ccattactga accagataag actattcaaa ctttcgagag agttatagat   300
gtctttgcag atttcaaatt agtccgcaaa gaaccagtat tagtcgtggg tggcggttta   360
attacagatg ttgtcggctt tgcttgttct acatatcgtc gcagcagcaa ttacatccgc   420
attcctacta cattgattgg attaattgat gccagtgtag caattaaggt agcagttaat   480
catcgcaaac tgaaaaaccg tttgggtgct tatcatgctt ctcgcaaagt attttttagat   540
ttctccttgt tgcgtactct ccctacagac caagtacgta acgggatggc ggaattggta   600
aaaatcgctg tagtagcgca tcaagaagtt tttgaattgt tggagaagta cggcgaagaa   660
ttactacgta ctcattttgg caatatagat gcaactccag agattaaaga aatagcccat   720
cgtttgactt acaaagctat ccataagatg ttggaattgg aagttcccaa cctgcatgag   780
ttagacctag ataggtgat tgcttacggt cacacttgga gtcccaccct tggaacttgcg   840
cctcgtctac ccatgttcca cggacacgcc gttaatgtag atatggcttt ctcggcaacg   900
```

```
atcgccgccc gtagaggata tattacaatt gcagaacgcg atcgtatttt aggattaatg      960
agtcgcgttg gtctatccct cgaccatccc atgttggata tagatatttt gtggcgtggt     1020
actgaatcta tcacattaac tcgtgatggt ttgttaagag ctgctatgcc aaaacccatt     1080
ggtgattgtg tcttcgtcaa tgacctgaca agagaagaat tagcagccgc attagctgac     1140
cacaaagaac tttgtaccag ttatccccgt ggtggtgaag gtgtggatgt gtatcccgtt     1200
tatcaaaaag aattaatcgg gagtgttaaa taa                                 1233
```

<210> SEQ ID NO 90
<211> LENGTH: 410
<212> TYPE: PRT
<213> ORGANISM: Anabaena variabilis ATCC29413

<400> SEQUENCE: 90

```
Met Ser Ile Val Gln Ala Lys Phe Glu Ala Lys Glu Thr Ser Phe His
1               5                   10                  15
Val Glu Gly Tyr Glu Lys Ile Glu Tyr Asp Leu Val Tyr Val Asp Gly
                20                  25                  30
Ile Phe Glu Ile Gln Asn Ser Ala Leu Ala Asp Val Tyr Gln Gly Phe
            35                  40                  45
Gly Arg Cys Leu Ala Ile Val Asp Ala Asn Val Ser Arg Leu Tyr Gly
        50                  55                  60
Asn Gln Ile Gln Ala Tyr Phe Gln Tyr Tyr Gly Ile Glu Leu Arg Leu
65                  70                  75                  80
Phe Pro Ile Thr Ile Thr Glu Pro Asp Lys Thr Ile Gln Thr Phe Glu
                85                  90                  95
Arg Val Ile Asp Val Phe Ala Asp Phe Lys Leu Val Arg Lys Glu Pro
            100                 105                 110
Val Leu Val Val Gly Gly Gly Leu Ile Thr Asp Val Val Gly Phe Ala
        115                 120                 125
Cys Ser Thr Tyr Arg Arg Ser Ser Asn Tyr Ile Arg Ile Pro Thr Thr
    130                 135                 140
Leu Ile Gly Leu Ile Asp Ala Ser Val Ala Ile Lys Val Ala Val Asn
145                 150                 155                 160
His Arg Lys Leu Lys Asn Arg Leu Gly Ala Tyr His Ala Ser Arg Lys
                165                 170                 175
Val Phe Leu Asp Phe Ser Leu Leu Arg Thr Leu Pro Thr Asp Gln Val
            180                 185                 190
Arg Asn Gly Met Ala Glu Leu Val Lys Ile Ala Val Val Ala His Gln
        195                 200                 205
Glu Val Phe Glu Leu Leu Glu Lys Tyr Gly Glu Glu Leu Leu Arg Thr
    210                 215                 220
His Phe Gly Asn Ile Asp Ala Thr Pro Glu Ile Lys Glu Ile Ala His
225                 230                 235                 240
Arg Leu Thr Tyr Lys Ala Ile His Lys Met Leu Glu Leu Glu Val Pro
                245                 250                 255
Asn Leu His Glu Leu Asp Leu Asp Arg Val Ile Ala Tyr Gly His Thr
            260                 265                 270
Trp Ser Pro Thr Leu Glu Leu Ala Pro Arg Leu Pro Met Phe His Gly
        275                 280                 285
His Ala Val Asn Val Asp Met Ala Phe Ser Ala Thr Ile Ala Ala Arg
    290                 295                 300
Arg Gly Tyr Ile Thr Ile Ala Glu Arg Asp Arg Ile Leu Gly Leu Met
```

| | | | | | 305 | | | | | 310 | | | | | 315 | | | | | 320 |

Ser Arg Val Gly Leu Ser Leu Asp His Pro Met Leu Asp Ile Asp Ile
                        325                     330                     335

Leu Trp Arg Gly Thr Glu Ser Ile Thr Leu Thr Arg Asp Gly Leu Leu
                        340                     345                     350

Arg Ala Ala Met Pro Lys Pro Ile Gly Asp Cys Val Phe Val Asn Asp
                        355                     360                     365

Leu Thr Arg Glu Glu Leu Ala Ala Ala Leu Ala Asp His Lys Glu Leu
                        370                     375                     380

Cys Thr Ser Tyr Pro Arg Gly Gly Glu Gly Val Asp Val Tyr Pro Val
385                     390                     395                     400

Tyr Gln Lys Glu Leu Ile Gly Ser Val Lys
                        405                     410

<210> SEQ ID NO 91
<211> LENGTH: 840
<212> TYPE: DNA
<213> ORGANISM: Anabaena variabilis ATCC29413

<400> SEQUENCE: 91
ttgacaaatg tgattgtcca accaacagct agacctgtta caccattggg aattttaacc      60
aagcagttag aagccatagt ccaagaggtt aagcaacatc agatttacc tggggaattg      120 atagcaaaca tccatcaggc ttggcgttta gccgcaggta tagaccctta tttgaagaa      180 tgcaccactc cagaatctcc tgaactcgct gcattggcaa aaaccacagc caccgaagcc      240
tggggagaac acttccacgg aggtacaacc gtccgtcctc tagaacaaga gatgctttct      300
ggtcatatcg aaggacaaac cttaaagatg tttgttcaca tgaccaaagc taaaaaagtc      360
ttagaaattg ggatgtttac cggttattcg gcgctggcga tggcggaagc attaccagag      420
gatggactgc ttgtggcttg tgaagttgac ccttacgcgg cggaaattgg acagaaagcc      480
tttcaacaat ctccccacgg tggaaagatt cgtgtggaat ggatgcagc cttagcaact      540 cttgataagt tagcagaagc tggggagtct tttgacttgg tatttatcga cgcagataaa      600
aaagagtatg tagcctattt tcacaagttg ctaggtagca gtttgttagc accagatggc      660
tttatttgtg tagataacac cttattacaa ggggaagttt atctaccagc agaggaacgt      720
agcgtcaatg tgaagcgat cgcgcaattt aatcatacag tagctataga ccccgtgta      780 gaacaggttt tgttgccgtt gcgagatggc ttaacaatta ccgcagaat acaaccttaa      840

<210> SEQ ID NO 92
<211> LENGTH: 410
<212> TYPE: PRT
<213> ORGANISM: Anabaena variabilis ATCC29413

<400> SEQUENCE: 92

Met Ser Ile Val Gln Ala Lys Phe Glu Ala Lys Glu Thr Ser Phe His
1                       5                       10                      15

Val Glu Gly Tyr Glu Lys Ile Glu Tyr Asp Leu Val Tyr Val Asp Gly
                        20                      25                      30

Ile Phe Glu Ile Gln Asn Ser Ala Leu Ala Asp Val Tyr Gln Gly Phe
                        35                      40                      45

Gly Arg Cys Leu Ala Ile Val Asp Ala Asn Val Ser Arg Leu Tyr Gly
                        50                      55                      60

Asn Gln Ile Gln Ala Tyr Phe Gln Tyr Tyr Gly Ile Glu Leu Arg Leu
65                      70                      75                      80

```
Phe Pro Ile Thr Ile Thr Glu Pro Asp Lys Thr Ile Gln Thr Phe Glu
                85                  90                  95

Arg Val Ile Asp Val Phe Ala Asp Phe Lys Leu Val Arg Lys Glu Pro
            100                 105                 110

Val Leu Val Val Gly Gly Leu Ile Thr Asp Val Gly Phe Ala
            115                 120                 125

Cys Ser Thr Tyr Arg Arg Ser Ser Asn Tyr Ile Arg Ile Pro Thr Thr
130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
            180                 185                 190

Arg Asn Gly Met Ala Glu Leu Val Lys Ile Ala Val Ala His Gln
            195                 200                 205

Glu Val Phe Glu Leu Leu Glu Lys Tyr Gly Glu Leu Leu Arg Thr
210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
            260                 265                 270

Trp Ser Pro Thr Leu Glu Leu Ala Pro Arg Leu Pro Met Phe His Gly
            275                 280                 285

His Ala Val Asn Val Asp Met Ala Phe Ser Ala Thr Ile Ala Ala Arg
290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

Leu Trp Arg Gly Thr Glu Ser Ile Thr Leu Thr Arg Asp Gly Leu Leu
            340                 345                 350

Arg Ala Ala Met Pro Lys Pro Ile Gly Asp Cys Val Phe Val Asn Asp
            355                 360                 365

Leu Thr Arg Glu Glu Leu Ala Ala Leu Ala Asp His Lys Glu Leu
370                 375                 380

Cys Thr Ser Tyr Pro Arg Gly Gly Glu Gly Val Asp Val Tyr Pro Val
385                 390                 395                 400

Tyr Gln Lys Glu Leu Ile Gly Ser Val Lys
                405                 410

<210> SEQ ID NO 93
<211> LENGTH: 840
<212> TYPE: DNA
<213> ORGANISM: Anabaena variabilis ATCC29413

<400> SEQUENCE: 93
ttgacaaatg tgattgtcca accaacagct agacctgtta caccattggg aattttaacc      60
aagcagttag aagccatagt ccaagaggtt aagcaacatc agatttacc tggggaattg     120 atagcaaaca tccatcaggc ttggcgttta gccgcaggta tagacccta tttggaagaa     180 tgcaccactc cagaatctcc tgaactcgct gcattggcaa aaaccacagc caccgaagcc    240
```

```
tggggagaac acttccacgg aggtacaacc gtccgtcctc tagaacaaga gatgctttct    300
ggtcatatcg aaggacaaac cttaaagatg tttgttcaca tgaccaaagc taaaaaagtc    360
ttagaaattg ggatgtttac cggttattcg gcgctggcga tggcggaagc attaccagag    420
gatggactgc ttgtggcttg tgaagttgac ccttacgcgg cggaaattgg acagaaagcc    480
tttcaacaat ctccccacgg tggaaagatt cgtgtggaat tggatgcagc cttagcaact    540
cttgataagt tagcagaagc tggggagtct tttgacttgg tatttatcga cgcagataaa    600
aaagagtatg tagcctattt tcacaagttg ctaggtagca gtttgttagc accagatggc    660
tttatttgtg tagataacac cttattacaa ggggaagttt atctaccagc agaggaacgt    720
agcgtcaatg gtgaagcgat cgcgcaattt aatcatacag tagctataga cccccgtgta    780
gaacaggttt tgttgccgtt gcgagatggt ttaacaatta ccgcagaat acaaccttaa    840
```

<210> SEQ ID NO 94
<211> LENGTH: 279
<212> TYPE: PRT
<213> ORGANISM: Anabaena variabilis ATCC29413

<400> SEQUENCE: 94

```
Met Thr Asn Val Ile Val Gln Pro Thr Ala Arg Pro Val Thr Pro Leu
1               5                   10                  15

Gly Ile Leu Thr Lys Gln Leu Glu Ala Ile Val Gln Glu Val Lys Gln
            20                  25                  30

His Pro Asp Leu Pro Gly Glu Leu Ile Ala Asn Ile His Gln Ala Trp
        35                  40                  45

Arg Leu Ala Ala Gly Ile Asp Pro Tyr Leu Glu Glu Cys Thr Thr Pro
    50                  55                  60

Glu Ser Pro Glu Leu Ala Ala Leu Ala Lys Thr Thr Ala Thr Glu Ala
65                  70                  75                  80

Trp Gly Glu His Phe His Gly Thr Thr Val Arg Pro Leu Glu Gln
                85                  90                  95

Glu Met Leu Ser Gly His Ile Glu Gly Gln Thr Leu Lys Met Phe Val
            100                 105                 110

His Met Thr Lys Ala Lys Lys Val Leu Glu Ile Gly Met Phe Thr Gly
        115                 120                 125

Tyr Ser Ala Leu Ala Met Ala Glu Ala Leu Pro Glu Asp Gly Leu Leu
    130                 135                 140

Val Ala Cys Glu Val Asp Pro Tyr Ala Ala Glu Ile Gly Gln Lys Ala
145                 150                 155                 160

Phe Gln Gln Ser Pro His Gly Gly Lys Ile Arg Val Glu Leu Asp Ala
                165                 170                 175

Ala Leu Ala Thr Leu Asp Lys Leu Ala Glu Ala Gly Glu Ser Phe Asp
            180                 185                 190

Leu Val Phe Ile Asp Ala Asp Lys Lys Glu Tyr Val Ala Tyr Phe His
        195                 200                 205

Lys Leu Leu Gly Ser Ser Leu Leu Ala Pro Asp Gly Phe Ile Cys Val
    210                 215                 220

Asp Asn Thr Leu Leu Gln Gly Glu Val Tyr Leu Pro Ala Glu Glu Arg
225                 230                 235                 240

Ser Val Asn Gly Glu Ala Ile Ala Gln Phe Asn His Thr Val Ala Ile
                245                 250                 255

Asp Pro Arg Val Glu Gln Val Leu Leu Pro Leu Arg Asp Gly Leu Thr
            260                 265                 270
```

Ile Ile Arg Arg Ile Gln Pro
    275

<210> SEQ ID NO 95
<211> LENGTH: 2667
<212> TYPE: DNA
<213> ORGANISM: Anabaena variabilis ATCC29413

<400> SEQUENCE: 95

| | | | | | |
|---|---|---|---|---|---|
| atgcagacta | tagattttaa | tattcgtaag | ttacttgtag | agtggaacgc | gacccacaga | 60 |
| gattatgatc | tttcccagag | tttacatgaa | ctaattgtag | ctcaagtaga | acgaacacct | 120 |
| gaggcgatcg | ctgtcacctt | tgacaagcaa | caactaactt | atcaagaact | aaatcataaa | 180 |
| gcaaaccagc | taggacatta | tttacaaaca | ttaggagtcc | agccagaaac | cctggtaggc | 240 |
| gtttgtttag | aacgttcctt | agaaatggtt | atctgtcttt | taggaatcct | caaagctggg | 300 |
| ggtgcttatg | ttcctattga | ccctgaatat | cctcaagaac | gcatagctta | tgctagaa | 360 |
| gattctcagg | tgaaggtact | actaactcaa | gaaaaattac | tcaatcaaat | tccccaccat | 420 |
| caagcacaaa | ctatctgtgt | agatagggaa | tgggagaaaa | tttccacaca | agctaatacc | 480 |
| aatcccaaaa | gtaatataaa | aacgataat | cttgcttatg | taatttacac | ctctggttcc | 540 |
| actggtaaac | caaaggtgc | aatgaacacc | cacaaggta | tctgtaatcg | cttattgtgg | 600 |
| atgcaggaag | cttatcaaat | cgattccaca | gatagcattt | tacaaaaaac | cccctttagt | 660 |
| tttgatgttt | ccgtttggga | gttcttttgg | actttattaa | ctggcgcacg | tttggtaata | 720 |
| gccaaaccag | gcggacataa | agatagtgct | tacctcatcg | atttaattac | tcaagaacaa | 780 |
| atcactacgt | tgcattttgt | cccctcaatg | ctgcaagtgt | ttttacaaaa | tcgccatgta | 840 |
| agcaaatgca | gctctctaaa | aagagttatt | tgtagcggtg | aagctttatc | tatagattta | 900 |
| caaaatagat | ttttccagca | tttgcaatgt | gaattacata | acctctatgg | cccgacagaa | 960 |
| gcagcaattg | atgtcacatt | ttggcaatgt | agaaaagata | gtaatttaaa | gagtgtacct | 1020 |
| attggtcgtc | ccattgctaa | tactcaaatt | tatattcttg | atgccgattt | acaaccagta | 1080 |
| aatattggtg | tcactggtga | atttatatt | ggtggtgtag | gggttgctcg | tggttatttg | 1140 |
| aataaagaag | aattgaccaa | agaaaaattt | attattaatc | cctttcccaa | ttctgagttt | 1200 |
| aagcgacttt | ataaaacagg | tgatttagct | cgttatttac | ccgatggaaa | tattgaatat | 1260 |
| cttggtagaa | cagattatca | agtaaaaatt | cggggtata | gaattgaaat | tggcgagatt | 1320 |
| gaaaatgttt | tatcttcaca | cccacaagtc | agagaagctg | tagtcatagc | gcgggatgat | 1380 |
| aacgctcaag | aaaaacaaat | catcgcttat | attacctata | actccatcaa | acctcagctt | 1440 |
| gataatctgc | gtgatttcct | aaaagcaagg | ctacctgatt | ttatgattcc | agccgctttt | 1500 |
| gtgatgctgg | agcatcttcc | tttaactccc | agtggtaaag | tagaccgtaa | ggcattacct | 1560 |
| aagcctgatt | tatttaatta | tagtgaacat | aattcctatg | tagcgcctcg | gaatgaagtt | 1620 |
| gaagaaaaat | tagtacaaat | ctggtcgaat | attctgcatt | tacctaaagt | aggtgtgaca | 1680 |
| gaaaactttt | tcgctattgg | tggtaattcc | ctcaaagctc | tacatttaat | ttctcaaatt | 1740 |
| gaagagttat | ttgctaaaga | gatatcctta | gcaacactt | taacaaatcc | agtaattgca | 1800 |
| gatttagcca | aggttattca | agcaaacaac | caaatccata | attcaccct | agttccaatt | 1860 |
| caaccacaag | gtaagcagca | gccttctctt | tgtatacatc | ctgctggtgg | tcatgtttta | 1920 |
| tgctatttta | aactcgcaca | atatatagga | actgaccaac | catttatgg | cttacaagct | 1980 |
| caaggatttt | atggagatga | agcacccttg | acgcgagttg | aagatatggc | tagtctctac | 2040 |

-continued

```
gtcaaaacta ttagagaatt tcaaccccaa gggccttatc gtgtcggggg gtggtcattt    2100
ggtggagtcg tagcttatga agtagcacag cagttacata gacaaggaca agaagtatct    2160
ttactagcaa tattagattc ttacgtaccg attctgctgg ataaacaaaa acccattgat    2220
gacgtttatt tagttggtgt tctctccaga gttttttggcg gtatgtttgg tcaagataat    2280
ctagtcacac ctgaagaaat agaaaattta actgtagaag aaaaaattaa ttacatcatt    2340
gataaagcac ggagcgctag aatattcccg cctggtgtag aacgtcaaaa taatcgccgt    2400
attcttgatg ttttggtggg aactttaaaa gcaacttatt cctatataag acaaccatat    2460
ccaggaaaag tcactgtatt tcgagccagg gaaaaacata ttatggctcc tgacccgacc    2520
ttagtttggg tagaattatt ttctgtaatg gcggctcaag aaattaagat tattgatgtc    2580
cctggaaacc attattcgtt tgttctagaa ccccatgtac aggttttagc acagcgttta    2640
caagattgtc tggaaaataa ttcataa                                        2667
```

<210> SEQ ID NO 96
<211> LENGTH: 888
<212> TYPE: PRT
<213> ORGANISM: Anabaena variabilis ATCC29413

<400> SEQUENCE: 96

```
Met Gln Thr Ile Asp Phe Asn Ile Arg Lys Leu Leu Val Glu Trp Asn
1               5                   10                  15

Ala Thr His Arg Asp Tyr Asp Leu Ser Gln Ser Leu His Glu Leu Ile
            20                  25                  30

Val Ala Gln Val Glu Arg Thr Pro Glu Ala Ile Ala Val Thr Phe Asp
        35                  40                  45

Lys Gln Gln Leu Thr Tyr Gln Glu Leu Asn His Lys Ala Asn Gln Leu
    50                  55                  60

Gly His Tyr Leu Gln Thr Leu Gly Val Gln Pro Glu Thr Leu Val Gly
65                  70                  75                  80

Val Cys Leu Glu Arg Ser Leu Glu Met Val Ile Cys Leu Leu Gly Ile
                85                  90                  95

Leu Lys Ala Gly Gly Ala Tyr Val Pro Ile Asp Pro Glu Tyr Pro Gln
            100                 105                 110

Glu Arg Ile Ala Tyr Met Leu Glu Asp Ser Gln Val Lys Val Leu Leu
        115                 120                 125

Thr Gln Glu Lys Leu Leu Asn Gln Ile Pro His His Gln Ala Gln Thr
    130                 135                 140

Ile Cys Val Asp Arg Glu Trp Glu Lys Ile Ser Thr Gln Ala Asn Thr
145                 150                 155                 160

Asn Pro Lys Ser Asn Ile Lys Thr Asp Asn Leu Ala Tyr Val Ile Tyr
                165                 170                 175

Thr Ser Gly Ser Thr Gly Lys Pro Lys Gly Ala Met Asn Thr His Lys
            180                 185                 190

Gly Ile Cys Asn Arg Leu Leu Trp Met Gln Ala Tyr Gln Ile Asp
        195                 200                 205

Ser Thr Asp Ser Ile Leu Gln Lys Thr Pro Phe Ser Phe Asp Val Ser
    210                 215                 220

Val Trp Glu Phe Phe Trp Thr Leu Leu Thr Gly Ala Arg Leu Val Ile
225                 230                 235                 240

Ala Lys Pro Gly Gly His Lys Asp Ser Ala Tyr Leu Ile Asp Leu Ile
                245                 250                 255

Thr Gln Glu Gln Ile Thr Thr Leu His Phe Val Pro Ser Met Leu Gln
```

```
                260                 265                 270
Val Phe Leu Gln Asn Arg His Val Ser Lys Cys Ser Ser Leu Lys Arg
            275                 280                 285

Val Ile Cys Ser Gly Glu Ala Leu Ser Ile Asp Leu Gln Asn Arg Phe
        290                 295                 300

Phe Gln His Leu Gln Cys Glu Leu His Asn Leu Tyr Gly Pro Thr Glu
305                 310                 315                 320

Ala Ala Ile Asp Val Thr Phe Trp Gln Cys Arg Lys Asp Ser Asn Leu
                325                 330                 335

Lys Ser Val Pro Ile Gly Arg Pro Ile Ala Asn Thr Gln Ile Tyr Ile
            340                 345                 350

Leu Asp Ala Asp Leu Gln Pro Val Asn Ile Gly Val Thr Gly Glu Ile
        355                 360                 365

Tyr Ile Gly Gly Val Gly Val Ala Arg Gly Tyr Leu Asn Lys Glu Glu
    370                 375                 380

Leu Thr Lys Glu Lys Phe Ile Ile Asn Pro Phe Pro Asn Ser Glu Phe
385                 390                 395                 400

Lys Arg Leu Tyr Lys Thr Gly Asp Leu Ala Arg Tyr Leu Pro Asp Gly
                405                 410                 415

Asn Ile Glu Tyr Leu Gly Arg Thr Asp Tyr Gln Val Lys Ile Arg Gly
            420                 425                 430

Tyr Arg Ile Glu Ile Gly Glu Ile Glu Asn Val Leu Ser Ser His Pro
        435                 440                 445

Gln Val Arg Glu Ala Val Val Ile Ala Arg Asp Asp Asn Ala Gln Glu
    450                 455                 460

Lys Gln Ile Ile Ala Tyr Ile Thr Tyr Asn Ser Ile Lys Pro Gln Leu
465                 470                 475                 480

Asp Asn Leu Arg Asp Phe Leu Lys Ala Arg Leu Pro Asp Phe Met Ile
                485                 490                 495

Pro Ala Ala Phe Val Met Leu Glu His Leu Pro Leu Thr Pro Ser Gly
            500                 505                 510

Lys Val Asp Arg Lys Ala Leu Pro Lys Pro Asp Leu Phe Asn Tyr Ser
        515                 520                 525

Glu His Asn Ser Tyr Val Ala Pro Arg Asn Glu Val Glu Glu Lys Leu
    530                 535                 540

Val Gln Ile Trp Ser Asn Ile Leu His Leu Pro Lys Val Gly Val Thr
545                 550                 555                 560

Glu Asn Phe Phe Ala Ile Gly Gly Asn Ser Leu Lys Ala Leu His Leu
                565                 570                 575

Ile Ser Gln Ile Glu Glu Leu Phe Ala Lys Glu Ile Ser Leu Ala Thr
            580                 585                 590

Leu Leu Thr Asn Pro Val Ile Ala Asp Leu Ala Lys Val Ile Gln Ala
        595                 600                 605

Asn Asn Gln Ile His Asn Ser Pro Leu Val Pro Ile Gln Pro Gln Gly
    610                 615                 620

Lys Gln Gln Pro Phe Phe Cys Ile His Pro Ala Gly Gly His Val Leu
625                 630                 635                 640

Cys Tyr Phe Lys Leu Ala Gln Tyr Ile Gly Thr Asp Gln Pro Phe Tyr
                645                 650                 655

Gly Leu Gln Ala Gln Gly Phe Tyr Gly Asp Glu Ala Pro Leu Thr Arg
            660                 665                 670

Val Glu Asp Met Ala Ser Leu Tyr Val Lys Thr Ile Arg Glu Phe Gln
        675                 680                 685
```

Pro Gln Gly Pro Tyr Arg Val Gly Gly Trp Ser Phe Gly Gly Val Val
    690             695                 700

Ala Tyr Glu Val Ala Gln Leu His Arg Gln Gly Gln Glu Val Ser
705             710                 715                 720

Leu Leu Ala Ile Leu Asp Ser Tyr Val Pro Ile Leu Leu Asp Lys Gln
                725                 730                 735

Lys Pro Ile Asp Asp Val Tyr Leu Val Gly Val Leu Ser Arg Val Phe
            740                 745                 750

Gly Gly Met Phe Gly Gln Asp Asn Leu Val Thr Pro Glu Glu Ile Glu
        755                 760                 765

Asn Leu Thr Val Glu Glu Lys Ile Asn Tyr Ile Ile Asp Lys Ala Arg
    770                 775                 780

Ser Ala Arg Ile Phe Pro Pro Gly Val Glu Arg Gln Asn Asn Arg Arg
785                 790                 795                 800

Ile Leu Asp Val Leu Val Gly Thr Leu Lys Ala Thr Tyr Ser Tyr Ile
                805                 810                 815

Arg Gln Pro Tyr Pro Gly Lys Val Thr Val Phe Arg Ala Arg Glu Lys
            820                 825                 830

His Ile Met Ala Pro Asp Pro Thr Leu Val Trp Val Glu Leu Phe Ser
        835                 840                 845

Val Met Ala Ala Gln Glu Ile Lys Ile Ile Asp Val Pro Gly Asn His
    850                 855                 860

Tyr Ser Phe Val Leu Glu Pro His Val Gln Val Leu Ala Gln Arg Leu
865                 870                 875                 880

Gln Asp Cys Leu Glu Asn Asn Ser
                885

<210> SEQ ID NO 97
<211> LENGTH: 1233
<212> TYPE: DNA
<213> ORGANISM: Nostoc punctiforme ATCC29133

<400> SEQUENCE: 97
atgagtaatg ttcaagcatc gtttgaagca acggaagctg aattccgcgt ggaaggttac    60
gaaaaaattg agtttagtct tgtctatgta aatggtgcat ttgatatcag taacagagaa   120
attgcagaca gctatgagaa gtttggccgt tgtctgactg tgattgatgc taatgtcaac   180
agattatatg gcaagcaaat caagtcatat tttagacact atggtattga tctgaccgta   240
gttcccattg tgattactga gcctactaaa acccttgcaa cctttgagaa aattgttgat   300 gcttttttctg actttggttt aatccgcaag gaaccagtat tagtagtggg tggtggttta   360
accactgatg tagctgggtt tgcgtgtgct gcttaccgtc gtaagagtaa ctatattcgg   420
gttccgacaa cgctgattgg tctgattgat gcaggtgtag cgattaaggt tgcagtcaac   480
catcgcaagt taaaaaatcg cttgggtgca tatcatgctc ctttgaaagt catcctcgat   540
ttctccttct tgcaaacatt accaacggct caagttcgta atgggatggc agagttggtc   600
aaaattgctg ttgtggcgaa ctctgaagtc tttgaattgt tgtatgaata tggcgaagag   660
ttgctttcca ctcactttgg atatgtgaat ggtacaaagg aactgaaagc gatcgcacat   720
aaactcaatt acgaggcaat aaaaactatg ctggagttgg aaactccaaa cttgcatgag   780
ttagacctcg atcgcgtcat tgcctacggt cacacttgga gtccgacctt agaattagct   840
ccgatgatac cgttgtttca cggtcatgcc gtcaatatag acatggcttt gtctgcaact   900
attgcggcaa gacgtggcta cattacatca ggagaacgcg atcgcatttt gagcttgatg   960

-continued

```
agtcgtatag gtttatcaat cgatcatcct ctactagatg gcgatttgct ctggtatgct    1020
acccaatcta ttagcttgac gcgagacggg aaacaacgcg cagctatgcc taaacccatt    1080
ggtgagtgct tctttgtcaa cgatttcacc cgtgaagaac tagatgcagc tttagctgaa    1140
cacaaacgtc tgtgtgctac ataccctcgt ggtggagatg gcattgacgc ttacatagaa    1200
actcaagaag aatccaaact attgggagtg tga                                  1233
```

<210> SEQ ID NO 98
<211> LENGTH: 410
<212> TYPE: PRT
<213> ORGANISM: Nostoc punctiforme ATCC29133

<400> SEQUENCE: 98

| Met<br>1 | Ser | Asn | Val | Gln<br>5 | Ala | Ser | Phe | Glu | Ala<br>10 | Thr | Glu | Ala | Glu | Phe<br>15 | Arg |
|---|---|---|---|---|---|---|---|---|---|---|---|---|---|---|---|
| Val | Glu | Gly | Tyr<br>20 | Glu | Lys | Ile | Glu | Phe<br>25 | Ser | Leu | Val | Tyr | Val<br>30 | Asn | Gly |
| Ala | Phe | Asp<br>35 | Ile | Ser | Asn | Arg | Glu<br>40 | Ile | Ala | Asp | Ser | Tyr<br>45 | Glu | Lys | Phe |
| Gly | Arg<br>50 | Cys | Leu | Thr | Val | Ile<br>55 | Asp | Ala | Asn | Val | Asn<br>60 | Arg | Leu | Tyr | Gly |
| Lys<br>65 | Gln | Ile | Lys | Ser | Tyr<br>70 | Phe | Arg | His | Tyr | Gly<br>75 | Ile | Asp | Leu | Thr | Val<br>80 |
| Val | Pro | Ile | Val | Ile<br>85 | Thr | Glu | Pro | Thr | Lys<br>90 | Thr | Leu | Ala | Thr | Phe<br>95 | Glu |
| Lys | Ile | Val | Asp<br>100 | Ala | Phe | Ser | Asp | Phe<br>105 | Gly | Leu | Ile | Arg | Lys<br>110 | Glu | Pro |
| Val | Leu | Val<br>115 | Val | Gly | Gly | Leu | Thr<br>120 | Thr | Asp | Val | Ala | Gly<br>125 | Phe | Ala |
| Cys | Ala<br>130 | Ala | Tyr | Arg | Arg | Lys<br>135 | Ser | Asn | Tyr | Ile | Arg<br>140 | Val | Pro | Thr | Thr |
| Leu<br>145 | Ile | Gly | Leu | Ile | Asp<br>150 | Ala | Gly | Val | Ala | Ile<br>155 | Lys | Val | Ala | Val | Asn<br>160 |
| His | Arg | Lys | Leu | Lys<br>165 | Asn | Arg | Leu | Gly | Ala<br>170 | Tyr | His | Ala | Pro | Leu<br>175 | Lys |
| Val | Ile | Leu | Asp<br>180 | Phe | Ser | Phe | Leu | Gln<br>185 | Thr | Leu | Pro | Thr | Ala<br>190 | Gln | Val |
| Arg | Asn | Gly<br>195 | Met | Ala | Glu | Leu | Val<br>200 | Lys | Ile | Ala | Val | Val<br>205 | Ala | Asn | Ser |
| Glu | Val<br>210 | Phe | Glu | Leu | Leu | Tyr<br>215 | Glu | Tyr | Gly | Glu | Leu<br>220 | Leu | Ser | Thr |
| His<br>225 | Phe | Gly | Tyr | Val | Asn<br>230 | Gly | Thr | Lys | Glu | Leu<br>235 | Lys | Ala | Ile | Ala | His<br>240 |
| Lys | Leu | Asn | Tyr | Glu<br>245 | Ala | Ile | Lys | Thr | Met<br>250 | Leu | Glu | Leu | Glu | Thr<br>255 | Pro |
| Asn | Leu | His | Glu<br>260 | Leu | Asp | Leu | Asp | Arg<br>265 | Val | Ile | Ala | Tyr | Gly<br>270 | His | Thr |
| Trp | Ser | Pro<br>275 | Thr | Leu | Glu | Leu | Ala<br>280 | Pro | Met | Ile | Pro | Leu<br>285 | Phe | His | Gly |
| His | Ala<br>290 | Val | Asn | Ile | Asp | Met<br>295 | Ala | Leu | Ser | Ala | Thr<br>300 | Ile | Ala | Ala | Arg |
| Arg<br>305 | Gly | Tyr | Ile | Thr | Ser<br>310 | Gly | Glu | Arg | Asp | Arg<br>315 | Ile | Leu | Ser | Leu | Met<br>320 |

Ser Arg Ile Gly Leu Ser Ile Asp His Pro Leu Leu Asp Gly Asp Leu
            325                 330                 335

Leu Trp Tyr Ala Thr Gln Ser Ile Ser Leu Thr Arg Asp Gly Lys Gln
            340                 345                 350

Arg Ala Ala Met Pro Lys Pro Ile Gly Glu Cys Phe Phe Val Asn Asp
            355                 360                 365

Phe Thr Arg Glu Glu Leu Asp Ala Ala Leu Ala Glu His Lys Arg Leu
            370                 375                 380

Cys Ala Thr Tyr Pro Arg Gly Gly Asp Gly Ile Asp Ala Tyr Ile Glu
385                 390                 395                 400

Thr Gln Glu Glu Ser Lys Leu Leu Gly Val
            405                 410

<210> SEQ ID NO 99
<211> LENGTH: 834
<212> TYPE: DNA
<213> ORGANISM: Nostoc punctiforme ATCC29133

<400> SEQUENCE: 99
atgaccagta ttttaggacg agataccgca agaccaataa cgccacatag cattctggta      60
gcacagctac aaaaaaccct cagaatggca gaggaaagta atattccttc agagatactg     120
acttctctgc gccaagggtt gcaattagca gcaggtttag atccctatct ggatgattgc     180
actcccctg aatcgaccgc attgacagca ctagcgcaga agacaagcat tgaagactgg     240
agtaaacgct tcagtgatgg tgaaacagtg cgtcaattag agcaagaaat gctctcagga     300
catcttgaag acaaacact aaagatgttt gtgcatatca ctaaggctaa agcatccta      360
gaagtgggaa tgttcacagg atattcagct ttggcaatgg cagaggcgtt accagatgat     420
gggcgactga ttgcttgtga agtagactcc tatgtggccg agtttgctca aacttgcttt     480
caagagtctc cccacggccg caagattgtt gtagaagtgg cacctgcact agagacgctg     540
cacaagctgg tggctaaaaa agaatccttt gatctgatct tcattgatgc ggataaaaag     600
gagtatatag aatacttcca aattatcttg gatagccatt tactagctcc cgacggatta     660
atctgtgtag ataatacttt gttgcaagga caagtttacc tgccatcaga acagcgtaca     720
gccaatggtg aagcgatcgc tcaattcaac cgcattgtcg ccgcagatcc tcgtgtagag     780
caagttctgt tacccatacg agatggtata accctgatta gacgcttggt ataa           834

<210> SEQ ID NO 100
<211> LENGTH: 277
<212> TYPE: PRT
<213> ORGANISM: Nostoc punctiforme ATCC29133

<400> SEQUENCE: 100

Met Thr Ser Ile Leu Gly Arg Asp Thr Ala Arg Pro Ile Thr Pro His
1               5                   10                  15

Ser Ile Leu Val Ala Gln Leu Gln Lys Thr Leu Arg Met Ala Glu Glu
            20                  25                  30

Ser Asn Ile Pro Ser Glu Ile Leu Thr Ser Leu Arg Gln Gly Leu Gln
        35                  40                  45

Leu Ala Ala Gly Leu Asp Pro Tyr Leu Asp Asp Cys Thr Thr Pro Glu
    50                  55                  60

Ser Thr Ala Leu Thr Ala Leu Ala Gln Lys Thr Ser Ile Glu Asp Trp
65                  70                  75                  80

Ser Lys Arg Phe Ser Asp Gly Glu Thr Val Arg Gln Leu Glu Gln Glu
            85                  90                  95

```
Met Leu Ser Gly His Leu Glu Gly Gln Thr Leu Lys Met Phe Val His
                100                 105                 110

Ile Thr Lys Ala Lys Ser Ile Leu Glu Val Gly Met Phe Thr Gly Tyr
            115                 120                 125

Ser Ala Leu Ala Met Ala Glu Ala Leu Pro Asp Asp Gly Arg Leu Ile
        130                 135                 140

Ala Cys Glu Val Asp Ser Tyr Val Ala Glu Phe Ala Gln Thr Cys Phe
145                 150                 155                 160

Gln Glu Ser Pro His Gly Arg Lys Ile Val Glu Val Ala Pro Ala
                165                 170                 175

Leu Glu Thr Leu His Lys Leu Val Ala Lys Lys Glu Ser Phe Asp Leu
                180                 185                 190

Ile Phe Ile Asp Ala Asp Lys Lys Glu Tyr Ile Glu Tyr Phe Gln Ile
            195                 200                 205

Ile Leu Asp Ser His Leu Leu Ala Pro Asp Gly Leu Ile Cys Val Asp
        210                 215                 220

Asn Thr Leu Leu Gln Gly Gln Val Tyr Leu Pro Ser Glu Gln Arg Thr
225                 230                 235                 240

Ala Asn Gly Glu Ala Ile Ala Gln Phe Asn Arg Ile Val Ala Ala Asp
                245                 250                 255

Pro Arg Val Glu Gln Val Leu Leu Pro Ile Arg Asp Gly Ile Thr Leu
                260                 265                 270

Ile Arg Arg Leu Val
            275

<210> SEQ ID NO 101
<211> LENGTH: 1386
<212> TYPE: DNA
<213> ORGANISM: Nostoc punctiforme ATCC29133

<400> SEQUENCE: 101
atggcacaat caatctcttt atctcttcct caatccacaa cgccatcaaa gggtgtgagg       60
ctaaaaatag cagctctact gaagactatc gggactctaa tactactgct gatagccttg      120
ccgcttaatg ctttgatagt attgatatct ctgatgtgta ggccgtttac aaaaaaacct      180
gccgtagcca ctcatcccca gaatatcttg tcagtggcg gcaaaatgac caaagcattg       240
caacttgccc gctccttcca tgcagccgga cacagagtta ttctgattga aggtcataaa      300
tactggttat cagggcatag attctcaaat tctgtgagtc gtttttatac agttcctgca      360
ccacaagacg acccagaagg ctatacccaa gcgctattgg aaattgtcaa cgagagaag      420 attgacgttt atgtacccgt atgcagccct gtagctagtt attacgactc tttggcaaag      480
tctgcactat cagaatattg tgaggttttt cactttgatg ctgatataac caagatgctg      540
gatgataaat ttgcctttac cgatcgggcg cgatcgcttg gtttatcagc ccgaaatct       600 tttaaaatta ccgatcctga acaagttatc aacttcgatt ttagtaaaga gacgcgcaaa      660
tatattctta agagtatttc ttacgactca gttcgccgct aaatttaac caaacttcct      720 tgtgataccc cagaagagac agcagcgttt gtcaagagtt acccatcag cccagaaaaa      780 ccttggatta tgcaagaatt tattcctggg aaagaattat gcacccatag cacagtccga      840
gacggcgaat taaggttgca ttgctgttca aattcttcag cgtttcagat taactatgaa      900
aatgtcgaaa atccccaaat tcaagaatgg gtacaacatt tcgtcaaaag tttacggctg      960
actggacaaa tatctcttga ctttatccaa gctgaagatg gtacagctta tgccattgaa     1020
```

```
tgtaatcctc gcacccattc ggcgatcaca atgttctaca atcacccagg tgttgcagaa    1080
gcctatcttg gtaaaactcc tctagctgca cctttggaac tcttgcaga tagcaagccc     1140 acttactgga tatatcacga aatctggcga ttgactggga ttcgctctgg acaacaatta   1200
caaacttggt ttgggagatt agtcagaggt acagatgcca tttatcgcct ggacgatccg   1260
ataccatttt taactttgca ccattggcag attactttac ttttgctaca aaatttgcaa   1320
cgactcaaag gttgggtaaa gatcgatttt aatatcggta aactcgtgga attaggggc    1380 gactaa                                                               1386
```

<210> SEQ ID NO 102
<211> LENGTH: 461
<212> TYPE: PRT
<213> ORGANISM: Nostoc punctiforme ATCC29133

<400> SEQUENCE: 102

```
Met Ala Gln Ser Ile Ser Leu Ser Leu Pro Gln Ser Thr Thr Pro Ser
1               5                   10                  15

Lys Gly Val Arg Leu Lys Ile Ala Ala Leu Leu Lys Thr Ile Gly Thr
            20                  25                  30

Leu Ile Leu Leu Leu Ile Ala Leu Pro Leu Asn Ala Leu Ile Val Leu
        35                  40                  45

Ile Ser Leu Met Cys Arg Pro Phe Thr Lys Lys Pro Ala Val Ala Thr
    50                  55                  60

His Pro Gln Asn Ile Leu Val Ser Gly Gly Lys Met Thr Lys Ala Leu
65                  70                  75                  80

Gln Leu Ala Arg Ser Phe His Ala Ala Gly His Arg Val Ile Leu Ile
                85                  90                  95

Glu Gly His Lys Tyr Trp Leu Ser Gly His Arg Phe Ser Asn Ser Val
            100                 105                 110

Ser Arg Phe Tyr Thr Val Pro Ala Pro Gln Asp Asp Pro Glu Gly Tyr
        115                 120                 125

Thr Gln Ala Leu Leu Glu Ile Val Lys Arg Glu Lys Ile Asp Val Tyr
    130                 135                 140

Val Pro Val Cys Ser Pro Val Ala Ser Tyr Tyr Asp Ser Leu Ala Lys
145                 150                 155                 160

Ser Ala Leu Ser Glu Tyr Cys Glu Val Phe His Phe Asp Ala Asp Ile
                165                 170                 175

Thr Lys Met Leu Asp Asp Lys Phe Ala Phe Thr Asp Arg Ala Arg Ser
            180                 185                 190

Leu Gly Leu Ser Ala Pro Lys Ser Phe Lys Ile Thr Asp Pro Glu Gln
        195                 200                 205

Val Ile Asn Phe Asp Phe Ser Lys Glu Thr Arg Lys Tyr Ile Leu Lys
    210                 215                 220

Ser Ile Ser Tyr Asp Ser Val Arg Arg Leu Asn Leu Thr Lys Leu Pro
225                 230                 235                 240

Cys Asp Thr Pro Glu Glu Thr Ala Ala Phe Val Lys Ser Leu Pro Ile
                245                 250                 255

Ser Pro Glu Lys Pro Trp Ile Met Gln Glu Phe Ile Pro Gly Lys Glu
            260                 265                 270

Leu Cys Thr His Ser Thr Val Arg Asp Gly Glu Leu Arg Leu His Cys
        275                 280                 285

Cys Ser Asn Ser Ser Ala Phe Gln Ile Asn Tyr Glu Asn Val Glu Asn
    290                 295                 300
```

Pro Gln Ile Gln Glu Trp Val Gln His Phe Val Lys Ser Leu Arg Leu
305                 310                 315                 320

Thr Gly Gln Ile Ser Leu Asp Phe Ile Gln Ala Glu Asp Gly Thr Ala
            325                 330                 335

Tyr Ala Ile Glu Cys Asn Pro Arg Thr His Ser Ala Ile Thr Met Phe
        340                 345                 350

Tyr Asn His Pro Gly Val Ala Glu Ala Tyr Leu Gly Lys Thr Pro Leu
    355                 360                 365

Ala Ala Pro Leu Glu Pro Leu Ala Asp Ser Lys Pro Thr Tyr Trp Ile
370                 375                 380

Tyr His Glu Ile Trp Arg Leu Thr Gly Ile Arg Ser Gly Gln Leu
385                 390                 395                 400

Gln Thr Trp Phe Gly Arg Leu Val Arg Gly Thr Asp Ala Ile Tyr Arg
                405                 410                 415

Leu Asp Asp Pro Ile Pro Phe Leu Thr Leu His His Trp Gln Ile Thr
            420                 425                 430

Leu Leu Leu Leu Gln Asn Leu Gln Arg Leu Lys Gly Trp Val Lys Ile
        435                 440                 445

Asp Phe Asn Ile Gly Lys Leu Val Glu Leu Gly Gly Asp
450                 455                 460

<210> SEQ ID NO 103
<211> LENGTH: 1047
<212> TYPE: DNA
<213> ORGANISM: Nostoc punctiforme ATCC29133

<400> SEQUENCE: 103
atgccagtac ttaatatcct tcatttagtt gggtctgcac acgataagtt ttactgtgat      60
ttatcacgtc tttatgccca agactgttta gctgcaacag cagatccatc gctttataac     120
tttcaaattg catatatcac acccgatcgg cagtggcgat ttcctgactc tctcagtcga     180
gaagatattg ctcttaccaa accgattcct gtgtttgatg ccatacaatt tctaacaggc     240
caaaacattg acatgatgtt accacaaatg ttttgtattc ctggaatgac tcagtaccgt     300
gccctattcg atctgctcaa gatcccttat ataggaaata ccccagatat tatggcgatc     360
gcggcccaca agccagagc caaagcaatt gtcgaagcag caggggtaaa agtgcctcgt      420
ggagaattgc ttcgccaagg agatattcca acaattacac ctccagcagt cgtcaaacct     480
gtaagttctg acaactcttt aggagtagtc ttagttaaag atgtgactga atatgatgct     540
gccttaaaga aagcatttga atatgcttcg gaggtcatcg tagaagcatt catcgaactt     600
ggtcgagaag tcagatgcgg catcattgta aaagacggtg agctaatagg tttacccctt     660
gaagagtatc tggtagaccc cacgataaaa cctatccgta actatgctga taaactccaa     720
caaactgacg atggcgactt gcatttgact gctaaagata tatcaaggc ttggatttta     780 gaccctaacg acccaatcac ccaaaaggtt cagcaagtgg ctaaaggtg tcatcaggct     840 ttgggttgtc gccactacag tttatttgac ttccgaatcg atccaaaggg acaaccttgg     900
ttcttagaag ctggattata ttgttctttt gccccaaaa gtgtgatttc ttctatggcg     960
aaagcagccg gaatccctct aaatgattta ttaataaccg ctattaatga acattgggt    1020 agtaataaaa aggtgttaca aaattga                                       1047

<210> SEQ ID NO 104
<211> LENGTH: 348
<212> TYPE: PRT
<213> ORGANISM: Nostoc punctiforme ATCC29133

<400> SEQUENCE: 104

```
Met Pro Val Leu Asn Ile Leu His Leu Val Gly Ser Ala His Asp Lys
1               5                   10                  15

Phe Tyr Cys Asp Leu Ser Arg Leu Tyr Ala Gln Asp Cys Leu Ala Ala
                20                  25                  30

Thr Ala Asp Pro Ser Leu Tyr Asn Phe Gln Ile Ala Tyr Ile Thr Pro
            35                  40                  45

Asp Arg Gln Trp Arg Phe Pro Asp Ser Leu Ser Arg Glu Asp Ile Ala
        50                  55                  60

Leu Thr Lys Pro Ile Pro Val Phe Asp Ala Ile Gln Phe Leu Thr Gly
65                  70                  75                  80

Gln Asn Ile Asp Met Met Leu Pro Gln Met Phe Cys Ile Pro Gly Met
                85                  90                  95

Thr Gln Tyr Arg Ala Leu Phe Asp Leu Leu Lys Ile Pro Tyr Ile Gly
            100                 105                 110

Asn Thr Pro Asp Ile Met Ala Ile Ala Ala His Lys Ala Arg Ala Lys
        115                 120                 125

Ala Ile Val Glu Ala Ala Gly Val Lys Val Pro Arg Gly Glu Leu Leu
130                 135                 140

Arg Gln Gly Asp Ile Pro Thr Ile Thr Pro Pro Ala Val Val Lys Pro
145                 150                 155                 160

Val Ser Ser Asp Asn Ser Leu Gly Val Val Leu Val Lys Asp Val Thr
                165                 170                 175

Glu Tyr Asp Ala Ala Leu Lys Lys Ala Phe Glu Tyr Ala Ser Glu Val
            180                 185                 190

Ile Val Glu Ala Phe Ile Glu Leu Gly Arg Glu Val Arg Cys Gly Ile
        195                 200                 205

Ile Val Lys Asp Gly Glu Leu Ile Gly Leu Pro Leu Glu Glu Tyr Leu
210                 215                 220

Val Asp Pro His Asp Lys Pro Ile Arg Asn Tyr Ala Asp Lys Leu Gln
225                 230                 235                 240

Gln Thr Asp Asp Gly Asp Leu His Leu Thr Ala Lys Asp Asn Ile Lys
                245                 250                 255

Ala Trp Ile Leu Asp Pro Asn Asp Pro Ile Thr Gln Lys Val Gln Gln
            260                 265                 270

Val Ala Lys Arg Cys His Gln Ala Leu Gly Cys Arg His Tyr Ser Leu
        275                 280                 285

Phe Asp Phe Arg Ile Asp Pro Lys Gly Gln Pro Trp Phe Leu Glu Ala
290                 295                 300

Gly Leu Tyr Cys Ser Phe Ala Pro Lys Ser Val Ile Ser Ser Met Ala
305                 310                 315                 320

Lys Ala Ala Gly Ile Pro Leu Asn Asp Leu Leu Ile Thr Ala Ile Asn
                325                 330                 335

Glu Thr Leu Gly Ser Asn Lys Lys Val Leu Gln Asn
            340                 345
```

MICROORGANISM FOR PRODUCING A MYCOSPORINE-LIKE AMINO ACID AND METHOD FOR PRODUCING A MYCOSPORINE-LIKE AMINO ACID USING THE SAME

CROSS-REFERENCE TO RELATED APPLICATIONS

This application is the National Stage of International Application No. PCT/KR2018/009246, filed on Aug. 13, 2018 claiming the priority of KR 10-2017-0103795, filed on Aug. 16, 2017, the content of each of which is incorporated by reference herein.

TECHNICAL FIELD OF THE INVENTION

The present disclosure relates to a microorganism for producing a mycosporine-like amino acid, and to a method for producing a mycosporine-like amino acid using the microorganism.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Feb. 13, 2020, is named HANO1022US_SeqList.txt and is 178, kilobytes in size.

DEPOSIT OF BIOLOGICAL MATERIAL

The following biological materials have been deposited under the terms of the Budapest Treaty with the Korean Culture Center of Microoganisms, Yurim B/D, 45, Hongje-nae-2ga-gil, Seodaemun-gu, Seoul 120-861 Republic of Korea, and given the following number:
Deposit Accession Number Date of Deposit
*Escherichia coli* CB06-0017 KCCM12044P Jun. 26, 2017
*Escherichia coli* CB06-0018 KCCM12045P Jun. 26, 2017
*Escherichia coli* CB06-0019 KCCM12046P Jun. 26, 2017

The microorganisms have been deposited under conditions that assure that access to the microorganisms will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny are filed. However, it should be understood that the availability of a deposit does not constitute a license to practice the subject invention in derogation of patent rights granted by government action.

BACKGROUND OF THE INVENTION

Ultraviolet radiation emitted from the sun consists of UV-A (Ultraviolet A, which ranges from approximately 320 nm to 400 nm), UV-B (Ultraviolet B, which ranges from approximately 290 nm to 320 nm), and UV-C (Ultraviolet C, which ranges from approximately 100 nm to 280 nm). Among the sun's rays, approximately 6% of the UV-A and UV-B reach the surface of the earth, on the other hand, UV-C does not reach the surface of the earth as it is absorbed and scattered in the earth's ozone layer and the atmosphere.

Although these UV rays may provide beneficial aspects, such as vitamin D synthesis in the body, treatment of skin diseases, sterilization effects, etc., they also impose harmful aspects such as sunburn, skin cancer, aging, photosensitive skin diseases, and mutagenesis. It has been known that UV-A penetrates even to the dermis layer, mainly causing pigmentation and skin aging, and is involved in the development of photosensitive skin diseases, while UV-B is implicated in causing sunburn, pigmentation and skin cancer by penetrating the upper part of the epidermis and dermis layers with high energy rays.

Attempts have been made to block the sunlight in order to prevent these side effects caused by the sun's rays. To this end, types of sunscreen agents can be classified into chemical sunscreen agents and physical sunscreen agents. Chemical sunscreen agents primarily block the penetration of sunlight through absorption, while physical sunscreen agents block the sunlight through reflection and scattering of the sunlight.

Chemical sunscreen agents contain one or more UV-absorbing components, such as PABA, PABA esters (amyl dimethyl PABA, octyl dimethyl PABA), cinnamates (cinoxate), salicylates (Homomenthyl salicylate), camphor, etc. which mainly absorb UV-B, and benzophenone (oxybenzone, dioxybenzone, sulisobenzone), dibenzoyl methane, anthranilate, etc., which mainly absorb UV-A. Although these chemical sunscreen agents may provide a UV-protecting effect by absorbing UV rays, some of which may cause irritation in the skin or the eyes. Particularly, PABA, PABA esters, benzophenones, cinnamates, etc., are known to cause contact dermatitis. Additionally, problems have been reported that some others are associated with developing hypersensitivity reactions in the skin, and thus, the use of chemical sunscreen agents and the amount of their use are restricted in some countries.

Physical sunscreen agents, which contain components that exist in nature, protect the skin by reflecting and scattering UV rays that penetrate the skin. For example, physical sunscreen agents such as titanium dioxide, talc (magnesium silicate), magnesium oxide, zinc oxide, kaolin, etc. can provide a UV-protecting effect for both UV-A and UV-B. Further, they have advantages in that they do not have side effects, such as contact dermatitis, and are not easily washed off by water. In contrast, they also have disadvantages in that it may be difficult to maintain an effective amount of physical sunscreen agents while implementing a desired formulation thereof, and they leave a white cast when applied to the skin.

Mycosporine-like amino acids (MAAs) are substances that are found in natural organisms and are known to effectively absorb UVA (320 nm to 400 nm) and UVB (290 mm to 320 mm). There are 35 species or more of MAAs in nature according to the type of amino acids, cyclohexenone or cyclohexenimine ring, which serve as precursors. (*Mar. Biol.*, 1991, 108: 157-166; *Planta Med.*, 2015, 81: 813-820). Recently, various glycosylated MAAs are found in microalgae, which have been reported to play a role as excellent antioxidants (*Journal of Photochemistry and Photobiology*, 2015, 142: 154-168). Additionally, MAAs are known to not only provide UV protection but also show resistance to oxidation, osmosis, and thermal stress (*Comp. Biochem. Physiol. C Toxicol. Pharmacol.*, 2007, 146: 60-78; *J. Photochem. Photobiol. B.*, 2007, 89: 29-35).

However, the amount of MAAs produced in microalgae is very small at a few µg level, and the conditions for separating, extracting and purifying MAAs by culturing microalgae are complicated, and thus, it would be difficult to produce MAAs in a large-scale production.

PRIOR ART LITERATURE

Non-Patent Literature (Non-Patent Literature 1) Comp. Biochem. Physiol. B 1995, 112: 105-114.
(Non-Patent Literature 2) FEMS Microbiol Lett. 2007, 269: 1-10.
(Non-Patent Literature 3) Ann. Rev. Physiol. 2002, 64: 223-262.
(Non-Patent Literature 4) Mar. Biol. 1991, 108: 157-166.
(Non-Patent Literature 5) Journal of Photochemistry and Photobiology B: Biology. 2015, 142: 154-168
(Non-Patent Literature 6) Biol. Rev. 1999, 74: 311-345.
(Non-Patent Literature 7) Mol. Biol. Evol. 2006, 23: 1437-1443.
(Non-Patent Literature 8) Science, 2010, 329: 1653-1656.
(Non-Patent Literature 9) Genomics 2010, 95: 120-128.
(Non-Patent Literature 10) Geomicrobiol. J. 1997. 14: 231-241.
(Non-Patent Literature 11) Comp. Biochem. Physiol. C Toxicol. Pharmacol. 2007. 146: 60-78.
(Non-Patent Literature 12) Can. J. Bot. 2003. 81: 131-138.
(Non-Patent Literature 13) J. Photochem. Photobiol. B. 2007, 89: 29-35.
(Non-Patent Literature 14) J. Bacteriol. 2011. 193(21): 5923-5928.
(Non-Patent Literature 15) Planta Med. 2015. 81: 813-820
(Non-Patent Literature 16) ACS Appl. Mater. Interfaces. 2015. 7: 16558-16564
(Non-Patent Literature 17) Appl Environ Microbiol. 2016, 82(20): 6167-6173
(Non-Patent Literature 18) ChemBioChem. 2015, 16: 320-327
(Non-Patent Literature 19) Methods Mol Biol. 2013, 1073: 43-7
(Non-Patent Literature 20) Enzyme Microb Technol., 2016, January, 82: 96-104
(Non-Patent Literature 21) Nature Review, 2011, 9: 791-802

SUMMARY OF THE INVENTION

Technical Problem

The present inventors have made extensive efforts to increase the production of MAAs in microorganisms. As a result, it was confirmed that the production of MAAs was increased through various studies on the inactivation of 3-dehydroquinate dehydratase activity in the microorganism for producing MAAs, thereby completing the present disclosure.

Technical Solution

It is one object of the present disclosure to provide a microorganism for producing a mycosporine-like amino acid, wherein an activity of 3-dehydroquinate dehydratase is inactivated as compared to a non-modified microorganism.

It is another object of the present disclosure to provide a method for producing a mycosporine-like amino acid, including:
culturing the microorganism; and
recovering a mycosporine-like amino acid from the cultured microorganism or medium.

Advantageous Effects

The microorganism of the present disclosure shows an improved ability for producing a mycosporine-like amino acid, and thus can be effectively used in the production of a mycosporine-like amino acid.

DETAILED DESCRIPTION OF PREFERRED EMBODIMENTS

The specific details of the present disclosure may be explained as follows.

Meanwhile, the explanations and embodiments disclosed in the present disclosure may be applied to other explanations and embodiments, respectively. That is, all combinations of various elements disclosed herein belong to the scope of the present disclosure. Additionally, the scope of the present disclosure should not be limited by the specific descriptions described hereinbelow. Additionally, those of ordinary skill in the art may be able to recognize or confirm, using only conventional experimentation, many equivalents to the particular aspects of the invention described in this application. Furthermore, it is also intended that these equivalents be included in the present disclosure.

In order to achieve the objects above, an aspect of the present disclosure provides a microorganism for producing a mycosporine-like amino acid, wherein the activity of 3-dehydroquinate dehydratase is inactivated as compared to a non-modified microorganism.

As used herein, the term "3-dehydroquinate dehydratase" refers to an enzyme that catalyzes the reversible reaction represented by Reaction Scheme below, and may specifically convert 3-dehydroquinate into 3-dehydroshikimate, but is not limited thereto.

Reaction Scheme

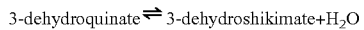

As used herein, the term "inactivation" refers to a case where the activity of an enzymatic protein originally possessed by a microorganism is weakened compared to the endogenous activity thereof or the activity before modification; a case where the protein is not in any way expressed; or a case where the protein is expressed but exhibits no activity. The inactivation is a concept that includes a case where the activity of an enzyme itself is weakened or eliminated compared to the activity of the enzyme originally possessed by a microorganism, due to a modification in the polynucleotide encoding the enzyme, etc.; a case where the level of overall enzyme activity within a cell is reduced or eliminated compared to the wild-type microorganism, due to inhibition of expression of the gene encoding the enzyme, or inhibition of translation, etc.; a case where a part or the entirety of the gene encoding the enzyme is deleted; and a combination thereof, but is not limited thereto. The term "non-modified microorganism" refers to a microorganism having the activity of a specific protein originally possessed by the parental strain prior to modification thereof, when the traits of the microorganism are modificated through genetic modification in the specific protein possessed by a microorganism for comparison due to natural or artificial factors. As used herein, the "non-modified microorganism" can be interchangeably used with "a microorganism having an endogenous activity".

The inactivation of the enzymatic activity may be achieved by various methods well known in the art. Examples of the methods include 1) a method of deleting a part or the entirety of a gene encoding the enzyme on a chromosome; 2) a method of modifying an expression regulatory sequence such that the expression of the gene encoding the protein on the chromosome is reduced; 3) a method of modifying a gene sequence encoding the protein on the chromosome such that the activity of the protein is removed or weakened; 4) a method of introducing an antisense oligonucleotide that binds complementarily to the transcript of the gene encoding the protein on the chromosome (e.g., antisense RNA); 5) a method of artificially adding a sequence complementary to the Shine-Dalgarno sequence of the gene encoding the protein on the chromosome to the upstream of the Shine-Dalgarno sequence to form a secondary structure, thereby making the adhesion of ribosome impossible; and 6) a method of reverse transcription engineering (RTE), which adds a promoter, which is to be reverse-transcribed, to the 3' end of the open reading frame (ORF) of the polynucleotide sequence encoding the protein, or a combination thereof, but are not limited particularly thereto.

The method of deleting a part or the entirety of a gene encoding the protein on the chromosome may be performed by replacing the polynucleotide encoding the endogenous target protein within the chromosome with a polynucleotide having a partially deleted nucleic acid sequence, or a marker gene through a vector for chromosomal insertion into a microorganism. As an example of the method of deleting a part or the entirety of the polynucleotide, a method of deleting a polynucleotide by homologous recombination may be used, but is not limited thereto.

The method of modifying an expression regulatory sequence may be performed by inducing a modification in the expression regulatory sequence through deletion, insertion, conservative or non-conservative substitution, or a combination thereof so as to further weaken the activity of the expression regulatory sequence; or by replacing the sequence with a nucleic acid sequence having a weaker activity. The expression regulatory sequence may include a promoter, an operator sequence, a sequence encoding a ribosome-binding domain, and a sequence for regulating the termination of transcription and translation, but is not limited thereto.

The method of modifying the gene sequence on the chromosome may be performed by inducing a modification in the gene sequence through deletion, insertion, conservative or non-conservative substitution, or a combination thereof so as to further weaken the activity of the enzyme; or by replacing the sequence with a gene sequence modified to have a weaker activity or a gene sequence modified to have no activity at all, but is not limited thereto.

The polynucleotide may be described as a gene in cases where it refers to an assemblage of polynucleotides capable of carrying out functions. In the present disclosure, polynucleotides and genes may be used interchangeably, and polynucleotide sequences and nucleotide sequences may be used interchangeably.

As used herein, the term "part", although it may vary depending on the kinds of polynucleotide, may specifically refer to 1 to 300 nucleotides, more specifically 1 to 100 nucleotides, and even more specifically 1 to 50 nucleotides, but is not particularly limited thereto.

In the microorganism of the present disclosure, an activity of at least one selected from the group consisting of 2-dehydro-3-deoxyphosphoheptonate aldolase, phosphoenolpyruvate synthetase, transketolase I/II, and 3-dehydroquinate synthase, specifically the activity of one or more, two or more, three or more, or all enzymes may be enhanced as compared to a non-modified microorganism.

The 2-dehydro-3-deoxyphosphoheptonate aldolase refers to an enzyme that catalyzes the reversible reaction represented by Reaction Scheme below, and may specifically synthesize 3-deoxy-arabino-heptulosonate 7-phosphate, but is not limited thereto.

Reaction Scheme

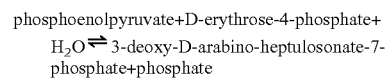

phosphoenolpyruvate+D-erythrose-4-phosphate+ H$_2$O ⇌ 3-deoxy-D-arabino-heptulosonate-7-phosphate+phosphate The phosphoenolpyruvate synthetase refers to an enzyme that catalyzes the reversible reaction represented by Reaction Scheme below, and may specifically synthesize phosphoenolpyruvate, but is not limited thereto.

Reaction Scheme

ATP+pyruvate+H$_2$O ⇌ AMP+phosphoenolpyruvate+phosphate

The transketolase I/II refers to an enzyme that catalyzes the reversible reaction represented by Reaction Scheme below.

Reaction Scheme

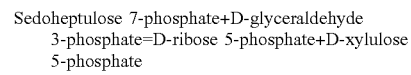

Sedoheptulose 7-phosphate+D-glyceraldehyde 3-phosphate=D-ribose 5-phosphate+D-xylulose 5-phosphate The 3-dehydroquinate synthase refers to an enzyme that catalyzes the reversible reaction represented by Reaction Scheme below, and may specifically synthesize 3-dehydroquinate (3-DHQ), but is not limited thereto.

[Reaction Scheme]

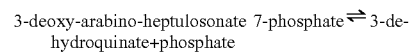

3-deoxy-arabino-heptulosonate 7-phosphate ⇌ 3-dehydroquinate+phosphate

As used herein, the term "enhancement of activity" means that the activity of an enzymatic protein is introduced, or the activity is enhanced as compared to the endogenous activity possessed by a microorganism or the activity before modification. The "introduction" of the activity means that the activity of a specific polypeptide that the microorganism did not originally have is naturally or artificially expressed. For example, the enhancement of the activity may include both an enhancement by introducing 2-dehydro-3-deoxyphosphoheptonate aldolase, phosphoenolpyruvate synthetase, transketolase I/II, and/or 3-dehydroquinate synthase; or an enhancement of the endogenous activity of 2-dehydro-3-deoxyphosphoheptonate aldolase, phosphoenolpyruvate synthetase, transketolase I/II, and/or 3-dehydroquinate synthase. Specifically, the enhancement of the activity in the present disclosure may be performed by the following methods:

1) a method of increasing the copy number of the polynucleotide encoding the enzymes;
2) a method of modifying an expression regulatory sequence such that the expression of the polynucleotide is increased;
3) a method of modifying the polynucleotide sequence on the chromosome such that the activity of the enzymes is enhanced; and
4) a method of modification to enhance the activity by a combination of the above methods, but is not limited thereto.

The increasing of the copy number of the polynucleotide in method 1) above may be performed in a form in which the polynucleotide is operably linked to a vector, or by inserting into a chromosome of a host cell, but is not particularly limited thereto. Additionally, in an aspect to increase the copy number, it may be performed by introducing into a host cell a foreign polynucleotide that exhibits the activity of the enzyme, or a modified polynucleotide in which the codons of the foreign polynucleotide have been optimized. The foreign polynucleotide may be used without limitation to its origin or sequence as long as it exhibits an activity identical or similar to that of the enzyme. The introduction may be performed by those skilled in the art by selecting a suitable transformation method known in the art, and an enzyme may be produced as the introduced polynucleotides are expressed in the host cell, thereby increasing its activity.

Next, the modification of an expression regulatory sequence such that the expression of the polynucleotide is increased in method 2) may be performed by inducing a modification in the sequence through deletion, insertion, or non-conservative or conservative substitution of a nucleic acid sequence, or a combination thereof so as to further enhance the activity of the expression regulatory sequence, or by replacing with a nucleic acid sequence having a stronger activity, but is not particularly limited thereto. Additionally, the expression regulatory sequence may include a promoter, an operator sequence, a sequence encoding a ribosome-binding domain, a sequence regulating the termination of transcription and translation, etc., but is not particularly limited thereto.

Specifically, a strong heterologous promoter may be linked to the upstream region of the expression unit of the polynucleotide instead of the original promoter. Examples of the strong promoter include CJ7 promoter, lysCP1 promoter, EF-Tu promoter, groEL promoter, aceA or aceB promoter, etc. More specifically, the expression rate of the polynucleotide encoding the enzyme may be enhanced by operably linking the polynucleotide with the lysCP1 promoter (WO2009/096689) or CJ7 promoter (WO2006/065095), but is not limited thereto.

Further, the modification of the polynucleotide sequence on the chromosome in method 3) may be performed by inducing a modification in the expression regulatory sequence through deletion, insertion, or non-conservative or conservative substitution of a nucleic acid sequence, or a combination thereof so as to further enhance the activity of the polynucleotide sequence, or by replacing the polynucleotide sequence with a polynucleotide sequence modified to have a stronger activity, but is not particularly limited thereto.

Finally, the method of modification to enhance the activity by a combination of methods 1) to 3) in method 4) may be performed by a combined application of at least one of the following methods: increasing of the copy number of the polynucleotide encoding the protein; modification of an expression regulatory sequence such that the expression of the polynucleotide is increased; modification of the polynucleotide sequence on the chromosome, and modification of a foreign polynucleotide exhibiting the activity of the enzyme or a codon-optimized modified polynucleotide thereof.

As used herein, the term "vector" refers to a DNA construct containing the nucleotide sequence of a polynucleotide encoding the target protein, which is operably linked to a suitable regulatory sequence such that the target protein can be expressed in an appropriate host. The regulatory sequence includes a promoter capable of initiating transcription, any operator sequence for controlling the transcription, a sequence encoding an appropriate mRNA ribosome-binding domain, and a sequence regulating the termination of transcription and translation. After being transformed into a suitable host cell, the vector may be replicated or function irrespective of the host genome, and may be integrated into the host genome itself.

The vector used in the present disclosure is not particularly limited as long as it can be replicated in a host cell, and any vector known in the art may be used. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc. may be used. Specifically, the vectors pDZ, pACYC177, pACYC184, pCL, pECCG117, pUC19, pBR322, pMW118, pCC1BAC, etc. may be used, but the vector is not limited thereto.

The vector that can be used in the present disclosure is not particularly limited, and a known expression vector may be used. Additionally, a polynucleotide encoding a target protein may be inserted into the chromosome through a vector for chromosomal insertion. The insertion of the polynucleotide into the chromosome may be performed using any method known in the art, for example, by homologous recombination, but is not limited thereto. A selection marker for confirming the insertion into the chromosome may be further included. The selection marker is used for selecting a cell transformed into a vector, i.e., in order to confirm whether the target nucleic acid molecules have been inserted, and markers that provide selectable phenotypes, such as drug resistance, nutrient requirement, resistance to cytotoxic agents, or expression of surface proteins, may be used. Only the cells expressing the selection markers can survive or express other phenotypic traits under the environment treated with selective agents, and thus, the transformed cells can be easily selected.

As used herein, the term "transformation" refers to a process of introducing a vector including a polynucleotide encoding a target polypeptide into a host cell, thereby enabling the expression of the protein encoded by the polynucleotide in the host cell. As long as the transformed polynucleotide can be expressed in the host cell, it does not matter whether it is inserted into the chromosome of a host cell and located therein, or located outside the chromosome, and both cases may be included. Additionally, the polynucleotide includes DNA and RNA which encode the target polypeptide. The polynucleotide may be introduced in any form as long as it can be introduced into a host cell and expressed therein. For example, the polynucleotide may be introduced into a host cell in the form of an expression cassette, which is a gene construct including all elements necessary for self-expression. The expression cassette may conventionally include a promoter operably linked to the polynucleotide, a terminator, a ribosome-binding domain, and a stop codon. The expression cassette may be in the form of an expression vector capable of self-replication. Additionally, the polynucleotide may be introduced into a host cell as it is and operably linked to a sequence necessary for its expression in the host cell, but is not limited thereto. The method for transforming the vector includes any method of introducing a nucleic acid into a cell, and may be performed by selecting a suitable standard technique known in the art according to the host cell. For example, the transformation may be carried out via electroporation, calcium phosphate ($CaPO_4$) precipitation, calcium chloride ($CaCl_2$) precipitation, microinjection, a polyethylene glycol (PEG) technique, a DEAE-dextran technique, a cationic liposome technique, a lithium acetate-DMSO technique, etc., but the method is not limited thereto.

Further, as used above, the term "operably linked" refers to a functional linkage between the above polynucleotide sequence and a promoter sequence which initiates and mediates the transcription of the polynucleotide encoding the target protein of the present disclosure. The operable linkage may be prepared using a genetic recombinant technique known in the art, and site-specific DNA cleavage and ligation may be performed using enzymes such as lyses, ligases, etc. known in the art, but is not limited thereto.

The genetic information of 3-dehydroquinate dehydratase, 2-dehydro-3-deoxyphosphoheptonate aldolase, phosphoenolpyruvate synthetase, transketolase, and 3-dehydroquinate synthase can be obtained from a known database, and examples thereof include GenBank of National Center for Biotechnology Information (NCBI), etc., but the known database is not limited thereto.

The 3-dehydroquinate dehydratase, 2-dehydro-3-deoxyphosphoheptonate aldolase, phosphoenolpyruvate synthetase, transketolase, and 3-dehydroquinate synthase may not be limited by their origins or sequences, since there may be a difference in the amino acid sequence of the protein that exhibits the activity depending on the microbial species or microorganisms.

Specifically, the 3-dehydroquinate dehydratase may be a protein including an amino acid sequence of SEQ ID NO: 72 or 80, and 2-dehydro-3-deoxyphosphoheptonate aldolase, phosphoenolpyruvate synthetase, transketolase, and 3-dehydroquinate synthase may be a protein including an amino acid sequence of SEQ ID NOS: 74, 76, 78, and 84, respectively, but are not limited thereto. In the present disclosure, "the protein including an amino acid sequence" may be used interchangeably with the expression "the protein having an amino acid sequence" or "the protein consisting of an amino acid sequence".

Additionally, in the present disclosure, the enzymes may not only include the protein having an amino acid sequence of SEQ ID NO: described above, but also a protein having a homology of 80% or more, specifically 90% or more, more specifically 95% or more, even more specifically 99% or more to the above amino acid sequences, as long as the protein has a biological activity identical or corresponding to that of each enzyme.

Further, it is apparent that, as an amino acid sequence having a homology to the above sequences, an amino acid sequence with deletion, modification, substitution, or addition of a part of the sequence also falls within the scope of the present disclosure as long as the amino acid sequence has a biological activity substantially identical or corresponding to that of the enzymatic protein having an amino acid sequence of SEQ ID NO: described above.

The polynucleotide encoding 3-dehydroquinate dehydratase, 2-dehydro-3-deoxyphosphoheptonate aldolase, phosphoenolpyruvate synthetase, transketolase, and 3-dehydroquinate synthase of the present disclosure may include a polynucleotide having an amino acid sequence of SEQ ID NO: described above, or a polynucleotide encoding a protein having a homology of 80% or more, specifically 90% or more, more specifically 95% or more, even more specifically 99% or more to the amino acid sequences, as long as it has a biological activity identical or corresponding to that of each enzyme.

Additionally, as for the polynucleotide encoding 2-dehydro-3-deoxyphosphoheptonate aldolase, phosphoenolpyruvate synthetase, transketolase, and 3-dehydroquinate synthase, considering the codons preferred by organisms to express the protein due to codon degeneracy, various modifications may be executed on the coding region within the scope without changing the amino acid sequence of the polypeptide. Accordingly, the polynucleotide may include any polynucleotide sequence encoding each enzymatic protein without limitation.

Further, a probe which can be prepared from a known gene sequence, for example, any sequence which hybridizes with a sequence complementary to all or a part of the nucleotide sequence under stringent conditions to encode a protein having the activity of 3-dehydroquinate dehydratase, 2-dehydro-3-deoxyphosphoheptonate aldolase, phosphoenolpyruvate synthetase, transketolase, and 3-dehydroquinate synthase may be included without limitation.

As used herein, the term "homology" refers to the degree of correspondence to a given amino acid sequence or nucleotide sequence, and may be expressed as a percentage. In the present specification, a homologous sequence having an activity which is identical or similar to that of the given amino acid sequence or nucleotide sequence may be indicated in terms of "% homology". For example, the homology may be confirmed using a standard software for calculating parameters such as score, identity, and similarity, specifically, BLAST 2.0, or by comparing sequences via hybridization experiments under defined stringent conditions, and the defined appropriate hybridization conditions are within the skill of the art, and may be determined by a method well known to those skilled in the art (For example, J. Sambrook et al., *Molecular Cloning, A Laboratory Manual*, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York). The term "stringent conditions" refer to the conditions which allow the specific hybridization between the polynucleotides. Such conditions are specifically disclosed in the literature (e.g., J. Sambrook et al.).

As used herein, the term "mycosporine-like amino acids (MAAs)" refer to cyclic compounds that absorb ultraviolet rays. In the present disclosure, any mycosporine-like amino acid may be included without limitation as long as it can absorb UV rays, but it may specifically be a compound containing a central cyclohexenone or cyclohexenimine ring; or a compound in which various substances, such as amino acid, etc., are bound to the central ring. More specifically, it may be mycosporine-2-glycine, palythinol, palythenic acid, deoxygadusol, mycosporine-methylamine-threonine, mycosporine-glycine-valine, palythine, asterina-330, shinorine, porphyra-334, euhalothece-362, mycosporine-glycine, mycosporine-ornithine, mycosporine-lysine, mycosporine-glutamic acid-glycine, mycosporine-methylamine-serine, mycosporine-taurine, palythene, palythine-serine, palythine-serine-sulfate, palythinol, usujirene, or a combination thereof.

In the present disclosure, the mycosporine-like amino acids may be interchangeably used with MAA and MAAs.

As used herein, the term "microorganism for producing a mycosporine-like amino acid" refers to a microorganism including a gene of an enzyme involved in the biosynthesis of mycosporine-like amino acids, or a cluster of the genes. Additionally, as used herein, the term "mycosporine-like amino acid biosynthetic gene" refers to a gene encoding an enzyme involved in the biosynthesis of mycosporine-like amino acids, and also includes a cluster of the genes. The mycosporine-like amino acid biosynthetic gene includes both foreign and/or endogenous genes of a microorganism as long as the microorganism including the gene can produce mycosporine-like amino acids. The foreign genes may be homologous and/or heterologous.

The mycosporine-like amino acid biosynthetic gene may not be limited by the species of the microorganism derived from the genes, as long as the microorganism including the same produces an enzyme involved in the biosynthesis of mycosporine-like amino acids and consequently produces mycosporine-like amino acids. Specifically, it may be *Anabaena variabilis, Nostoc punctiforme, Nodularia spumigena, Cyanothece* sp. PCC 7424, *Lyngbya* sp. PCC 8106, *Microcystis aeruginosa, Microcoleus chthonoplastes, Cyanothece* sp. ATCC 51142, *Crocosphaera watsonii, Cyanothece* sp. CCY 0110, *Cylindrospermum stagnale* sp, PCC 7417, *Aphanothece halophytica* or *Trichodesmium erythraeum*, which are species of cyanobacteria, or *Magnaporthe oryzae, Pyrenophora tritici-repentis, Aspergillus clavatus, Nectria haematococca, Aspergillus nidulans, Gibberella zeae, Verticillium albo-atrum, Botryotinia fuckeliana*, or *Phaeosphaeria nodorum*, which are species of fungi, or *Nematostella vectensis, Heterocapsa triquetra, Oxyrrhis marina, Karlodinium micrum, Actinosynnema mirum*, etc., but is not limited thereto.

According to one embodiment, the microorganism for producing a mycosporine-like amino acid of the present disclosure may include a mycosporine-like amino acid biosynthetic gene.

Specifically, the mycosporine-like amino acid biosynthetic gene may not be limited by the name of the enzymes or the derived microorganisms as long as the microorganism can produce mycosporine-like amino acids, and may specifically include at least one, specifically one or more, two or more, or three or more, or all enzymatic proteins selected from the group consisting of 2-demethyl 4-deoxygadusol synthase, O-methyltransferase, and C—N ligase; or a gene encoding an enzymatic protein having an activity identical and/or similar thereto.

For example, the 2-demethyl 4-deoxygadusol synthase is an enzyme that converts sedoheptulose-7-phosphate into 2-demethyl-4-deoxygadusol. The O-methyltransferase is an enzyme that converts 2-demethyl-4-deoxygadusol into 4-deoxygadusol, and glycylation of the 4-deoxygadusol is catalyzed by the C—N ligase.

Additionally, the microorganism for producing a mycosporine-like amino acid may include a gene of an enzyme having an activity of attaching additional amino acid residues to mycosporine-like amino acids, or a cluster of the genes. The gene or the cluster of the genes may not be limited by the name of the enzymes or the derived microorganisms as long as the microorganism for producing a mycosporine-like amino acid can produce mycosporine-like amino acids, to which two or more amino acid residues are attached, and may specifically include at least one, specifically one or more, two or more, three or more, or all enzymatic proteins selected from the group consisting of non-ribosomal peptide synthetase (NRPS), non-ribosomal peptide synthetase-like enzyme (NRPS-like enzyme), and D-Ala D-Ala ligase (DDL); or a gene encoding an enzymatic protein having an activity identical and/or similar thereto. Some mycosporine-like amino acids may include a second amino acid residue in mycosporine-glycine. The at least one enzyme selected from the group consisting of non-ribosomal peptide synthetase, non-ribosomal peptide synthetase-like enzyme, and D-Ala D-Ala ligase may attach a second amino acid residue to mycosporine-glycine.

According to one embodiment, the microorganism for producing a mycosporine-like amino acid may include any enzyme without limitation to the name of the enzymes or species of the derived microorganisms as long as it has an activity of attaching a second amino acid to mycosporine-glycine, as the non-ribosomal peptide synthetase, non-ribosomal peptide synthetase-like enzyme, and D-Ala D-Ala ligase.

In an embodiment, the non-ribosomal peptide synthetase-like enzyme (Ava_3855) found in *Anabaena variabilis* or D-Ala D-Ala ligase (NpF5597) found in *Nostoc punctiforme* can produce shinorine by attachment of serine residue to mycosporine-glycine. In another embodiment, mycosporine-2-glycine may be formed by attachment of a second glycine residue via a D-Ala D-Ala ligase homolog (Ap_3855) found in *Aphanothece halophytica*. Similarly, in *Actinosynnema mirum*, serine or alanine may be attached by a D-Ala D-Ala ligase to form shinorine or mycosporine-glycine-alanine. The microorganism according to one embodiment of the present disclosure may include an enzyme suitable for the production of desired mycosporine-like amino acids by selecting from the above-described enzymes or enzymes having an activity identical and/or similar thereto.

The 2-demethyl 4-deoxygadusol synthase, O-methyltransferase, C—N ligase, non-ribosomal peptide synthetase, non-ribosomal peptide synthetase-like enzyme, and/or D-Ala D-Ala ligase that can be used in the present disclosure may not be limited by the species of the derived microorganisms, and any enzyme may be included without limitation as long as it is known to serve identical and/or similar functions and activities. Additionally, the numerical range of homology between these enzymes may not be limited. For example, MylA, MylB, MylD, MylE and MylC of *Cylindrospermum stagnate* PCC 7417 are homologous to 2-demethyl 4-deoxygadusol synthase, O-methyltransferase, C—N ligase, and D-Ala D-Ala ligase derived from *Anabaena variabilis* and *Nostoc punctiforme*, and the similarity between these homologs is about 61 to 88% (*Appl Environ Microbiol*, 2016, 82(20), 6167-6173; *J Bacteriol*, 2011, 193(21), 5923-5928). That is, the enzyme that can be used in the present disclosure may not be particularly limited by the species of the derived microorganisms or sequence homology as long as it is known to exhibit identical and/or similar functions and effects. Further, the non-patent literatures disclosed in the prior art are incorporated herein by reference in their entirety.

Additionally, the mycosporine-like amino acid biosynthetic gene may be a polynucleotide encoding a protein including the amino acid sequence of SEQ ID NO: 2, 4, 86, 88, 90, 92, 94, 96, 98, 100, 102, or 104, but is not limited thereto.

Additionally, the mycosporine-like amino acid biosynthetic gene may include a nucleotide sequence encoding a protein including the amino acid sequence having a homology of 50%, 60%, or 70% or more, specifically, 80% or more, more specifically 90% or more, even more specifically 95%, and even more specifically 99% to the amino acid sequence of SEQ ID NO: 2, 4, 86, 88, 90, 92, 94, 96, 98, 100, 102, or 104, and any nucleotide sequence encoding a protein having a homology deviating from the above may be included without limitation as long as the microorganism produce mycosporine-like amino acids. Specifically, the mycosporine-like amino acid biosynthetic gene may include, but is not limited to, the nucleotide sequence of SEQ ID NO: 1, 3, 85, 84, 89, 91, 93, 95, 97, 99, 101, or 103.

Additionally, it is apparent that, as an amino acid sequence having a homology to the above amino acid sequence, an amino acid sequence with deletion, modification, substitution, or addition of a part of the sequence also falls within the scope of the present disclosure as long as the amino acid sequence has a biological activity substantially identical or corresponding to that of the protein having the amino acid sequence of SEQ ID NO: described above.

Additionally, considering the codons preferred by organisms to express the protein due to codon degeneracy, various modifications may be executed on the coding region within the scope without changing the amino acid sequence of the polypeptide. Accordingly, the mycosporine-like amino acid biosynthetic gene may include without limitation any nucleotide sequence encoding a protein involved in the synthesis of mycosporine-like amino acids.

Additionally, a probe which can be prepared from a known gene sequence, for example, any sequence which hybridizes with a sequence complementary to all or a part of the nucleotide sequence under stringent conditions to encode a protein involved in the biosynthesis of mycosporine-like amino acids may be included without limitation.

According to an embodiment, the microorganism for producing a mycosporine-like amino acid may include mycosporine-like amino acid biosynthetic genes derived from different origins.

In the present disclosure, the inactivation of a protein, enhancement of the activity of a protein, and/or introduction of a gene herein may be performed simultaneously, sequentially, or in a reverse order.

As used herein, the term "microorganism for producing a mycosporine-like amino acid" possess endogenous and/or exogenously introduced mycosporine-like amino acid biosynthetic genes, and thus can produce mycosporine-like amino acids, and additionally, it may be a microorganism in which the ability to produce mycosporine-like amino acids is increased by inactivating the endogenous 3-dehydroquinate dehydratase activity. Introduction of the mycosporine-like amino acid biosynthetic gene and inactivation of 3-dehydroquinate dehydratase may be performed simultaneously, sequentially, or in a reverse order.

Additionally, the microorganism of the present disclosure may be a natural microorganism originally having a mycosporine-like amino acid biosynthetic gene; and a microorganism into which a heterologous and/or homologous mycosporins-like amino acid biosynthetic gene has been introduced, but is not limited thereto.

Additionally, the microorganism of the present disclosure may be a microorganism having an enhanced activity of an enzyme encoded by an endogenous and/or introduced mycosporine-like amino acid biosynthesis related gene, but is not limited thereto.

Additionally, the microorganism of the present disclosure may have no limitation as long as it has the activity of 3-dehydroquinate dehydratase before modification, and specifically, it may be a microorganism of the genus *Corynebacterium*, a microorganism of the genus *Escherichia*, or a yeast.

The microorganism of the genus *Corynebacterium* may specifically be *Corynebacterium glutamicum, Corynebacterium ammoniagenes, Brevibacterium lactofermentum, Brevibacterium flavum, Corynebacterium thermoaminogenes, Corynebacterium efficiens*, etc., and more specifically, it may be *Corynebacterium glutamicum*, but is not limited thereto.

The microorganism of the genus *Escherichia* may specifically be *Escherichia albertii, Escherichia coli, Escherichia fergusonii, Escherichia hermannii, Escherichia vulneris*, etc., and more specifically, it may be *Escherichia coli*, but is not limited thereto.

The yeast may specifically be a microorganism belonging to Saccharomycotina, Taphrinomycotina of Ascomycota, or Agaricomycotina, Pucciniomycotina of Basidiomycota, etc., and more specifically, it may be a microorganism of the genus *Saccharomyces*, a microorganism of the genus *Schizosaccharomyces*, a microorganism of the genus of *Phaffia*, a microorganism of the genus of *Kluyveromyces*, a microorganism of the genus of *Pichia*, or a microorganism of the genus of *Candida*, and even more specifically, it may be *Saccharomyces cerevisiae*, but is not limited thereto.

In the present disclosure, the yeast for producing a mycosporine-like amino acid may be introduced with a gene encoding the 3-dehydroquinate synthase or may have an enhanced 3-dehydroquinate synthase activity. For example, if a part or all of ARO1 is deleted in order to inactivate the 3-dehydroquinate dehydratase activity in the yeast, the function of 3-dehydroquinate synthase is lost, and thus it may be difficult to synthesize 3-DHQ. Therefore, when a part or all of the ARO1 gene in the yeast is deleted, a gene encoding 3-dehydroquinate synthase (e.g., aroB gene) may be introduced, but is not limited thereto.

Another aspect of the present disclosure provides a method for producing a mycosporine-like amino acid, including:
  culturing the microorganism of the present disclosure; and
  recovering a mycosporine-like amino acid from the cultured microorganism or medium.

The "microorganism" and "mycosporine-like amino acids" are as described above.

As used herein, the term "culture" refers to growing the microorganism in an appropriately adjusted environment. The culture process of the present disclosure may be achieved according to an appropriate medium and culture conditions known in the art. The culture process may be easily adjusted for use by those skilled in the art according to the microorganism to be selected. The step of culturing the microorganism may be performed by a known batch culture method, continuous culture method, fed-batch culture method, etc., but is not particularly limited thereto. The medium used for culturing the microorganism of the present disclosure and other culture conditions are not particularly limited, but any medium used for the conventional culturing of the microorganism may be used. Specifically, the microorganism of the present disclosure may be cultured in a conventional medium containing suitable carbon sources, nitrogen sources, phosphorous sources, inorganic compounds, amino acids and/or vitamins, etc., in an aerobic condition while adjusting temperature, pH, etc. Specifically, the pH of the culture may be adjusted to a suitable pH (e.g., pH 5 to 9, specifically pH 6 to 8, and most specifically pH 6.8) using a basic compound (e.g., sodium hydroxide, potassium hydroxide, or ammonia) or acidic compound (e.g., phosphoric acid or sulfuric acid), but is not limited thereto. Additionally, oxygen or oxygen-containing gas may be injected into the culture in order to maintain an aerobic state of the culture; or nitrogen gas, hydrogen gas or carbon dioxide gas, or no gas may be injected to maintain an anaerobic or microaerobic state, but is not limited thereto. Additionally, the culture temperature may be maintained at 20 to 45° C., specifically at 25 to 40° C., and the culturing may be performed for about 10 to 160 hours, but the culture is not limited thereto. Additionally, foam formation may be prevented during culturing using an antifoaming agent such as fatty acid polyglycol ester, etc., but is not limited thereto.

Additionally, as a carbon source for the culture medium to be used, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but is not limited thereto. As a nitrogen source, nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but is not limited thereto. As a phosphorus source, potassium dihydrogen phosphate, dipotassium hydrogen phosphate, corresponding sodium-containing salts thereof, etc. may be used alone or in combination, but is not limited thereto. Further, essential growth-promoting materials such as other metal salts (e.g., magnesium sulfate or iron sulfate), amino acids, vitamins, etc. may be contained in the medium.

The MAAs produced by the culture may be secreted into the medium or may remain in the cells.

As used herein, the term "medium" refers to a product obtained after culturing the microorganism of the present disclosure. The medium is a concept that includes both a form containing the microorganism and a form in which the microorganism is removed by centrifugation, filtration, etc., from a culture solution containing the microorganism.

In the step for recovering MAAs produced in the culturing step of the present disclosure, the desired MAAs may be collected from the culture solution using an appropriate method known in the art. For example, centrifugation, filtration, anion-exchange chromatography, crystallization, HPLC, etc. may be used, and the desired MAAs may be recovered from the cultured microorganism or the medium using an appropriate method known in the art. Additionally, the step for recovering MAAs may further include a separation process and/or a purification step.

MODE FOR CARRYING OUT THE INVENTION

The present disclosure will be described in more detail by way of Examples. However, these Examples are given for illustrative purposes only, and the scope of the present disclosure is not intended to be limited to or by these Examples <Construction of MAAs-Producing Recombinant Microorganisms Derived from *E. coli* and Production of MAAs Using the Same>

Example 1: Construction of Vectors Overexpressing Shinorine Biosynthetic Gene Derived from Microalgae A *A. variabilis*-based shinorine biosynthetic gene cluster is composed of four genes, that is, 2-demethyl 4-deoxygadusol synthase, O-methyltransferase, C—N ligase, and non-ribosomal peptide synthetase, and *Nostoc punctiforme*, a species of cyanobacterium, can also produce shinorine using the genes. The shinorine biosynthetic gene clusters were identified using the genomic DNA of *A. variabilis* ATCC29413 and *N. punctiforme* ATCC29133. Four vectors, each of which contains the shinorine biosynthetic genes (Ava ABCD and Npr ABCD) derived from *A. variabilis* ATCC29413 and *N. punctiforme* ATCC29133, respectively, were constructed using the two types of vectors pECCG 117_Ptrc_GFP_terminator and pECCG 117_Pcj1_GFP_terminator. The name of the four shinorine biosynthetic gene expression vectors, and the templates and primers used for constructing the vectors are summarized in Table 1 below.

TABLE 1

| Name of Vectors | Templates used | Primers used |
|---|---|---|
| pECCG117_Ptrc_Ava_ABCD | *A. variabilis* ATCC29413 genomic DNA | SEQ ID NO: 5 (Forward) |
| pECCG117_Pcj1_Ava_ABCD | | SEQ ID NO: 6 (Reverse) |
| pECCG117_Ptrc_Npr_ABCD | *N. punctiforme* ATCC29133 genomic DNA | SEQ ID NO: 7 (Forward) |
| pECCG117_Pcj1_Npr_ABCD | | SEQ ID NO: 8 (Reverse) |

After obtaining gene fragments using the templates and the primers, each gene fragment was ligated to the pECCG 117_Ptrc_GFP_terminator and pECCG 117_Pcj1_GFP_terminator vectors treated with EcoRV/XbaI restriction enzyme using the In-Fusion® HD Cloning Kit (Clontech Laboratories, Inc.). The expression vectors were named pECCG117_Ptrc_Ava_ABCD, pECCG117_Pcj1_Ava_ABCD, pECCG117_Ptrc_Npr_ABCD, and pECCG117_Pcj1_Npr_ABCD, respectively, and each of the expression vectors were confirmed by sequencing. The nucleotide sequences and amino acid sequences of Ava_ABCD and Npr_ABCD were specified as SEQ ID NO: 1, SEQ ID NO: 2, SEQ ID NO: 3, and SEQ ID NO: 4, respectively.

Example 2: Evaluation of Shinorine-Producing Ability of Strains Introduced with Shinorine Biosynthetic Gene Expression Vectors In order to confirm the MAA-producing ability in *E. coli*, four plasmids prepared in Example 1 were introduced into the W3110 strain, a wild type *E. coli*, to prepare strains with enhanced shinorine biosynthesis. The thus-produced strains were plated on a LB solid medium containing kanamycin and then cultured overnight in a 37° C. incubator. One platinum loop of each strain cultured overnight in the LB solid medium was inoculated into 25 ml of a titer medium [medium composition: 40 g/L of glucose, 0.3 g/L of $KH_2PO_4$, 0.6 g/L of $K_2HPO_4$, 15 g/L of $(NH_4)_2SO_4$, 1 g/L of $MgSO_4.7H_2O$, 2.5 g/L of NaCl, 1.2 g/L of sodium citrate, 2.5 g/L of yeast extract, 40 g/L of calcium carbonate: pH 7.0], and then cultured in an incubator at 37° C. at a rate of 200 rpm for 48 hours. The results are shown in Table 2 below.

TABLE 2

| Name of Strains | OD (600 nm) | Shinorine Concentration (mg/L) |
|---|---|---|
| W3110 | 22.3 | — |
| W3110/pECCG117_Ptrc_Ava_ABCD | 20.1 | 121 |
| W3110/pECCG117_PCJ1_Ava_ABCD | 19.8 | 382 |
| W3110/pECCG117_Ptrc_Npr_ABCD | 21.0 | 96 |
| W3110/pECCG117_PCJ1_Npr_ABCD | 20.2 | 332 |

As shown in Table 2 above, when the shinorine biosynthetic genes were introduced into W3110, it was confirmed that shinorine production was possible. Additionally, it was confirmed that the production of shinorine was increased by increasing the intensity of the promoters (promoter PCJ1 introduced) through the enhancement of the biosynthetic pathway.

Example 3: Construction of Strains in which 3-Dehydroquinate Dehydratase is Inactivated Ava-A, the first gene for the biosynthesis of MAAs in microalgae, shares and uses, as substrates, DHQ (3-dehydroquinate) in the shikimate pathway and SH-7P (sedoheptulose 7-phosphate) in the pentose phosphate pathway. In order to prepare strains in which 3-dehydroquinate dehydratase is inactivated by deletion of aroD gene, a homologous recombination method using the lambda red recombinase was employed. As a gene insertion marker, a chloramphenicol-resistance gene of pKD3 was used, and an aroD-deleted cassette including a part of the aroD gene and the chloramphenicol-resistance gene of pKD3 plasmid was constructed by PCR using primers of SEQ ID NOS: 9 (forward) and 10 (reverse). After preparing strains (wild-type E. coli W3110) in which the aroD gene is to be deleted (SEQ ID NOS: 71 and 72), pKD46 plasmid containing a lambda red recombinase gene was transformed into the strains, and subsequently, the expression of the gene was induced using arabinose so as to prepare competent cells. The aroD-deleted cassette was introduced into the competent cells by electroporation, and then the cells were plated on a LB solid medium containing 30 mg/L of chloramphenicol. Thus-obtained strains were subjected to PCR using primers of SEQ ID NOS: 11 (forward) and 12 (reverse), and the aroD gene deletion was confirmed by observing the 1300 bp amplified-fragments.

Example 4: Evaluation of Shinorine-Producing Ability of Strains in which 3-Dehydroquinate Dehydratase is Inactivated Two plasmids, whose expression is controlled by the PCJ1 promoter among the four plasmids prepared in Example 1, were introduced into the strains, in which the aroD gene is deleted, prepared in Example 3 (W3110ΔaroD/pECCG117_PCJ1_Ava_ABCD and W3110ΔaroD/pECCG117_PCJ1_Npr_ABCD), and then the strains were plated on a LB solid medium containing kanamycin. Subsequently, the aroD-deleted strains and the strains without aroD deletion were respectively cultured overnight in a 37□ incubator, and one platinum loop of each strain was inoculated into 25 mL of a titer medium [medium composition: 40 g/L of glucose, 0.3 g/L of $KH_2PO_4$, 0.6 g/L of $K_2HPO_4$, 15 g/L of $(NH_4)_2SO_4$, 1 g/L of $MgSO_4 \cdot 7H_2O$, 2.5 g/L of NaCl, 1.2 g/L of Sodium citrate, 2.5 g/L of yeast extract, 40 g/L of calcium carbonate: pH 7.0], and then cultured in an incubator at 37° C. at a rate of 200 rpm for 48 hours. The results are shown in Table 3 below.

TABLE 3

| Name of Strains | OD (600 nm) | Shinorine Concentration (mg/L) |
| --- | --- | --- |
| W3110/pECCG117_PCJ1_Ava_ABCD | 20.3 | 352 |
| W3110ΔaroD/pECCG117_PCJ1_Ava_ABCD | 18.7 | 683 |
| W3110/pECCG117_PCJ1_Npr_ABCD | 18.9 | 331 |
| W3110ΔaroD/pECCG117_PCJ1_Npr_ABCD | 17.9 | 601 |

As shown in Table 3, the concentration of shinorine produced in the aroD-deleted strains was increased by 194% and 182% compared to the concentration or shinorine produced in the strains without aroD deletion, respectively. Accordingly, the W3110ΔaroD/pECCG117_PCJ1_Ava_ABCD strain and W3110ΔaroD/pECCG117_PCJ1_Npr_ABCD strain, which are aroD-deleted strains, were named CB06-0017 and CB06-0018 and deposited at the Korean Culture Center of Microorganisms (KCCM) under Budapest Treaty on Jun. 26, 2017, with Accession Nos. KCCM12044P and KCCM12045P, respectively.

Example 5: Construction of Strains Having Enhanced Activity of 2-Dehydro-3-Deoxyphosphoheptonate Aldolase/Phosphoenolpyruvate Synthetase/Transketolase I/II In order to increase the MAA-producing ability of the MAA-producing microorganisms, the activity of 2-dehydro-3-deoxyphosphoheptonate aldolase/phosphoenolpyruvate synthetase/transketolase I/II was enhanced. Specifically, three genes derived from E. coli W3110, namely, aroG (2-dehydro-3-deoxyphosphoheptonate aldolase; SEQ ID NOS: 73 and 74), ppsA (phosphoenolpyruvate synthetase; SEQ ID NOS: 75 and 76), and tktA (transketolase I/II; SEQ ID NOS: 77 and 78) were further introduced. pSKH130-ΔfhuA-Pn-aroG-Pn-ppsA-Pn-tktA plasmids were constructed to enhance the aroG, ppsA, and tktA genes. The template and primers used in the construction of the pSKH130-ΔfhuA-Pn-aroG-Pn-ppsA-Pn-tktA plasmids were shown in Table 4 below.

TABLE 4

| PCR Products | Template used | Primers used (Forward, Reverse) |
| --- | --- | --- |
| Pn-aroG | W3110 genomic DNA | SEQ ID NO: 13, SEQ ID NO: 14 |
| Pn-ppsA | | SEQ ID NO: 15, SEQ ID NO: 16 |
| Pn-tktA | | SEQ ID NO: 17, SEQ ID NO: 18 |

Using the template and primers above, aroG, ppsA, and tktA gene fragments were amplified by PCR, and then respectively introduced into the pSKH130-ΔfhuA vector cleaved with the BamH1-Pst1 restriction enzyme. Sequencing was applied to confirm the cloning and the gene sequences of the vectors, and then the vectors were transformed into the wild-type E. coli W3110 and aroD-deleted E. coli W3110ΔaroD by electroporation. The transformed genes were introduced into the chromosome by a primary recombination (crossover), followed by excision of the plasmid region from the chromosome by a secondary recombination (crossover). The introduction of aroG, ppsA, and tktA genes was confirmed in the E. coli transformed strains, in which the second recombination was completed, using primers of SEQ ID NOS: 19 (forward) and 20 (reverse)

Example 6: Evaluation of Shinorine-Producing Ability of Strains Having Enhanced Activity of 2-Dehydro-3-Deoxyphosphoheptonate Aldolase/Phosphoenolpyruvate Synthetase/Transketolase I/II Two plasmids, whose expression is controlled by the PCJ1 promoter among the four plasmids prepared in Example 5, were respectively introduced into the strains introduced with the aroG, ppsA, and tktA genes prepared in Example 5, and then the strains were plated on a LB solid medium. Subsequently, the strains were cultured overnight in a 37□ incubator, and one platinum loop of each strain was inoculated into 25 mL of the titer medium of Example 4, and then cultured in an incubator at 37° C. at a rate of 200 rpm for 48 hours. The results are shown in Table 5 below.

TABLE 5

| Name of Strains | OD (600 nm) | Shinorine Concentration (mg/L) |
| --- | --- | --- |
| W3110/pECCG117_PCJ1_Ava_ABCD | 19.8 | 352 |
| W3110/pECCG117_PCJ1_Npr_ABCD | 19.6 | 344 |
| W3110ΔaroD/ pECCG117_PCJ1_Ava_ABCD | 17.3 | 688 |
| W3110ΔaroD/pECCG117_PCJ1_Npr_ABCD | 17.8 | 652 |
| W3110ΔfhuA::Pn-aroG-Pn-ppsA-pn-tktA/ pECCG117_PCJ1_Ava_ABCD | 18.9 | 1163 |
| W3110ΔfhuA::Pn-aroG-Pn-ppsA-pn-tktA/ pECCG117_PCJ1_Npr_ABCD | 18.6 | 989 |
| W3110ΔaroDΔfhuA::Pn-aroG-Pn-ppsA-pn-tktA/pECCG117_PCJ1_Ava_ABCD | 17.3 | 1928 |
| W3110ΔaroDΔfhuA::Pn-aroG-Pn-ppsA-pn-tktA/pECCG117_PCJ1_Npr_ABCD | 17.7 | 1889 |

As shown in Table 5, the concentration of shinorine produced in the strains, in which three genes (aroG, ppsA, and tktA) were enhanced, was increased by about 300% compared to the control group.

Example 7: Construction of Ava_ABCD Chromosomal Insertion Vectors and Strains

In order to introduce the shinorine biosynthetic genes into E. coli, pSKH130ΔpinR::Ava-ABCD plasmids were prepared. Ava_ABCD was subjected to PCR using a primer pair of SEQ ID NOS: 21 (forward) and 22 (reverse) based on pECCG117_Ptrc_Ava_ABCD as a template. About 7 kb PCR fragments were ligated to pSKH130ΔpinR vector treated with BamHI and PstI restriction enzymes so as to prepare pSKH130ΔpinR::Ava_ABCD using the In-Fusion® HD Cloning Kit (Clontech Laboratories, Inc.). Subsequently, Ptrc and PCJ1 promoter fragments were subjected to PCR using forward and reverse primer pairs of SEQ ID NOS: 23 and 24, SEQ ID NOS: 25 and 26, and SEQ ID NOS: 25 and 27, respectively, to control the expression of Ava-ABCD. Then, the fragments were ligated to pSKH130ΔpinR::Ava_ABCD vector treated with the SeaI restriction enzyme so as to prepare pSKH130ΔpinR::Ptrc-Ava-ABCD and pSKH130ΔpinR::PCJ1-Ava-ABCD using the In-Fusion® HD Cloning Kit (Clontech Laboratories, Inc.). The recombinant plasmids were transformed into the W3110ΔaroDΔfhuA::Pn-aroG-Pn-ppsA-Pn-tktA strains prepared in Example 5 by electroporation, and the strains were introduced into the chromosome by a primary recombination (crossover), followed by excision of the vector region except the target gene from the chromosome by a secondary recombination (crossover).

The introduction of the Ava_ABCD gene was confirmed in the E. coli transformed strains, in which the second recombination was completed, by PCR using primers of SEQ ID NOS: 28 (forward) and 29 (reverse).

Example 8: Evaluation of Shinorine-Producing Ability of Ava_ABCD Chromosomal Insertion Strains The strains prepared in Example 7 were plated on a LB solid medium and then cultured overnight in a 37° incubator.

Subsequently, one platinum loop of each strain was inoculated into 25 ml of the titer medium of Example 4, and then cultured in an incubator at 37° C. at a rate of 200 rpm for 48 hours. The results are shown in Table 6 below.

TABLE 6

| Name of Strains | OD (600 nm) | Shinorine Concentration (mg/L) |
| --- | --- | --- |
| W3110ΔaroDΔfhuA::Pn-aroG-Pn-ppsA-Pn-tktA | 18.5 | — |
| W3110ΔaroDΔfhuA::Pn-aroG-Pn-ppsA-Pn-tktA/pECCG117_PCJ1_Ava_ABCD | 17.8 | 1928 |
| W3110ΔaroDΔfhuA::Pn-aroG-Pn-ppsA-Pn-tktAΔpinR::Ptrc-Ava-ABCD | 18.2 | 483 |
| W3110ΔaroDΔfhuA::Pn-aroG-Pn-ppsA-Pn-tktAΔpinR::PCJ1-Ava-ABCD | 17.9 | 832 |

As shown in Table 6, when Ava-ABCD was introduced into the chromosome, it was confirmed that shinorine was produced, and the concentration thereof was increased according to the intensity of the promoters. However, it was also confirmed that shinorine production was reduced compared to the strains having enhanced shinorine biosynthesis through the plasmids. When the pECCG117_PCJ1_Ava_ABCD plasmid was additionally introduced into the strains introduced with Ava-ABCD on the chromosome, shinorine production was increased by 353% and 152% compared to the strain only introduced with Ava-ABCD on the chromosome (based on the CJ1 promoter) and the strain only introduced with the plasmid, respectively.

Example 9: Construction of MAA Gene Overexpression Vectors and Evaluation of MAA-Producing Ability Thereof 4-deoxygadusol and mycosporine-glycine are intermediates that are produced during the shinorine biosynthesis and are mycosporine-like amino acids having an effect of preventing UV rays at the same time. Vectors were constructed in order to confirm whether these substances could be produced in AroD-deleted strains of E. coli. The results are shown in Table 7 below.

Ptrc_Ava_AB and Ptrc_Ava_ABC were subjected to PCR using primer pairs of SEQ ID NOS: 30 and 31 and SEQ ID NOS: 30 and 32 based on pECCG117_Ptrc_Ava_ABCD as a template. pECCG117_Ptrc_Ava_AB and pECCG117_Ptrc_Ava_ABC were prepared by ligating PCR fragments to pECCG117 Prc GFP vector treated with BamHI and SpeI restriction enzymes. In the same manner, pECCG117_PCJ1_Ava_AB and pECCG117_PCJ1_Ava_ABC were prepared by ligating the PCR fragments obtained using primers pairs of SEQ ID NOS: 30 and 31 and SEQ ID NOS: 30 and 32 based on pECCG117_PCJ1_Ava_ABCD as a template to the pECCG117 Pcj1 GFP vector treated with BamHI and SpeI restriction enzymes. The nucleotide sequence and amino acid sequence of Ava_AB and Ava_ABC are specified as SEQ ID NOS: 85 to 88.

TABLE 7

| Name of Vectors | Templates used | Primers used |
|---|---|---|
| pECCG117_Ptrc_Ava_AB | pECCG117_Ptrc_Ava_ABCD | SEQ ID NO: 30 (Forward) |
| pECCG117_PCJ1_Ava_AB | | SEQ ID NO: 31 (Reverse) |
| pECCG117_Ptrc_Ava_ABC | pECCG117_PCJ1_Ava_ABCD | SEQ ID NO: 30 (Forward) |
| pECCG117_PCJ1_Ava_ABC | | SEQ ID NO: 32 (Reverse) |

The thus-prepared vectors were transformed into W3110ΔaroDΔfhuA::Pn-aroG-Pn-ppsA-Pn-tktA strains used in Example 8 by commonly used electric-pulse method, and each strain was plated on a LB solid medium and cultured overnight in a 37° C. incubator. The strains cultured overnight in the LB solid medium were inoculated into 25 mL of the titer medium of Example 4, and then cultured in an incubator at 37° C. at a rate of 200 rpm for 48 hours. After completion of the culture, the production of MAAs was measured by liquid high-speed chromatography, and the concentration of MAAs in the culture for each strain tested was shown in Table 8 below.

TABLE 8

| Name of Strains | OD (600 nm) | 4-Deoxygadusol Concentration (mg/L) | Mycosporine glycine Concentration (mg/L) |
|---|---|---|---|
| W3110ΔaroDΔfhuA::Pn-aroG-Pn-ppsA-Pn-tktA | 19.2 | — | — |
| W3110ΔaroDΔfhuA::Pn-aroG-Pn-ppsA-Pn-tktA/ pECCG117_Ptrc_Ava_AB | 18.2 | 12.0 | — |
| W3110ΔaroDΔfhuA::Pn-aroG-Pn-ppsA-Pn-tktA/ pECCG117_Pcj1_Ava_AB | 17.6 | 25.3 | — |
| W3110ΔaroDΔfhuA::Pn-aroG-Pn-ppsA-Pn-tktA/ pECCG117_Ptrc_Ava_ABC | 18.7 | 2.0 | 9.3 |
| W3110ΔaroDΔfhuA::Pn-aroG-Pn-ppsA-Pn-tktA/ pECCG117_Pcj1_Ava_ABC | 18.1 | 2.9 | 19.7 |

As shown in Table 8, when the Ava_AB and Ava_ABC genes were introduced, it was confirmed that 4-deoxygadusol and mycosporine glycine were produced, and the amount thereof was increased as the intensity of the promoters was enhanced.

<Construction of MAA-Producing Recombinant Microorganisms Derived from *Corynebacterium glutamicum* and Production of MAAs Using the Same>

Example 10: Evaluation of Shinorine Producing-Ability of Strains Introduced with Shinorine Biosynthetic Gene Overexpression Vectors In order to confirm the MAA-producing ability of *Corynebacterium glutamicum*, four plasmids prepared in Example 1 were introduced into *Corynebacterium glutamicum* 13032 strain to prepare strains having enhanced shinorine biosynthesis, and the strains were plated on a BHIS solid medium containing kanamycin and cultured overnight in a 30 incubator. One platinum loop of each strain cultured overnight in the BHIS solid medium was inoculated into 25 mL of a titer medium [medium composition: 40 g/L of glucose, 1 g/L of KH$_2$PO$_4$, 10 g/L of (NH$_4$)$_2$SO$_4$, 5 g/L of MgSO$_4$.7H$_2$O, 5 g/L of NaCl, 5 g/L of yeast extract, 30 g/L of calcium carbonate: pH 7.0], and then cultured in an incubator at 37° C. at a rate of 200 rpm for 48 hours. The results are shown in Table 9 below.

TABLE 9

| Name of Strains | OD (600 nm) | Shinorine Concentration (mg/L) |
|---|---|---|
| c.gl 13032 | 72.1 | — |
| c.gl 13032/ pECCG117_Ptrc_Ava_ABCD | 71.5 | 132 |
| c.gl 13032/ pECCG117_PCJ1_Ava_ABCD | 69.8 | 496 |
| c.gl 13032/ pECCG117_Ptrc_Npr_ABCD | 70.9 | 103 |
| c.gl 13032/ pECCG117_PCJ1_Npr_ABCD | 71.4 | 421 |

As shown in Table 9, it was confirmed that shinorine production was possible when the shinoine biosynthetic genes were introduced into *Corynebacterium glutamicum* 13032, and the production thereof could be increased by up to 375% depending on the intensity of the promoters.

Example 11: Construction of Vectors Introduced with Shinorine Biosynthetic Gene on the Chromosome and Strains In order to introduce the shinorine biosynthetic genes into *Corynebacterium glutamicum*, pDC ΔN1021_Ava_ABCD plasmids was prepared. Ava_ABCD was subjected to PCR using a primer pair of SEQ ID NOS: 33 (forward) and 34 (reverse) based on pECCG117_Ptrc_Ava_ABCD as a template. About 7 kb PCR fragments were ligated to pDC ΔN1021 vector treated with the NdeI restriction enzyme so as to prepare pDC ΔN1021_Ava_ABCD using the In-Fusion® HD Cloning Kit (Clontech Laboratories, Inc.). Subsequently, CJ7, Lysc8, and 02 promoter fragments were subjected to PCR using forward and reverse primer pairs of SEQ ID NOS: 35 and 36, SEQ ID NOS: 37 and 38, and SEQ ID NOS: 39 and 40, respectively, in order to control the expression of Ava-ABCD. Then, the fragments were ligated to pDC ΔN1021_Ava_ABCD vector treated with the NdeI restriction enzyme to prepare pDC ΔN1021_Pcj7_Ava_ABCD, pDC ΔN1021_Plysc8_Ava_ABCD and pDC ΔN1021_PO2_Ava_ABCD using the In-Fusion® HD Cloning Kit (Clontech Laboratories, Inc.).

The recombinant plasmids were transformed into *Corynebacterium glutamicum* 13032 by electroporation (van der Rest et al. 1999), and introduced into the chromosome by a primary recombination (crossover), followed by plasmid excision from the chromosome by a secondary recombination (crossover).

The introduction of the Ava_ABCD gene was confirmed in the *Corynebacterium glutamicum* transformed strains, in which the second recombination was completed, by PCR using a gene-specific primer pair of SEQ ID NOS: 33 (forward) and 34 (reverse).

Example 12: Evaluation of Shinorine-Producing Ability of Strains Introduced with Shinorine Biosynthetic Gene on the Chromosome All strains were plated on a BHIS solid medium and then cultured overnight in a 30 incubator to confirm the shinorine-producing ability. One platinum loop of each strain cultured overnight in the BHIS solid medium was inoculated into 25 mL of the titer medium of Example 11, and then cultured in an incubator at 37° C. at a rate of 200 rpm for 48 hours. The results are shown in Table 10 below.

TABLE 10

| Name of Strains | OD (600 nm) | Shinorine Concentration (mg/L) |
| --- | --- | --- |
| c.gl 13032 | 70.2 | — |
| c.gl 13032 ΔN1021_PCJ7_Ava_ABCD | 76.1 | 36 |
| c.gl 13032 ΔN1021_Plysc8_Ava_ABCD | 79.8 | 75 |
| c.gl 13032 ΔN1021_PO2_Ava_ABCD | 72.5 | 173 |

As shown in Table 10, it was confirmed that, when a single copy of the shinorine biosynthetic genes was introduced into the wild-type *Corynebacterium glutamicum*, shinorine could be produced in an amount from 36 mg to 173 mg.

Example 13: Construction of *Corynebacterium* aroD (3-Dehydroquinate Dehydratase)-Deleted Vectors and Strains As mentioned in Example 3, strains with deletion were prepared to confirm whether shinorine production could be increased through the deletion of aroD (3-dehydroquinate dehydratase). In order to prepare a site-specific aroD gene (SEQ ID NOS: 79 and 80)-deleted strains of *Corynebacterium glutamicum*, pDC-ΔaroD plasmids, in which an open reading frame of aroD was endogenously deleted, were constructed. The endogenous gene deletion of the pDC-ΔaroD was generated by introducing gene fragments generated by crossover-PCR using forward and reverse primer pairs of SEQ ID NOS: 41 and 42, and SEQ ID NOS: 43 and 44, based on the genomic DNA of *Corynebacterium glutamicum* ATCC 13032 as a template into the pDC vector. The recombinant plasmids were transformed into *Corynebacterium glutamicum* 13032 ΔN1021_PO2_Ava_ABCD by electroporation (van der Rest et al. 1999), and the plasmids were introduced into the chromosome by a primary recombination (crossover), followed by plasmid excision from the chromosome by a secondary recombination (crossover).

The deletion of aroD gene was confirmed in the *Corynebacterium glutamicum* transformed strains, in which the second recombination was completed, by PCR using a gene-specific primer pair of SEQ ID NOS: 41 and 44.

Example 14: Evaluation of aroD (3-Dehydroquinate Dehydratase) Deletion

Strains expected to have DHQ accumulation due to deletion of 3-dehydroquinate dehydratase in the *Corynebacterium glutamicum* 13032 ΔN1021_PO2_Ava_ABCD strain were plated on a BHIS solid medium and cultured overnight in a 30 incubator. One platinum loop of each strain cultured overnight in the BHIS solid medium was inoculated into 25 mL of a titer medium [medium composition: 40 g/L of glucose, 1 g/L of KH$_2$PO$_4$, 10 g/L of (NH$_4$)$_2$SO$_4$, 5 g/L of MgSO$_4$.7H$_2$O, 5 g/L of NaCl, 5 g/L of yeast extract, 30 g/L of calcium carbonate: pH7.0], and then cultured in an incubator at 37° C. at a rate of 200 rpm for 48 hours. The results are shown in Table 11 below.

TABLE 11

| Name of Strains | OD (600 nm) | Shinorine Concentration (mg/L) |
| --- | --- | --- |
| c.gl 13032 ΔN1021_PO2_Ava_ABCD | 71.3 | 182 |
| c.gl 13032 ΔN1021_PO2_Ava_ABCD_ΔaroD | 74.1 | 435 |
| c.gl 13032 ΔN1021_PO2_Ava_ABCD_ΔaroD/ pECCG117_PCJ1_Ava_ABCD | 73.2 | 1162 |

As shown in Table 11, it was confirmed that when the aroD gene was deleted, the concentration of shinorine was improved by 239% compared to the control group, and as the biosynthesis of shinorine was further enhanced through the pECCG117_PCJ1_Ava_ABCD, the concentration of shinorine was increased. Accordingly, the aroD-deleted strain, c.gl 13032 N1021_PO2_Ava_ABCD_ΔaroD, was named CB06-0019 and deposited at the Korean Culture Center of Microorganisms (KCCM) under Budapest Treaty on Jun. 26, 2017, with Accession No. KCCM12046P.

<Construction of MAA-Producing Recombinant Microorganisms Derived from Yeast and Production of MAAs Using the Same>

Example 15: Construction of Shinorine Biosynthetic Gene Overexpression Yeast Vectors Derived from Microalgae

*S. cerevisiae* vectors, into which the shinorine biosynthetic genes were introduced based on the genomic DNA of *A. variabilis* ATCC29413 and *N. punctiforme* ATCC29133, were constructed. The vectors were prepared using the ADH, TEF, and GPD promoters of *S. cerevisiae*, and the templates and primers used to prepare a total of twenty-four shinorine biosynthetic gene expression vectors are shown in Table 12 below. Nucleotide sequences and amino acid sequences of Ava_A, Ava_B, Ava_C, Ava_D, Npr_A, Npr_B, Npr_C, and Npr_D are specified as SEQ ID NOS: 89 to 104 in the order of the enzymes.

TABLE 12

| Name of Vectors | Templates Used | Primers used (Forward, Reverse) |
| --- | --- | --- |
| p413-pADH-Ava_A | *A. variabilis* ATCC29413 genomic DNA | SEQ ID NO: 45, SEQ ID NO: 46 |
| p413-pADH-Ava_B | | SEQ ID NO: 47, SEQ ID NO: 48 |
| p413-pADH-Ava_C | | SEQ ID NO: 49, SEQ ID NO: 50 |
| p413-pADH-Ava_D | | SEQ ID NO: 51, SEQ ID NO: 52 |
| p413-pTEF-Ava_A | | SEQ ID NO: 45, SEQ ID NO: 46 |
| p413-pTEF-Ava_B | | SEQ ID NO: 47, SEQ ID NO: 48 |
| p413-pTEF-Ava_C | | SEQ ID NO: 49, SEQ ID NO: 50 |
| p413-pTEF-Ava_D | | SEQ ID NO: 51, SEQ ID NO: 52 |
| p413-pGPD-Ava_A | | SEQ ID NO: 45, SEQ ID NO: 46 |
| p413-pGPD-Ava_B | | SEQ ID NO: 47, SEQ ID NO: 50 |
| p413-pGPD-Ava_C | | SEQ ID NO: 49, SEQ ID NO: 50 |
| p413-pGPD-Ava_D | | SEQ ID NO: 51, SEQ ID NO: 52 |
| p413-pADH-Npr_A | *N. punctiforme* ATCC29133 genomic DNA | SEQ ID NO: 53, SEQ ID NO: 54 |
| p413-pADH-Npr_B | | SEQ ID NO: 55, SEQ ID NO: 56 |
| p413-pADH-Npr_C | | SEQ ID NO: 57, SEQ ID NO: 58 |
| p413-pADH-Npr_D | | SEQ ID NO: 59, SEQ ID NO: 60 |
| p413-pTEF-Npr_A | | SEQ ID NO: 53, SEQ ID NO: 54 |
| p413-pTEF-Npr_B | | SEQ ID NO: 55, SEQ ID NO: 56 |

TABLE 12-continued

| Name of Vectors | Templates Used Primers used (Forward, Reverse) |
|---|---|
| p413-pTEF-Npr_C | SEQ ID NO: 57, SEQ ID NO: 58 |
| p413-pTEF-Npr_D | SEQ ID NO: 59, SEQ ID NO: 60 |
| p413-pGPD-Npr_A | SEQ ID NO: 53, SEQ ID NO: 54 |
| p413-pGPD-Npr_B | SEQ ID NO: 55, SEQ ID NO: 56 |
| p413-pGPD-Npr_C | SEQ ID NO: 57, SEQ ID NO: 58 |
| p413-pGPD-Npr_D | SEQ ID NO: 59, SEQ ID NO: 60 |

The gene fragments obtained by PCR using the combination of templates and primers above were ligated to p413/414/415/416-pADH/pTEF/pGPD-CYC1_terminator vector treated with the BamH1/XhoI restriction enzyme using the T4 ligase enzyme (NEB), thereby preparing twenty-four p413/414/415/416-pADH/pTEF/pGPD-A, B, C, D vectors. Construction of each expression vector and gene sequences thereof were confirmed by sequencing techniques. The thus-prepared expression vectors were introduced into a wild-type S. cerevisiae CEN.PK-1D strain so as to prepare strains capable of producing shinorine.

Example 16: Evaluation of Shinorine-Producing Ability of Strains Introduced with Shinorine Biosynthetic Gene Overexpression Vectors In order to confirm the MAA-producing ability of yeasts, twenty-four plasmids prepared in Example 15 were introduced into the *Saccharomyces cerevisiae* CEN.PK-1D strain (*S. cerevisiae* CEN.PK-1D) to prepare strains having enhanced shinorine biosynthesis, and the strains were plated on a SC (synthetic complete) solid medium excluding Leu, Trp, Ura, and His and cultured overnight in a 30 incubator. One platinum loop of each strain cultured overnight was inoculated into 25 mL of the titer medium shown in Table 13 and then cultured in an incubator at 30 at a rate of 150 rpm for 24 hours. The results are shown in Table 14 below.

TABLE 13

| Composition | Concentration (g/L) |
|---|---|
| YNB(Yeast nitrogen base) without amino acids | 6.7 |
| Amino acid mixtures (without Leucine, Tryptophan, Histidine, Uracil) | 2 |
| Glucose | 20 |

TABLE 14

| | 24 hr | | Shinorine Concentration |
|---|---|---|---|
| Plasmid | OD$_{600}$ | Residual Sugar | (mg/L) |
| pADH-Ava_A, B, C, D | 11.0 | 0.0 | 107 |
| pTEF-Ava_A, B, C, D | 11.1 | 0.0 | 215 |
| pGPD-Ava_A, B, C, D | 11.5 | 0.0 | 302 |
| pADH-Npr_A, B, C, D | 20.1 | 0.0 | 234 |
| pTEF-Npr_A, B, C, D | 20.4 | 0.0 | 387 |
| pGPD-Npr_A, B, C, D | 20.5 | 0.0 | 521 |

Based on the results above, it was confirmed that the *S. cerevisiae* CEN.PK-1D (i.e., a yeast strain) showed a high activity for Npr A, B, C, D genes compared to Ava A, B, C, D genes. Additionally, it is confirmed that the expression level of the genes was controlled according to the intensity of the promoters, and thus, the production of shinorine was altered. In particular, it was confirmed that the shinorine production was the highest (521 mg/L) when the GPD (Glyceraldehyde-3-phosphate dehydrogenase) promoter-based Npr A, B, C, D vector was introduced

Example 17: Increase of Shinorine Production by ARO1 Deletion in S. cerevisiae and Introduction of E. coli aroB In order to determine whether the inactivation of dehydroquinate dehydratase improves shinorine production in yeasts, the ARO1 gene was deleted in *S. cerevisiae* CEN.PK-1D. The ARO1 gene of *S. cerevisiae* is a gene that serves five functions, and the function of 3-dehydroquinate synthase corresponding to *E. coli* aroB is lost upon deletion of the ARO1 gene, making the synthesis of 3-DHQ impossible. Therefore, after deletion of the *S. cerevisiae* ARO1 gene (SEQ ID NOS: 81 and 82), which is an *E. coli* aroB homologue on the chromosome, the *E. coli* aroB gene (SEQ ID NOS: 83 and 84) was inserted at the same position based on the GPD promoter. The templates and primers used are shown in Table 15. The twenty-four plasmids prepared in Example 15 were introduced into the *S. cerevisiae* CEN.PK-1D strain, in which the ARO1 gene is deleted and the *E. coli* aroB gene is introduced, and the strains were plated on a SC (synthetic complete) solid medium excluding Leu, Trp, Ura, and His and cultured overnight in a 30 incubator. One platinum loop of each strain cultured overnight was inoculated into 25 mL of the titer medium shown in Table 13 and then cultured in an incubator at 30 at a rate of 150 rpm for 24 hours. The results are shown in Table 16 below.

TABLE 15

| Name of Cassette | Amplified DNA | Template | Sequence Nos. (Forward, Reverse) |
|---|---|---|---|
| ARO1ΔpGPD-aroB cassette | pGPD | S. cerevisiae gDNA | SEQ ID NO: 61, SEQ ID NO: 62 |
| | LoxP(Ura) | pUG28 vector | SEQ ID NO: 63, SEQ ID NO: 64 |
| | aroB | W3110 gDNA | SEQ ID NO: 65, SEQ ID NO: 66 |
| | ARO1 Fragment1 | S. cerevisiae gDNA | SEQ ID NO: 67, SEQ ID NO: 68 |
| | ARO1 Fragment2 | S. cerevisiae gDNA | SEQ ID NO: 69, SEQ ID NO: 70 |

TABLE 16

| | 24 hr | | Shinorine Concentration |
|---|---|---|---|
| Plasmids | OD$_{600}$ | Residual Sugar | (mg/L) |
| WT pADH-Ava_A, B, C, D | 11.0 | 0.0 | 103 |
| WT pTEF-Ava_A, B, C, D | 11.1 | 0.0 | 235 |
| WT pGPD-Ava_A, B, C, D | 11.5 | 0.0 | 323 |
| WT pADH-Npr_A, B, C, D | 20.1 | 0.0 | 230 |
| WT pTEF-Npr_A, B, C, D | 20.4 | 0.0 | 390 |
| WT pGPD-Npr_A, B, C, D | 20.5 | 0.0 | 545 |
| S. cerevisiae ARO1Δ4GPD-aroB, pADH-Ava_A, B, C, D | 13.0 | 0.0 | 305 |
| S. cerevisiae ARO1Δ4GPD-aroB, pTEF-Ava_A, B, C, D | 13.1 | 0.0 | 635 |
| S. cerevisiae ARO1Δ4GPD-aroB, pGPD-Ava_A, B, C, D | 13.3 | 0.0 | 912 |
| S. cerevisiae ARO1Δ4GPD-aroB, pADH-Npr_A, B, C, D | 24.1 | 0.0 | 670 |
| S. cerevisiae ARO1Δ4GPD-aroB, pTEF-Npr_A, B, C, D | 25.3 | 0.0 | 1230 |

TABLE 16-continued

| Plasmids | 24 hr | | Shinorine Concentration (mg/L) |
|---|---|---|---|
| | OD$_{600}$ | Residual Sugar | |
| S. cerevisiae ARO1Δ4GPD-aroB, pGPD-Npr_A, B, C, D | 24.8 | 0.0 | 1600 |

Based on the results shown in Table 16, it was confirmed that shinorine production was increased by 3-fold in the strains, in which the DHQ-producing ability was enhanced by ARO1 deletion and *E. coli* aroB introduction, compared to the WT strains. Additionally, it was confirmed that the strains showed a high activity for Npr A, B, C, D genes compared to Ava A, B, C, D genes, and that the shinorine production was increased as the intensity of the promoters increased. In particular, it was confirmed that the shinorine production was the highest (1.6 g/L) when the GPD promoter-based Npr A, B, C, D vector was introduced Those skilled in the art will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A microorganism for producing a mycosporine-like amino acid, wherein an activity of 3-dehydroquinate dehydratase is inactivated as compared to a corresponding non-modified microorganism and wherein the microorganism comprises a heterologous mycosporine-like amino acid biosynthesis gene comprising a 2-demethyl 4-deoxygadusol synthase gene from a Cyanobacterium.

2. The microorganism of claim 1, wherein the mycosporine-like amino acid biosynthesis gene further comprises a gene encoding at least one protein selected from the group consisting of O-methyltransferase and C—N ligase.

3. The microorganism of claim 1, wherein the mycosporine-like amino acid biosynthesis gene further comprises a gene encoding at least one protein selected from the group consisting of non-ribosomal peptide synthetase, non-ribosomal peptide synthetase-like enzyme (NRPS-like enzyme), and D-Ala D-Ala ligase.

4. The microorganism of claim 1, wherein an activity of at least one protein selected from the group consisting of 2-dehydro-3-deoxyphosphoheptonate aldolase, phosphoenolpyruvate synthetase, transketolase I/II, and 3-dehydroquinate synthase is further enhanced as compared to a corresponding non-modified microorganism.

5. The microorganism of claim 1, wherein the microorganism is a microorganism of the genus *Corynebacterium*, a microorganism of the genus *Escherichia*, or a yeast.

6. The microorganism of claim 5, wherein the yeast is introduced with a gene encoding 3-dehydroquinate synthase.

7. The microorganism of claim 1, wherein the mycosporine-like amino acid is at least one selected from the group consisting of deoxygadusol, shinorine, and mycosporine-glycine.

8. A method for producing a mycosporine-like amino acid, comprising:
    culturing the microorganism of claim 1 in a medium; and
    recovering a mycosporine-like amino acid from the cultured microorganism or the cultured medium.

9. The method for producing a mycosporine-like amino acid of claim 8, wherein the mycosporine-like amino acid biosynthesis gene further comprises a gene encoding at least one protein selected from the group consisting of O-methyltransferase and C—N ligase.

10. The method for producing a mycosporine-like amino acid of claim 8, wherein the mycosporine-like amino acid biosynthesis gene further comprises a gene encoding at least one protein selected from the group consisting of non-ribosomal peptide synthetase, non-ribosomal peptide synthetase-like enzyme (NRPS-like enzyme), and D-Ala D-Ala ligase.

11. The method for producing a mycosporine-like amino acid of claim 8, wherein an activity of at least one protein selected from the group consisting of 2-dehydro-3-deoxyphosphoheptonate aldolase, phosphoenolpyruvate synthetase, transketolase I/II, and 3-dehydroquinate synthase is further enhanced as compared to a corresponding non-modified microorganism.

12. The method for producing a mycosporine-like amino acid of claim 8, wherein the microorganism is a microorganism of the genus *Corynebacterium*, a microorganism of the genus *Escherichia*, or a yeast.

13. The method for producing a mycosporine-like amino acid of claim 12, wherein the yeast is introduced with a gene encoding 3-dehydroquinate synthase.

14. The method for producing a mycosporine-like amino acid of claim 8, wherein the mycosporine-like amino acid is at least one selected from the group consisting of deoxygadusol, shinorine, and mycosporine-glycine.

* * * * *